(12) United States Patent
Williams et al.

(10) Patent No.: US 7,118,907 B2
(45) Date of Patent: Oct. 10, 2006

(54) SINGLE MOLECULE DETECTION SYSTEMS AND METHODS

(75) Inventors: John G. K. Williams, Lincoln, NE (US); Gregory R. Bashford, Lincoln, NE (US)

(73) Assignee: Li-Cor, Inc., Lincoln, NE (US)

( * ) Notice: Subject to any disclaimer, the term of this patent is extended or adjusted under 35 U.S.C. 154(b) by 424 days.

(21) Appl. No.: 10/164,685

(22) Filed: Jun. 5, 2002

(65) Prior Publication Data

US 2003/0186255 A1   Oct. 2, 2003

Related U.S. Application Data

(63) Continuation-in-part of application No. 09/876,375, filed on Jun. 6, 2001.

(60) Provisional application No. 60/381,864, filed on May 16, 2002.

(51) Int. Cl.
C12M 1/34    (2006.01)
C12M 3/00    (2006.01)

(52) U.S. Cl. .............. 435/287.1; 435/287.2; 435/287.3; 435/287.9; 435/288.3; 435/288.4; 435/288.5; 435/288.7

(58) Field of Classification Search .......... 435/287.1, 435/287.2, 287.3, 287.9, 288.3, 288.4, 288.5, 435/288.7
See application file for complete search history.

(56) References Cited

U.S. PATENT DOCUMENTS

| | | | |
|---|---|---|---|
| 3,687,808 A | 8/1972 | Merigan, Jr. et al. |
| 3,996,345 A | 12/1976 | Ullman et al. |
| 4,351,760 A | 9/1982 | Khanna et al. |
| 4,415,732 A | 11/1983 | Caruthers et al. |
| 4,458,066 A | 7/1984 | Caruthers et al. |
| 4,725,677 A | 2/1988 | Köster et al. |
| 4,739,044 A | 4/1988 | Stabinsky |
| 4,793,705 A | 12/1988 | Shera |
| 4,855,225 A | 8/1989 | Fung et al. |
| 4,973,679 A | 11/1990 | Caruthers et al. |
| 4,979,824 A | 12/1990 | Mathies et al. |
| 4,980,460 A | 12/1990 | Molko et al. |
| 5,047,519 A | 9/1991 | Hobbs, Jr. et al. |

(Continued)

FOREIGN PATENT DOCUMENTS

WO    WO 98/28440 A1    7/1998

(Continued)

OTHER PUBLICATIONS

Ishikawa et al., "Single-Molecule Detection by Laser-Induced Fluorescence Technique with a Position-Sensitive Photon-Counting Apparatus," *Jpn. J. Apple. Phys.*, 33:1571-1576 (Mar. 1994).

(Continued)

*Primary Examiner*—Jeffrey Fredman
*Assistant Examiner*—Teresa Strzelecka
(74) *Attorney, Agent, or Firm*—Townsend and Townsend and Crew LLP; Gerald T. Gray

(57) ABSTRACT

A microfluidic system is provided that includes a substrate, a first microchannel disposed in the substrate for providing a reactant to a reaction zone, a second microchannel disposed in the substrate, and a third microchannel disposed in the substrate, the third microchannel providing fluid communication between the first and second microchannels. The system also typically includes first and second electrodes, positioned at opposite ends of the second microchannel, for providing an electric field within the second microchannel. In operation, when the reactant is in the reaction zone, a reaction product is produced having a net electric charge different from the electric charge of the reactant.

23 Claims, 30 Drawing Sheets

U.S. PATENT DOCUMENTS

| | | |
|---|---|---|
| 5,151,507 A | 9/1992 | Hobbs, Jr. et al. |
| 5,231,191 A | 7/1993 | Woo et al. |
| 5,405,747 A | 4/1995 | Jett et al. |
| 5,449,767 A | 9/1995 | Ward et al. |
| 5,578,443 A | 11/1996 | Santamaria et al. |
| 5,605,662 A | 2/1997 | Heller et al. |
| 5,637,458 A | 6/1997 | Frankel et al. |
| 5,674,743 A | 10/1997 | Ulmer |
| 5,776,677 A | 7/1998 | Tsui et al. |
| 5,795,782 A | 8/1998 | Church et al. |
| 5,814,524 A | 9/1998 | Walt et al. |
| 5,863,502 A | 1/1999 | Southgate et al. |
| 6,191,266 B1 | 2/2001 | Wang |
| 6,210,891 B1 | 4/2001 | Nyren et al. |
| 6,232,075 B1 | 5/2001 | Williams |
| 6,255,083 B1 | 7/2001 | Williams |
| 6,376,181 B1 | 4/2002 | Ramsey et al. |
| 6,391,622 B1 | 5/2002 | Knapp et al. |
| 6,409,900 B1 | 6/2002 | Parce et al. |
| 2002/0039738 A1 | 4/2002 | Williams et al. |
| 2002/0042071 A1 | 4/2002 | Williams et al. |
| 2003/0064400 A1 | 4/2003 | Williams |
| 2003/0190608 A1* | 10/2003 | Blackburn ............. 435/6 |

FOREIGN PATENT DOCUMENTS

| | | |
|---|---|---|
| WO | WO 99/05315 A2 | 2/1999 |
| WO | WO 00 36151 A1 | 6/2000 |
| WO | WO 00 36152 | 6/2000 |
| WO | WO 00/67907 A2 | 11/2000 |
| WO | WO 00 70073 | 11/2000 |
| WO | WO 02/099406 A2 | 12/2002 |

OTHER PUBLICATIONS

Lyon et al., "Confinement and Detection of Single Molecules in Submicrometer Channels" *Anal. Chem.*, 69:3400-3405 (1997).

Paige, et al., "A Comparison of Through-the-Objective Total Internal Reflection Microscopy and Epifluorescence Microscopy for Single-Molecule Fluorescence Imaging" *Single Mol*, 2(3):191-201 (2001).3.

Chou et al., "A microfabricated device for sizing and sorting DNA molecules" *Proc. Natl. Acad. Sci USA*, 96:11-13 (Jan. 1999).

Fu et al., "A microfabricated fluorescence-activated cell sorter" *Nat. Biotech.* 17:1109-1111 (Nov. 1999).

Ha, T., "Single-Molecule Fluorescence Resonance Energy Transfer" *Methods*. 25:78-86 (2001).

Xu et al., "Direct Measurement of Single-Molecule Diffusions and Photodecomposition in Free Solution" *Science*, 275:1106-1109 (Feb. 21, 1997).

Casoli et al., "Fluorescence Correlation Spectroscopy as a Tool to Investigate Single Moleucre Probe dynamics in Thin Polymer Films" *Biol. Chem.*, 382:363-369 (Mar. 2001).

U.S. Appl. No. 60/214,714, filed Aug. 24, 2001.

U.S. Appl. No. 60/314,709, filed Aug. 24, 2001.

Ambrose, W. Patrick et al.: "Single-Molecule Detection With Total Internal Reflection Excitation: Comparing Signal-to-Background and Total Signals in Different Geometries"; *Cytometry*; vol. 36; pp. 224-231 (1999).

Asanov, Alexander N. et al.: "Regenerable Biosensor Platform: A Total Internal Reflection Fluorescence Cell with Electrochemical Control"; *Anal. Chem.*; vol. 70; pp. 1156-1163 (1998).

Castro, Alonso and John G. K. Williams: "Single-Molecule Detection of Specific Nucleic Acid Sequences in Unamplified Genomic DNA"; *Anal. Chem.*; Vol. 69; pp. 3915-3920 (1997).

Davis, Lloyd M. et al.: "Rapid DNA Sequencing Based Upon Single Molecule Detection"; *GATA*; vol. 8, No. 1: pp. 1-7 (1991).

Eigen, Manfred and Rudolf Rigler: "Sorting single molecules: Application to diagnostic and evolutionary biotechnology"; *Proc. Natl. Acad. Sci. U.S.A.*; vol. 91; pp. 5740-5747 (1994).

Funatsu, Takashi et al.: "Imaging of single fluorescent molecules and individual ATP turnovers by single myosin molecules in aqueous solution"; *Nature*; vol. 374; pp. 555-559 (1995).

Hirschfeld, T.: "Optical microscopic observation of single small molecules"; *Applied Optics*; vol. 15, No. 12; pp. 2965-2966 (1976).

Jett, James H. et al.: "High-Speed DNA Sequencing: An Approach Based Upon Fluorescence Detection of Single Molecules"; *Journal of Biomolecular Structure & Dynamics*; vol. 7, No. 2; pp. 301-309 (1989).

Lee, Yuan-Hsiang et al.: "Laser-induced fluorescence detection of a single molecule in a capillary"; *Anal. Chem.*; vol. 66; pp. 4142-4149 (1994).

Nie, Shuming et al.: "Probing Individual Molecules with Confocal Fluorescence Microscopy"; *Science*; vol. 266; pp. 1018-1021 (1994).

Nie, Shuming et al.: "Real-Time Detection of Single Molecules in Solution by Confocal Fluorescence Microscopy"; *Anal. Chem.*: vol. 67; pp. 2849-2857 (1995).

Nie, Shuming and Richard N. Zare, "Optical detection of single molecules"; *Annu. Rev. Biophys. Biomol. Struct.*; vol. 26; pp. 567-596 (1997).

Plakhotnik, Taras et al.: "Single-molecule spectroscopy"; *Annu. Rev. Phys. Chem.*; vol. 48; pp. 181-212 (1997).

Ronaghi, Mostafa et al.: "A Sequencing Method Based on Real-Time Pyrophosphate"; *Science*; vol. 281; pp. 363-365 (1998).

Schecker, Jay A. et al.: "Flow-based continuous DNA sequencing via single molecule detection of enzymatically cleaved fluorescent nucleotides"; *SPIE*; vol. 2386; pp. 4-12 (1995).

Schmidt, Th. et al.: "Imaging of single molecule diffusion"; *Proc. Natl. Acad. Sci. U.S.A.*; vol. 93; pp. 2926-2929 (1996).

Tokunaga, Makio et al.: "Single molecule imaging of fluorophores and enzymatic reactions achieved by objective-type total internal reflection fluorescence microscopy"; *Biochemical and Biophysical Research Communications*; vol. 235; pp. 47-53 (1997).

Vale, Ronald D. et al.: "Direct observation of single kinesin molecules moving along microtubules"; *Nature*; vol. 380; pp. 451-453 (1996).

\* cited by examiner

| NO. | IDEAL CONDITION: ALL BASE AND F ADDUCTS FULLY CHARGED ||||| IN PURE WATER |
| --- | --- | --- | --- | --- | --- | --- |
| | Charge on indicated moiety || Net charge ||| pH 7.0 |
| | NUCLEOBASE | F | NP PROBE | PPi-F | Change | Change |
| 1 | -3 | -3 | -9 | -6 | 3 | 3.25 |
| 2 | -3 | -2 | -8 | -5 | 3 | 3.25 |
| 3 | -3 | -1 | -7 | -4 | 3 | 3.25 |
| 4 | -3 | 0 | -6 | -3 | 3 | 3.25 |
| 5 | -3 | 1 | -5 | -2 | 3 | 3.25 |
| 6 | -3 | 2 | -4 | -1 | 3 | 3.25 |
| 7 | -3 | 3 | -3 | 0 | 3 | 3.25 |
| 8 | -2 | -3 | -8 | -6 | 2 | 2.26 |
| 9 | -2 | -2 | -7 | -5 | 2 | 2.26 |
| 10 | -2 | -1 | -6 | -4 | 2 | 2.26 |
| 11 | -2 | 0 | -5 | -3 | 2 | 2.26 |
| 12 | -2 | 1 | -4 | -2 | 2 | 2.26 |
| 13 | -2 | 2 | -3 | -1 | 2 | 2.26 |
| 14 | -2 | 3 | -2 | 0 | 2 | 2.26 |
| 15 | -1 | -3 | -7 | -6 | 1 | 1.26 |
| 16 | -1 | -2 | -6 | -5 | 1 | 1.26 |
| 17 | -1 | -1 | -5 | -4 | 1 | 1.26 |
| 18 | -1 | 0 | -4 | -3 | 1 | 1.26 |
| 19 | -1 | 1 | -3 | -2 | 1 | 1.26 |
| 20 | -1 | 2 | -2 | -1 | 1 | 1.26 |
| 21 | -1 | 3 | -1 | 0 | 1 | 1.26 |
| 22 | 0 | -3 | -6 | -6 | 0 | 0.26 |
| 23 | 0 | -2 | -5 | -5 | 0 | 0.26 |
| 24 | 0 | -1 | -4 | -4 | 0 | 0.26 |
| 25 | 0 | 0 | -3 | -3 | 0 | 0.26 |
| 26 | 0 | 1 | -2 | -2 | 0 | 0.26 |
| 27 | 0 | 2 | -1 | -1 | 0 | 0.26 |
| 28 | 0 | 3 | 0 | 0 | 0 | 0.26 |
| 29 | 1 | -3 | -5 | -6 | -1 | -0.74 |
| 30 | 1 | -2 | -4 | -5 | -1 | -0.74 |
| 31 | 1 | -1 | -3 | -4 | -1 | -0.74 |
| 32 | 1 | 0 | -2 | -3 | -1 | -0.74 |
| 33 | 1 | 1 | -1 | -2 | -1 | -0.74 |
| 34 | 1 | 2 | 0 | -1 | -1 | -0.74 |
| 35 | 1 | 3 | 1 | 0 | -1 | -0.74 |
| 36 | 2 | -3 | -4 | -6 | -2 | -1.74 |
| 37 | 2 | -2 | -3 | -5 | -2 | -1.74 |
| 38 | 2 | -1 | -2 | -4 | -2 | -1.74 |
| 39 | 2 | 0 | -1 | -3 | -2 | -1.74 |
| 40 | 2 | 1 | 0 | -2 | -2 | -1.74 |
| 41 | 2 | 2 | 1 | -1 | -2 | -1.74 |
| 42 | 2 | 3 | 2 | 0 | -2 | -1.74 |
| 43 | 3 | -3 | -3 | -6 | -3 | -2.74 |
| 44 | 3 | -2 | -2 | -5 | -3 | -2.74 |
| 45 | 3 | -1 | -1 | -4 | -3 | -2.74 |
| 46 | 3 | 0 | 0 | -3 | -3 | -2.74 |
| 47 | 3 | 1 | 1 | -2 | -3 | -2.74 |
| 48 | 3 | 2 | 2 | -1 | -3 | -2.74 |
| 49 | 3 | 3 | 3 | 0 | -3 | -2.74 |

FIG. 2 dTTP-BQS-BTR

| COMPOUND | CHARGE | NAME | STRUCTURE |
|---|---|---|---|
| 50 | N = -2 F = +2 | DBA-U-BQS-TAMRA X | 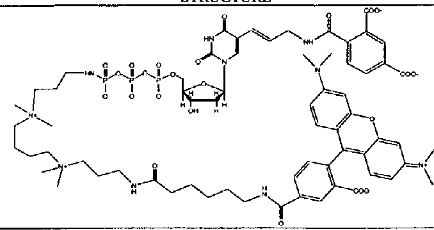 |
| 51 | N = -2 F = +1 | DBA-U-BQS-Oregon 500 | 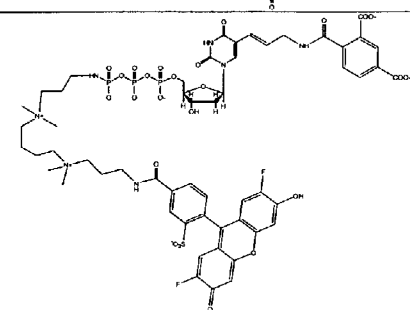 |
| 52 | N = -1 F = +2 | SUC-U-BQS-TAMRA X | 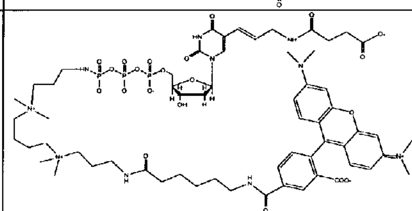 |

*FIG. 6A*

Scheme 7 - Peptide linkers (shown in C-to-N direction)
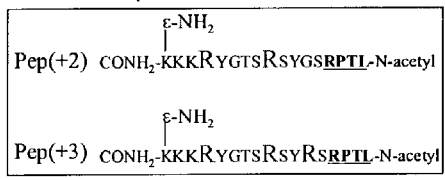
Scheme 8 - Peptide Deprotection By Thrombin Cleavage
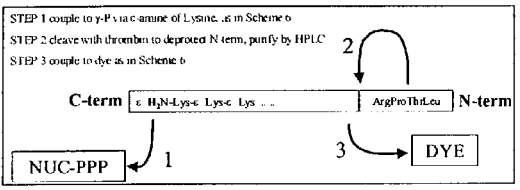
Scheme 9 - Add carboxylate to aminoally-dUTP
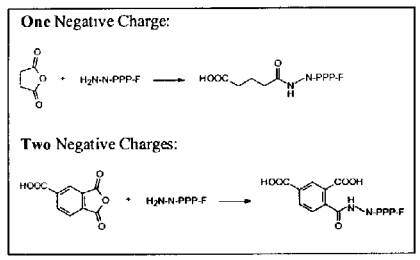
Scheme 10 - γ-dNTP With Carboxylated Base
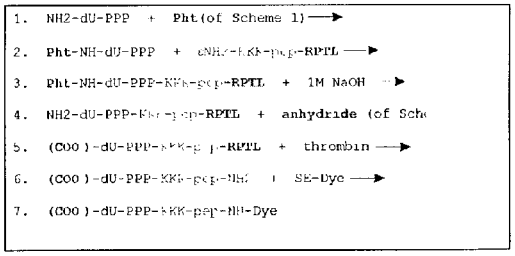
FIG. 6F

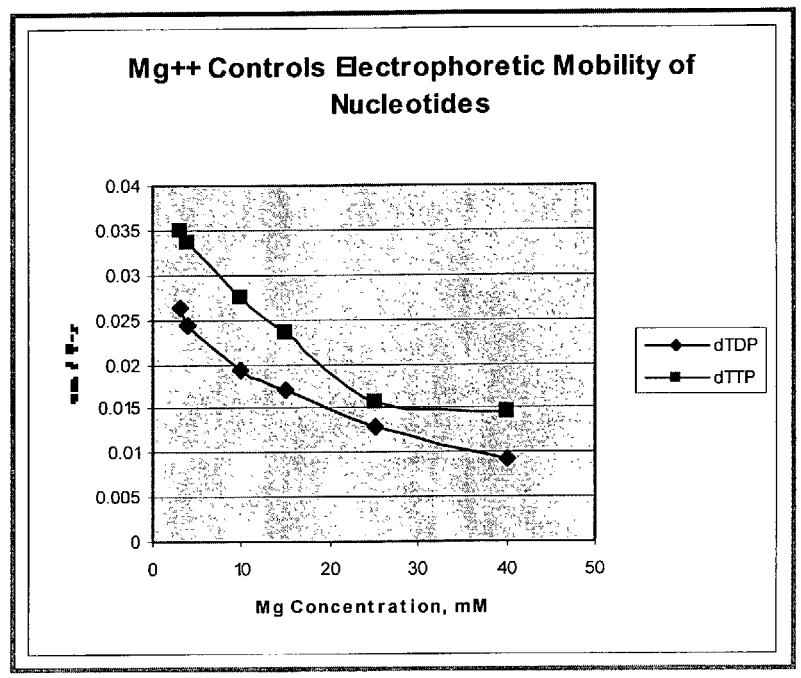
A
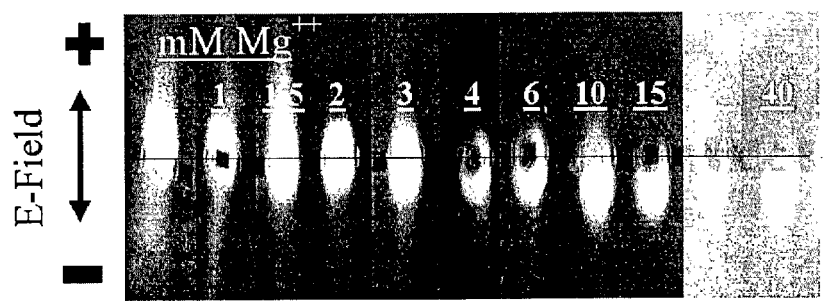
B
FIG. 11

Figure 15 - No E-field across Feed Channel or Extension Zone

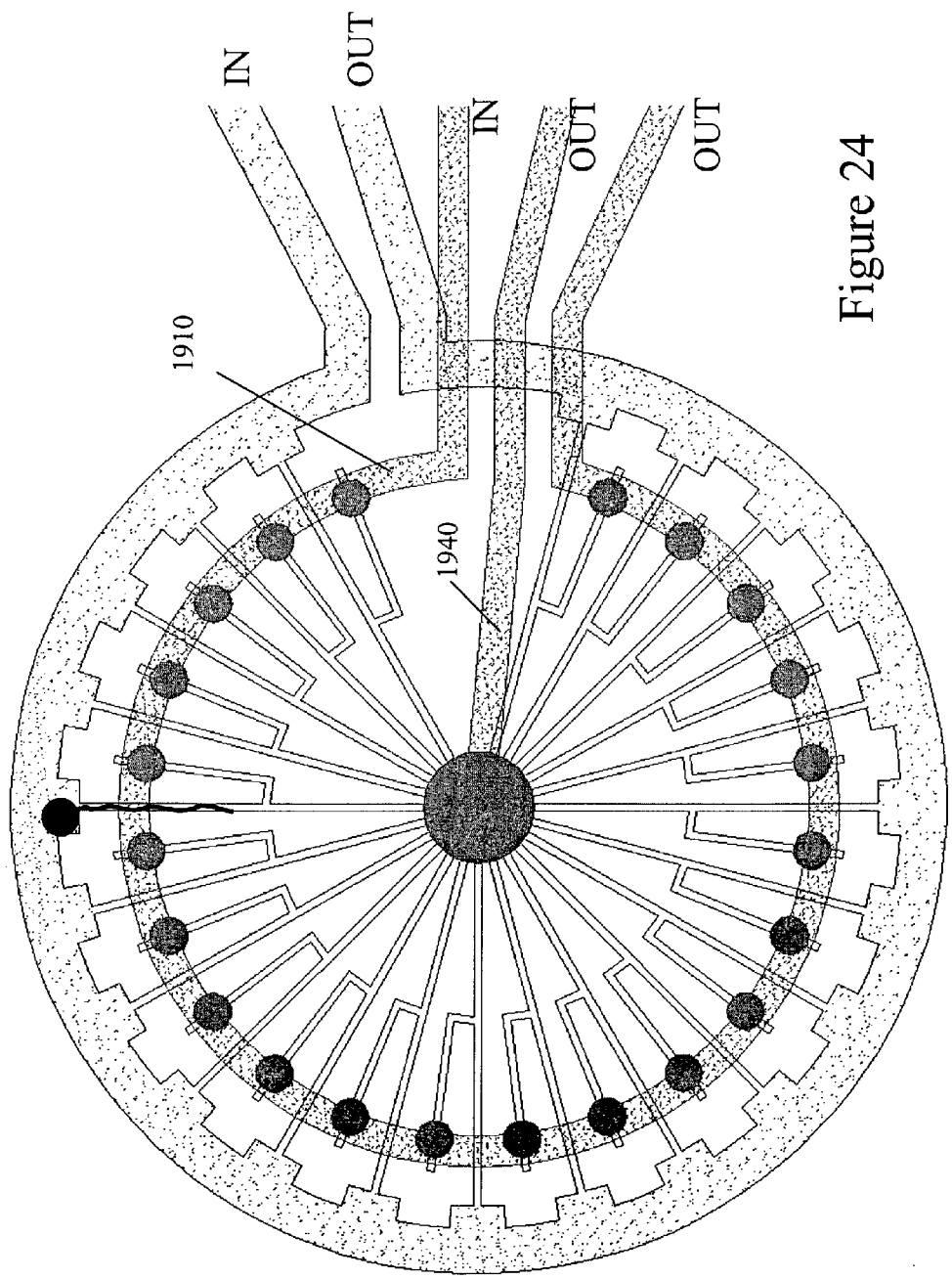

SEQUENCE LISTING

```
<160> NUMBER OF SEQ ID NOS: 3

<210> SEQ ID NO 1
<211> LENGTH: 17
<212> TYPE: PRT
<213> ORGANISM: Artificial Sequence
<220> FEATURE:
<223> OTHER INFORMATION: Description of Artificial Sequence:peptide
      linker Pep(+2)
<220> FEATURE:
<221> NAME/KEY: MOD_RES
<222> LOCATION: (1)
<223> OTHER INFORMATION: Xaa = N-acetyl Leu

<400> SEQUENCE: 1

Xaa Thr Leu Arg Ser Gly Tyr Ser Arg Ser Thr Gly Tyr Arg Lys Lys
 1               5                  10                  15

Lys

<210> SEQ ID NO 2
<211> LENGTH: 17
<212> TYPE: PRT
<213> ORGANISM: Artificial Sequence
<220> FEATURE:
<223> OTHER INFORMATION: Description of Artificial Sequence:peptide
      linker Pep(+3)
<220> FEATURE:
<221> NAME/KEY: MOD_RES
<222> LOCATION: (1)
<223> OTHER INFORMATION: Xaa = N-acetyl Leu

<400> SEQUENCE: 2

Xaa Thr Pro Arg Ser Arg Tyr Ser Arg Ser Thr Gly Tyr Arg Lys Lys
 1               5                  10                  15

Lys
```

```
-continued

<210> SEQ ID NO 3
<211> LENGTH: 4
<212> TYPE: PRT
<213> ORGANISM: Artificial Sequence
<220> FEATURE:
<223> OTHER INFORMATION: Description of Artificial Sequence:N-terminal
      protecting group

<400> SEQUENCE: 3

Leu Thr Pro Arg
 1
```

SINGLE MOLECULE DETECTION SYSTEMS AND METHODS

CROSS-REFERENCES TO RELATED APPLICATIONS

This application claims the benefit of U.S. Provisional Patent Application No. 60/381,864, filed May 16, 2002, and is a continuation-in-part of U.S. patent application Ser. No. 09/876,375, filed Jun. 6, 2001, the disclosures of which are all hereby incorporated by reference in their entirety for all purposes.

STATEMENT AS TO RIGHTS TO INVENTIONS MADE UNDER FEDERALLY SPONSORED RESEARCH OR DEVELOPMENT

This invention was made with Government support under the R44 HG02066 grant awarded by the PHS. The Government has certain rights to this invention.

BACKGROUND OF THE INVENTION

The primary sequences of nucleic acids are crucial for understanding the function and control of genes and for applying many of the basic techniques of molecular biology. In fact, rapid DNA sequencing has taken on a more central role after the goal to elucidate the entire human genome has been achieved. DNA sequencing is an important tool in genomic analysis as well as other applications, such as genetic identification, forensic analysis, genetic counseling, medical diagnostics, and the like. With respect to the area of medical diagnostic sequencing, disorders, susceptibilities to disorders, and prognoses of disease conditions, can be correlated with the presence of particular DNA sequences, or the degree of variation (or mutation) in DNA sequences, at one or more genetic loci. Examples of such phenomena include human leukocyte antigen (HLA) typing, cystic fibrosis, tumor progression and heterogeneity, p53 proto-oncogene mutations and ras proto-oncogene mutations (see, Gyllensten et al., *PCR Methods and Applications*, 1: 91–98 (1991); U.S. Pat. No. 5,578,443, issued to Santamaria et al.; and U.S. Pat. No. 5,776,677, issued to Tsui et al.).

Various approaches to DNA sequencing exist. The dideoxy chain termination method serves as the basis for all currently available automated DNA sequencing machines. (see, Sanger et al., *Proc. Natl. Acad. Sci.*, 74: 5463–5467 (1977); Church et al., *Science*, 240: 185–188 (1988); and Hunkapiller et al., *Science*, 254: 59–67 (1991)). Other methods include the chemical degradation method, (see, Maxam et al., *Proc. Natl. Acad. Sci.*, 74: 560–564 (1977), whole-genome approaches (see, Fleischmann et al., *Science*, 269, 496 (1995)), expressed sequence tag sequencing (see, Velculescu et al., *Science*, 270, (1995)), array methods based on sequencing by hybridization (see, Koster et al., *Nature Biotechnology*, 14, 1123 (1996)), and single molecule sequencing (SMS) (see, Jett et al., *J. Biomol. Struct. Dyn.* 7, 301 (1989) and Schecker et al., *Proc. SPIE-Int. Soc. Opt. Eng.* 2386, 4 (1995)).

PCT Application No. US99/29584, filed Dec. 13, 1999, and incorporated herein by reference, discloses a single molecule sequencing method on a solid support. The solid support is optionally housed in a flow chamber having an inlet and outlet to allow for renewal of reactants that flow past the immobilized polymerases. The flow chamber can be made of plastic or glass and should either be open or transparent in the plane viewed by the microscope or optical reader. Electro-osmotic flow requires a fixed charge on the solid support and a voltage gradient (current) passing between two electrodes placed at opposing ends of the solid support. The flow chamber can be divided into multiple channels for separate sequencing.

Much more recently, PCT Application No. US00/13677, filed May 18, 2000, discloses a method of sequencing a target nucleic acid molecule having a plurality of bases. The temporal order of base additions during the polymerization reaction is measured on a molecule of nucleic acid. The activity of a nucleic acid polymerizing enzyme on the template nucleic acid molecule is thereafter followed in time. The sequence is deduced by identifying which base is being incorporated into the growing complementary strand of the target nucleic acid by the polymerizing enzyme at each step in the sequence of base additions. The steps of providing labeled nucleotide analogs, polymerizing the growing nucleic acid strand, and identifying the added nucleotide analog are repeated so that the nucleic acid strand is further extended and then sequenced.

In addition, U.S. Pat. No. 4,979,824, describes that single molecule detection can be achieved using flow cytometry wherein flowing samples are passed through a focused laser with a spatial filter used to define a small volume. Moreover, U.S. Pat. No. 4,793,705 describes a detection system for identifying individual molecules in a flow train of the particles in a flowcell. The patent further describes methods of arranging a plurality of lasers, filters and detectors for detecting different fluorescent nucleic acid base-specific labels.

Single molecule detection on solid supports is described in Ishikawa, et al. *Jan. J. Apple. Phys.* 33:1571–1576. (1994). As described therein, single-molecule detection is accomplished by a laser-induced fluorescence technique with a position-sensitive photon-counting apparatus involving a photon-counting camera system attached to a fluorescence microscope. Laser-induced fluorescence detection of a single molecule in a capillary for detecting single molecules in a quartz capillary tube has also been described. The selection of lasers is dependent on the label and the quality of light required. Diode, helium neon, argon ion, argon-krypton mixed ion, and Nd:YAG lasers are useful in this invention (see, Lee et al. (1994) *Anal. Chem.*, 66:4142–4149).

A need currently exists for more effective and efficient compounds, methods, and systems for single molecule detection, especially as they relate to single molecule DNA sequencing. These and further needs are provided by the present invention.

BRIEF SUMMARY OF THE INVENTION

The present invention relates to methods and systems to analyze reactions and more particularly to determine and elucidate sequences of nucleic acids. Advantageously, the methods and systems of the present invention can be used to sequence nucleic acid rapidly and without the need for amplification or cloning.

In one embodiment, the present invention provides a charge-switch nucleotide phosphate (NP) probe, comprising: an intact NP probe having a terminal phosphate with a fluorophore moiety attached thereto, the intact NP probe having a first molecular charge associated therewith, whereupon cleavage of the terminal phosphate as a phosphate fluorophore moiety, the phosphate fluorophore moiety carries a second molecular charge, wherein the difference between the first molecular charge and the second molecular charge is at least 0.5. Preferably, the difference between the first molecular charge and the second molecular charge is at least 0.5 as calculated in pure water at pH 7.0. In preferred aspects, the charge difference is between about 1 and about 4, and any fraction therebetween. In certain preferred embodiments, the NP probe has a positive charge, or alternatively, upon cleavage of the terminal phosphate as a phosphate fluorophore moiety, the phosphate fluorophore moiety carries a positive charge relative to the NP probe.

In a preferred aspect, the NP probe is a nucleotide triphosphate (NTP), and the terminal phosphate is a γ-phosphate with a fluorophore moiety attached thereto. In certain aspects, the NP probe is incorporated into a growing nucleic acid strand that is complementary to a target nucleic acid, where upon a γ-phosphate with a fluorophore moiety attached thereto is released as a detectable pyrophosphate moiety.

In one embodiment, the present invention provides an intact charge-switch nucleotide phosphate (NP) probe, wherein, upon enzymatic cleavage of the intact charge-switch NP probe to produce a phosphate detectable moiety, the phosphate detectable moiety migrates to an electrode, and the intact charge-switch NP probe migrates to the other electrode.

In another embodiment, the present invention provides a method for separating a labeled nucleotide phosphate having a detectable moiety from a released charged detectable moiety in a sample stream, the method comprising: a) immobilizing a complex comprising a nucleic acid polymerase or a target nucleic acid onto a solid support in a single molecule configuration; b) contacting the complex with a sample stream comprising a target nucleic acid when the polymerase is immobilized, or a polymerase when the target nucleic acid is immobilized, a primer nucleic acid which complements a region of the target nucleic acid; and a labeled nucleotide phosphate having a detectable moiety, wherein the detectable moiety is released as a charged detectable moiety when the NP is incorporated into the primer nucleic acid; and c) applying an energy field to the sample stream, thereby separating the labeled NP from the charged detectable moiety.

In certain aspects, the NP is a labeled nucleotide triphosphate (NTP) having a detectable moiety and the detectable moiety is a γ-phosphate with a fluorophore moiety attached thereto. In a preferred aspect, the charge of the detectable moiety after release is different than the labeled nucleotide phosphate (NP) having a detectable moiety attached thereto.

In another embodiment, the present invention provides a method for sequencing a target nucleic acid comprising: a) immobilizing a complex comprising a nucleic acid polymerase, or a target nucleic acid onto a solid support in a single molecule configuration; b) contacting the complex with a sample stream comprising a target nucleic acid when the polymerase is immobilized, or a polymerase when the target nucleic acid is immobilized, a primer nucleic acid which complements a region of the target nucleic acid of the region to be sequenced; and a labeled nucleotide phosphate (NP) having a detectable moiety, wherein the detectable moiety is released as a charged detectable moiety when the NP is incorporated into the primer nucleic acid wherein the solid support is disposed in a flowcell having an inlet port and an outlet port; c) applying an energy field to the sample stream; and d) detecting the charged detectable moiety, thereby sequencing the target nucleic acid. In preferred aspects, the energy field is a first energy field such as an electric field applied in the transverse direction, and a second energy field such as a pressure field applied in the axial direction. In certain aspects, the first energy field is oriented transverse to the first channel. The nucleotide phosphate is preferably a nucleotide triphosphate.

Suitable nucleobases include, but are not limited to, adenine, guanine, cytosine, uracil, thymine, deazaadenine and deazaguanosine. In a preferred embodiment, the NPs are charge-switch γ-phosphate labeled dNTP. In one aspect, the polymerase is immobilized and the sample stream contains a target nucleic acid. In another aspects, the target nucleic acid is immobilized and the sample stream contains polymerase. In another aspect, the method includes applying an electric field transverse to the sample stream to sort between a reagent and a product.

In yet another aspect, the present invention provides a system that can be used to facilitate the contact of fluorescent-labeled nucleotides with polymerases, and thereafter remove them away (while emitting signals) from the optical field of view. The system is especially beneficial in single-molecule sequencing schemes to facilitate detection. As such, the present invention provides a microfabricated flowcell system for single-molecule detection, comprising: a) a flowcell having an inlet port and an outlet port wherein a sample stream having a detectable analyte flows therethrough; b) an energy field source applied to the sample stream; and c) a detector for detecting the analyte.

In certain aspects, the system comprises two energy fields, one axial to the sample stream and the other energy field applied in the transverse direction. Preferably, the applied fields are electric fields, pressure fields and combinations thereof. The fields are variable, thus permitting control of the motion of the nucleotides and (after incorporation) the phosphate detectable moiety (e.g., fluorescent-labeled phosphate).

In certain embodiments, the flowcell has multiple inlet ports and multiple outlet ports wherein a sample stream having detectable analytes flow therethrough. In addition to a first energy field and a second energy field, in certain aspects, the flowcell of the present invention comprises an array of energy fields disposed throughout the flowcell arrangement and an array of immobilized polymerases, target nucleic acids and combinations thereof in single molecule configuration. This arrangement can be used to analyze a plurality of nucleic acids in a single flowcell device.

According to a further aspect of the present invention, a microfluidic system is provided that typically includes a substrate, a first microchannel disposed in the substrate for providing a reactant to a reaction zone, a second microchannel disposed in the substrate, wherein at least a portion of the second microchannel is in a detection region, and a third microchannel disposed in the substrate, the third microchannel providing fluid communication between the first and second microchannels, wherein at least a portion of the third microchannel defines a portion of the reaction zone. the system also typically includes first and second electrodes, positioned at opposite ends of the second microchannel, for providing an electric field within the second microchannel. in operation, when the reactant is in the reaction zone, a reaction product is produced having a net electric charge different from the electric charge of the reactant, wherein the reaction product is separated from the reactant, and wherein the electric field in the second microchannel causes the reaction product to flow into the detection region.

According to yet a further aspect of the present invention, a microfluidic device useful for analyzing a reaction is provided. the device typically includes a substrate, at least two microchannels disposed on the substrate, wherein the microchannels are in fluid communication with each other, an immobilization zone within a first one of the at least two microchannels, wherein at least a portion of a reactant is immobilized proximal the immobilization zone to allow for a reaction to occur so as to produce a reaction product, and a detection zone within a second one of the microchannels. The device is configured so that there is substantially no electric field within the first microchannel proximal the immobilization zone. A biasing force is typically provided to move the reaction product into the detection zone within the second microchannel. In certain aspects, the ratios of electric fields in the first and second microchannels is relatively small, about 1:100–200, this allows for example, small fields to "hold" the nucleic acid in place.

According to still a further aspect of the present invention, a method is provided for sequencing or genotyping a nucleic acid in a microfluidics device having at least two microchannels disposed on a substrate in fluid communication with each other. The method typically includes immobilizing a nucleic acid complex proximal an immobilization region within a first one of said microchannels, and providing a polymerase and plurality of NP probes to a reaction region proximal the immobilization region under conditions permitting target dependent polymerization of said plurality of NP probes, thereby providing a product. The method also typically includes separating the product from polymerization reactants into a detection region in a second one of the microchannels using a biasing force sufficient to interact with the product, and detecting the product.

According to yet another aspect of the present invention, a microfluidic device useful for analyzing a reaction is provided. The device typically includes a substrate, a first microchannel disposed on the substrate, and a plurality of second microchannels disposed on the substrate, each in fluid communication with the first microchannel. The device also typically includes a plurality of immobilization zones within the first microchannel, each immobilization zone corresponding to one of the plurality of second microchannels, wherein a reactant is immobilized proximal each immobilization zone to allow for a reaction proximal each immobilization zone to produce a reaction product, and a detection zone within each of the plurality of second microchannels. the device is typically configured so that there is substantially no electric field within the first microchannel proximal each immobilization zone. A biasing force is typically provided to move the corresponding reaction product into the detection zone within each second microchannel.

Numerous benefits and advantages are achieved by way of the present invention over conventional compounds, methods and systems. For example, the charge-switch nucleotide phosphates allow separation of the cleaved terminal phosphate (e.g., pyrophosphate) from the intact nucleotide phosphate probe reagents. This characteristic is useful for single-molecule DNA sequencing in a microchannel sorting system with an energy field. Using 4 different NTPs each labeled with a unique dye, real-time DNA sequencing is possible by detecting the released pyrophosphate having different labels. By electrically sorting differently-charged molecules in this manner, the cleaved PPi-Dye molecules are detected in isolation without interference from unincorporated NTPs and without illuminating the polymerase-DNA complex.

With respect to the flowcell, the energy fields can be varied in accordance with the charge on a molecule to increase the probability of signal detection. Moreover, the flowcell of the present system increases the signal-to-noise ratio (S/N) of the detectable moiety. By increasing the S/N, a lower detection limit is possible.

These and other objects and advantages will become more apparent when read with the accompanying detailed description and drawings that follow.

BRIEF DESCRIPTION OF THE DRAWINGS

FIG. 2 tabulates various charges of charge-switch nucleotides according to the present invention. In the ideal condition, the charged groups attached to the nucleobase, sugar or on the label "F" are assumed to be in fully charged form. In the pure water condition, the effect of hydrogen ions on the net charge of the phosphate groups is calculated using equilibrium constants given by Frey and Stuhr (1972), *Journal of American Chemical Society*, 94:8818. Hydrogen ions confer a time-averaged partial positive charge preferentially to the PPi-F group as compared to the NP Probe due to the presence of the secondary ionization phosphate oxygen present only on the PPi-F group;

FIG. 11 PANEL A nucleotide electrophoretic velocities are plotted as a function of $Mg^{++}$ concentration. Panel B effect of $Mg^{++}$ on electrophoretic migration of the compound in FIG. 4 in agarose gels containing the indicated amounts of $Mg^{++}$;

FIGS. 21–24 illustrate a radial flowcell design according to embodiments of the present invention;

DETAILED DESCRIPTION OF THE INVENTION

I. Definitions

Figure 1:
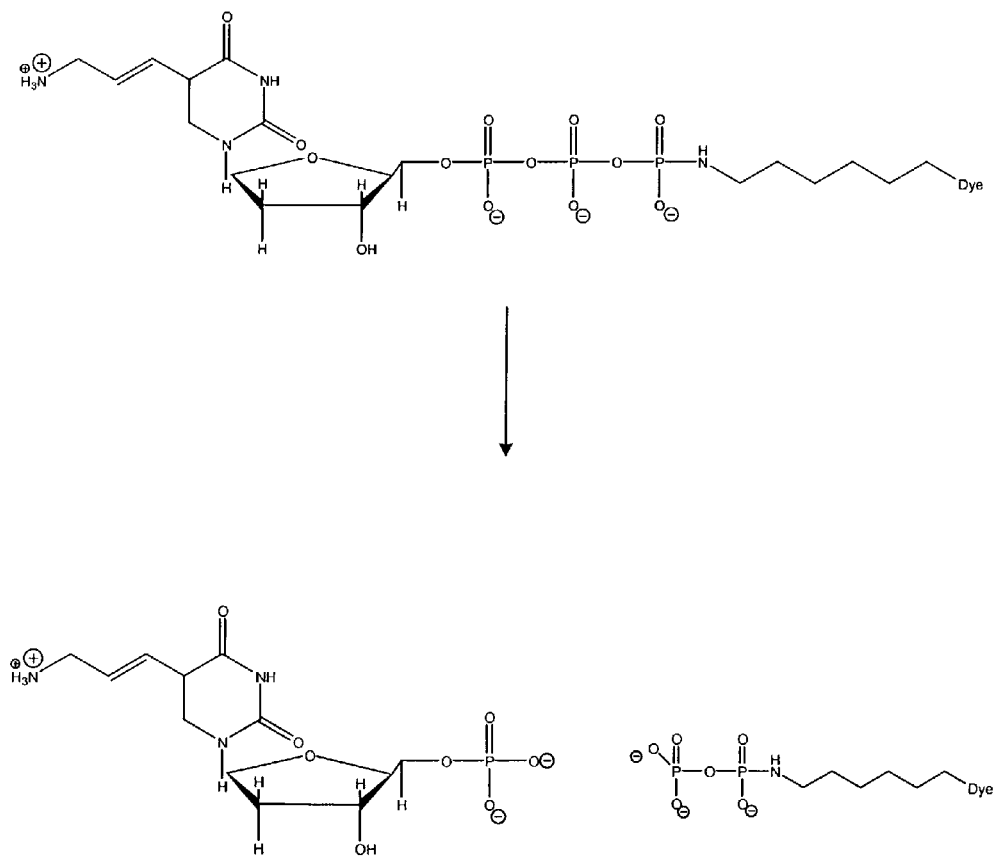
FIG. 1 illustrates a model compound of the present invention.

The term "charge-switch nucleotide" as used herein refers to a labeled nucleotide phosphate (e.g., γ-NP-Dye) that upon release or cleavage of a phosphate detectable moiety (e.g., PPi-Dye) has a different net charge associated with the cleavage product compared to the intact nucleotide phosphate probe (e.g., γ-NP-Dye). In certain preferred aspects, the attachment of the dye to the PPi is via a nitrogen in lieu of an oxygen. Preferably, the charge difference between the intact γ-NP-Dye and the PPi-Dye is at least 0.5, and more preferably about 1 to about 4 (e.g., 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, and 4.0).

The terms "PPi-Dye" or "PP-F" and the like, refer to the pyrophosphate cleavage product from an intact charge-switch nucleotide (NTP). If a nucleotide diphosphate is used, the cleavage product will be a "P-Dye" or "P-F".

The phrase "phosphate detectable moiety" refers to a detectable cleavage product from a NP probe of the present invention. Examples include, but are not limited to, PPi-Dye, PP-F, P-Dye, a phosphate fluorophore moiety, a terminal phosphate fluorophore moiety, a detectable moiety, charged groups, electrically active groups, detectable groups, reporter groups, combinations thereof, and the like.

The term "heterogeneous" assay as used herein refers to an assay method wherein at least one of the reactants in the assay mixture is attached to a solid phase, such as a solid support.

The term "oligonucleotide" as used herein includes linear oligomers of nucleotides or analogs thereof, including deoxyribonucleosides, ribonucleosides, and the like. Usually, oligonucleotides range in size from a few monomeric units, e.g. 3–4, to several hundreds of monomeric units. Whenever an oligonucleotide is represented by a sequence of letters, such as "ATGCCTG," it will be understood that the nucleotides are in 5 '–3' order from left to right and that "A" denotes deoxyadenosine, "C" denotes deoxycytidine, "G" denotes deoxyguanosine, and "T" denotes thymidine, unless otherwise noted.

The term "nucleoside" as used herein refers to a compound consisting of a purine, deazapurine, or pyrimidine nucleoside base, e.g., adenine, guanine, cytosine, uracil, thymine, deazaadenine, deazaguanosine, and the like, linked to a pentose at the 1' position, including 2'-deoxy and 2'-hydroxyl forms, e.g., as described in Kornberg and Baker, *DNA Replication,* 2nd Ed. (Freeman, San Francisco, 1992).

The term "nucleotide" as used herein refers to a phosphate ester of a nucleoside, e.g., mono, di and triphosphate esters, wherein the most common site of esterification is the hydroxyl group attached to the C-5 position of the pentose. Nucleosides also include, but are not limited to, synthetic nucleosides having modified base moieties and/or modified sugar moieties, e.g. described generally by Scheit, *Nucleotide Analogs* (John Wiley, N.Y., 1980). Suitable NTPs include both naturally occurring and synthetic nucleotide triphosphates, and are not limited to, ATP, dATP, CTP, dCTP, GTP, dGTP, TTP, dTTP, UTP and dUTP. Preferably, the nucleotide triphosphates used in the methods of the present invention are selected from the group of dATP, dCTP, dGTP, dTTP, dUTP and mixtures thereof.

The term "primer" refers to a linear oligonucleotide, which specifically anneals to a unique polynucleotide sequence and allows for synthesis of the complement of the polynucleotide sequence. In certain aspects, a primer is covalently attached to the template as a hairpin.

The phrase "sequence determination" or "determining a nucleotide sequence" in reference to polynucleotides includes determination of partial as well as full sequence information of the polynucleotide. That is, the term includes sequence comparisons, fingerprinting, and like levels of information about a target polynucleotide, or oligonucleotide, as well as the express identification and ordering of nucleosides, usually each nucleoside, in a target polynucleotide. The term also includes the determination of the identification, ordering, and locations of one, two, or three of the four types of nucleotides within a target polynucleotide.

The term "solid-support" refers to a material in the solid-phase that interacts with reagents in the liquid phase by heterogeneous reactions. Solid-supports can be derivatized with proteins such as enzymes, peptides, oligonucleotides and polynucleotides by covalent or non-covalent bonding through one or more attachment sites, thereby "immobilizing" the protein or nucleic acid to the solid-support.

The phrase "target nucleic acid" or "target polynucleotide" refers to a nucleic acid or polynucleotide whose sequence identity or ordering or location of nucleosides is to be determined using methods described herein.

The phrase "terminal phosphate oxygen" refers to the secondary ionization oxygen atom (pK~6.5) attached to the terminal phosphate atom in a nucleotide phosphate probe.

The phrase "internal phosphate oxygen" refers to the primary ionization oxygen atoms (pK~2) in a nucleotide phosphate probe. An NTP has 3 internal phosphate oxygens (one each on the α, β, and γ-phosphates) plus 1 terminal phosphate oxygen (on the γ-phosphate).

The phrase "single molecule configuration" refers to the ability of the compounds, methods and systems of the present invention to measure single molecular events, such as an array of molecules on a solid support wherein members of the array are present as individual molecules located in a defined location. The members can be the same or different.

II. Compounds

In one embodiment, the present invention provides a charge-switch nucleotide phosphate (NP) probe. The NP probe has a terminal phosphate with a fluorophore moiety attached thereto. The NP probe can be a nucleotide diphosphate or nucleotide triphosphate. Preferably, the charge-switch NP probe is a nucleotide triphosphate. In certain preferred aspects, the nucleoside moiety is modified with adducts to confer positive or negative charge. As explained in detail below, modification can occur at the base, the sugar, the phosphate group, linkers and combinations thereof. Advantageously, by electrically sorting molecules having different charges relative to each other, such as by separating an intact charge switch nucleotide from its cleaved PPi-Dye, the cleaved PPi-Dye (PPi-F) molecules are detected in isolation without interference from unincorporated NP probes (e.g., γ-NP-Dye).

In certain embodiments, the incorporation of an NP probe in the growing complementary strand of nucleic acid results in release of a phosphate detectable moiety. In a preferred embodiment, the detectable moiety is a γ-phosphate label that is cleaved from γ-labeled dNTPs by a polymerase. In a preferred embodiment, γ-labeled-dNTPs having a cationic γ-label exhibit charge-switching behavior, wherein the electric charge of the intact triphosphate (γ-NTP-Dye) is negative while the released PPi-Dye is positive. A skilled artisan will appreciate that when the NTP is positive and the PPi is negative is another preferred embodiment. Thus, the release of the PPi-Dye results in a cleavage-dependent charge alteration to the PPi-fluorophore moiety. In certain aspects, cleavage of pyrophosphate from the nucleoside subtracts charges associated with the nucleoside. These charge changes can be either positive or negative. In certain aspects, the cleavage of the PPi-Dye adds a positive charge to the PPi-Dye moiety by generating a terminal phosphate oxygen, as a terminal phosphate-oxygen binds mono or divalent cations (e.g., $Mg^{++}$, $Mn^{++}$, $K^+$, $Na^+$ and the like) as counter ions, better than an internal phosphate-oxygen.

In certain aspects, the charge-switch NP probes of the present invention have a net positive charge. For example, the base can have an amine attached thereto and this amine can be protonated. Upon cleavage of the base-cation, the PPi-Dye becomes more negative. Conversely, cleavage of a negative-base NP (e.g., a base with a carboxylate, sulfonate, and the like attached thereto) makes the PPi-Dye more positively charged. Cleavage of a neutral-base NTP (natural structure), will have no contribution to the PPi-Dye other than generation of a terminal phosphate oxygen.

A. Charge State

The charge state of the NP probe as well as the released terminal phosphate (e.g., pyrophosphate) are parameters of the compounds of the present invention. Those of skill in the art will appreciate the various parameters making-up or contributing to the charge on the γ-NP-Dye and the terminal phosphate-Dye (e.g., PPi-Dye moiety). In certain aspects, a charge-switch nucleotide phosphate (NP) probe comprises an intact NP probe having a terminal phosphate with a fluorophore moiety attached thereto. The intact NP probe has a first molecular charge associated therewith; and whereupon cleavage of the terminal phosphate such as cleavage of a pyrophosphate fluorophore moiety, the pyrophosphate fluorophore moiety carries a second molecular charge. The first molecular charge is different than the second molecular charge by at least 0.4 as calculated under ionic conditions obtained in pure water, at about pH 7 (see, FIG. 2). The charge difference between the intact NP probe is more preferably between about 1 and about 4, and any fraction of the integers 1, 2, and 3

The charge state of the either the γ-NP-Dye or terminal phosphate-Dye (e.g., PPi-Dye) or both can be determined for any ionic condition by calculating the i) charge on the base; the ii) charge on the fluorophore or linker; and iii) the buffer cation composition and concentration (see, Example I).

In general, the net electric charge on a nucleotide phosphate such as a dNTP, is governed by the base ring nitrogens and by the three phosphates. At a pH from about 6.5 to about 8.5, the bases are mostly uncharged (nitrogen pK of 3–4 and 9.5–10). The primary ionization of each ionizable oxygen atom on each phosphate (pK~2) contributes one full negative charge. The secondary ionization specific to the phosphate oxygen (pK~6.5) contributes a time-averaged charge of –0.9 at pH 7.5 so the total charge on the dNTP is –3.9.

FIG. 1 illustrates a representative compound of the present invention showing an intact γ-NP-Dye and the released pyrophosphate having a detectable moiety. As shown therein, in certain aspects, the nucleobase carries a cationic adduct and the terminal oxygen is replaced by a nitrogen and a label moiety in a γ-dNTP, thus, the secondary ionization is eliminated and at pH 7 ($H_2O$), the charge on a γ-dNTP is –2.0 (for a neutral γ-label). After cleavage from the nucleotide, the charge on the PPi-Dye is –2.74, because it has lost the positive charge (+1) of the nucleobase, but has gained back a partial positive charge (+0.26) due to hydrogen ion equilibration with the terminal phosphate oxygen (pK 6.4 secondary ionization of substituted diphosphates).

FIG. 2 is a look-up table showing various embodiments and charges associated with the nucleobase and dye and their respective net charges under ideal conditions (without associated counter ions or buffers; charged adducts fully charged) or in pure water (last column only). Entry 32 illustrates the preceding example. As tabulated therein, for ideal conditions, the nucleobase has a charge of 1, the dye has a charge of 0 and therefore a net charge of –2 is associated with the γ-NP-Dye and a charge of –3 for the PPi-Dye, giving a charge difference of –1. The charge difference is slightly less (–0.74; last column) in pure water at pH 7, however, because the terminal phosphate oxygen of PPi-F associates more readily with hydrogen ions. As shown therein, various electric charges placed on the nucleobase and the dye will have different effects on the dye upon incorporation of the nucleobase into a growing nucleic acid. The charge difference under ideal conditions is equal to the sum of the opposite of the charge on the nucleobase moiety and the terminal phosphate dye moiety, as the nucleobase is separated from the dye when the nucleobase is incorporated into DNA. The charge difference in pure water (last column) takes into account hydrogen ion equilibrium binding.

In certain other embodiments, the charge-switch NP probes of the present invention have various counter ions associated with them (e.g., $Mg^{++}$ or other cations). For example, $Mg^{++}$ binds to phosphate groups in a variety of coordination isomers that rapidly equilibrate at $10^3$ to $10^5$ $sec^{-1}$. $Mg^{++}$ ions, like protons, bind more tightly to terminal phosphates than to "internal" phosphates, meaning that a PPi-Dye moiety acquires more positive charge from the counter ions than a γ-dNTP-Dye. In operation, this difference is utilized to sort or separate the released PPi-Dye from the intact γ-NTP-Dyes in for example, a microchannel system using the compounds, methods and systems of the present invention.

As explained in more detail below, the magnitude of a charge-switch can be enhanced by attaching positive or negative charged groups to the nucleoside (normally neutral at pH 7.5). The range of the charge-switch can be set by attaching charged groups to the γ-phosphate label, either on the fluorophore and/or linker, such that both the NP probe and the PPi-F are negatively charged, or both are positively charged, or one is negative while the other is positive. All such combinations and permutations are encompassed by the present invention. Thereafter, when the base is incorporated into DNA, the charged group is separated from the PPi-F to enhance the "natural" counter ion (e.g., $Mg^{++}$) dependent charge effect.

There are 10 charge-switch modes that can be exploited for sorting (neg to weak neg, neg to strong negative, neg to zero, neg to pos, zero to neg, zero to pos, pos to neg, pos to zero, weak to strong pos and strong to weak pos). The two "bipolar" modes, i.e., negative to positive, positive to negative are preferred for electrosorting, although the other modes can also be used under appropriate microfluidic conditions. Other preferred compounds from FIG. 2 are set forth in Table 1.

TABLE 1

| Compound | Charges |
|---|---|
| 20 | N(−1) F(+2) |
| 13 | N(−2) F(+2) |
| 12 | N(−2) F(+1) |
| 40 | N(+2) F(+1) |
| 39 | N(+2) F(0) |
| 19 | N(−1) F(+1) |
| 27 | N(0) F(+2) |
| 33 | N(+1) F(+1) |
| 26 | N(0) F(+1) |
| 41 | N(+2) F(+2) |

Figure 3:
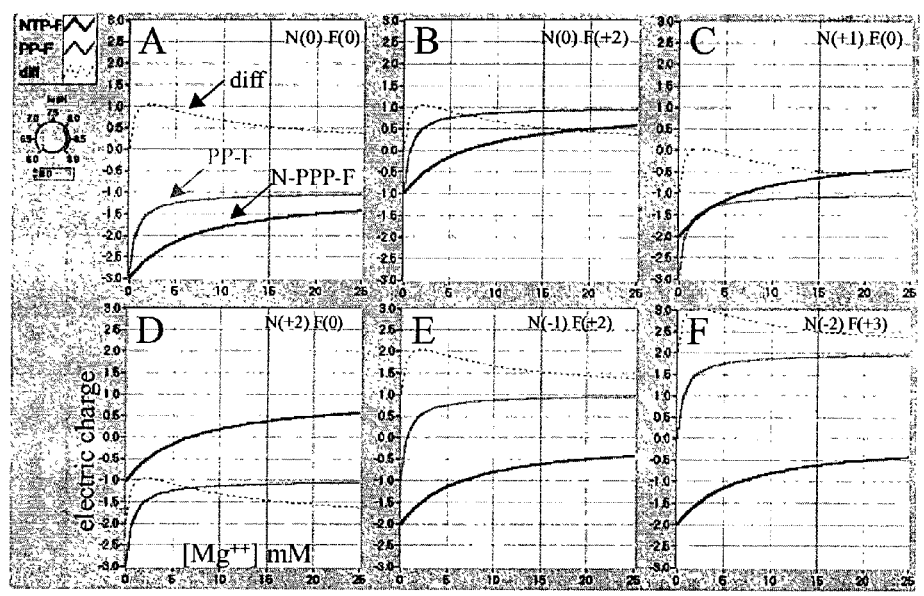
FIGS. 3(A–F) illustrates schematically equilibrium calculations showing the effect of $Mg^{++}$ on the time-averaged electric charge on the "ligands" N-PPP-F and PP-F (N=nucleotide, PPP=triphosphate, PP=pyrophosphate, F=γ-label). Binding to the ions $H^+$ and $Mg^{++}$ are considered. The fraction of ligand bound to an ion, fracBound, is given as fracBound=[ion]/([ion]+K), where K is the ion concentration giving fracBound=50% (i.e., the association or dissociation constant). The fractions of N-PPP-F and PP-F in protonated form were calculated according to the above eqn. Then, the fraction bound to $Mg^{++}$ was calculated for both the protonated and unprotonated forms of N-PPP-F and PP-F. The average charge was then calculated by multiplying the fraction of each form by its respective charge and adding all of the forms of the molecule. Results are plotted as a function of $Mg^{++}$ concentration (0–25 mM). Charges on N and F were modeled as pH-independent quaternary salts (+) or carboxylates (−) PANEL A N(0) F(0), PANEL B N(0) F(2), PANEL C N10) F(0), PANEL D N(2) F(0), PANEL E N(−1) F(2), PANEL E N(−2) F(3)

In order to obtain a bipolar mode, the γ-dNTP is "poised" with respect to charge so that the charge switch "passes through" neutral. FIGS. 3(A–F) illustrate how the counter ion concentration (e.g., $Mg^{++}$ ion) affects the charge of a generic γ-nucleotide (N-PPP-F) and a cleavage product (PP-F). Six different charge configurations "N(b) F(g)" are shown (A–F) wherein b and g are the charge on the nucleoside or γ-label, respectively. The charged groups (having different pK's) can be for example, primary or quaternary amines which add positive charge (+), or a carboxylic acid, which adds negative charge (−) and the like. With no added groups N(0) F(0) (Panel A), the maximum charge switch at pH 8 (Δq=+1) occurs at about 2 mM $Mg^{++}$, with the change being in negative range (−2.5 to −1.5). By adding a charge of (+2) to the γ-label (Panel B), the same switch magnitude is obtained (Δq=+1), except now the shift is a bipolar mode wherein the γ-dNTP-F and PPi-F are oppositely charged (−0.5 to +0.5). Other configurations in FIGS. 3(C–F) show how the charge switch magnitude can be further increased (to facilitate electrosorting) by adding various charges to the nucleobase and/or γ-label. As is apparent from FIG. 3, the charge difference (Δq) can occur in negative range, positive range, negative to positive range or positive to negative range.

Figure 4:
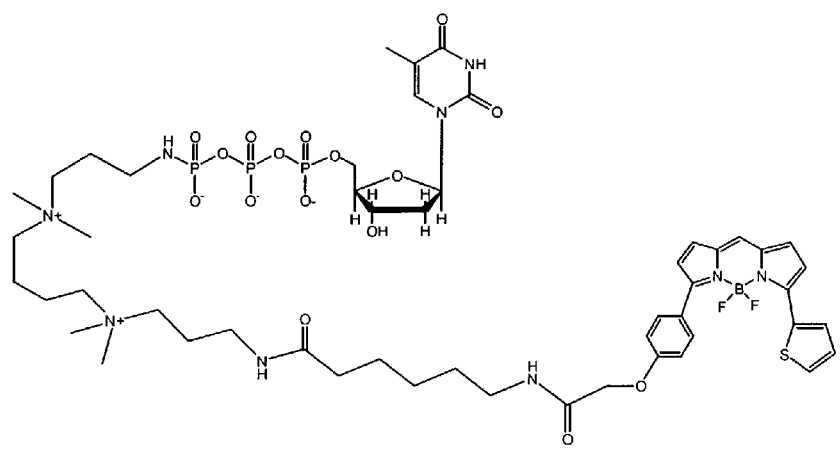
FIG. 4 illustrates a compound of the present invention (dTTP-BQS-BTR)

As exemplified in FIG. 4, the charge difference between the intact NP probes and the detectable moieties can be introduced via a charged linker fixed to the γ-label such that, the γ-NTP-Dye is net negative, while the PPi-Dye is net positive. As shown therein, the electroneutral dye BODIPY®TR is conjugated to dTTP using a linker having a charge of +2. This nucleotide can be incorporated into DNA by a polymerase, with the release of phosphate, thus the PPi-Linker-Dye moiety acquires a more positive charge than the intact γ-NTP-Dye. In one embodiment, polymerases as disclosed in U.S. patent application Ser. No. 10/131,998, filed Apr. 24, 2002, and incorporated herein by reference, are used.

Using the equations set forth in Example I below, and with reference to FIG. 5, it is possible to calculate the net charge on the γ-NP-Dye and the released terminal phosphate (e.g., PPi-Dye) in the presence and absence of a metal counter ion. In certain instances, equilibrium association of cations to the compounds of the present invention will add about 1 positive charge to Δq, depending on the cation composition, concentration and pH (see, FIG. 3).

Figure 5:
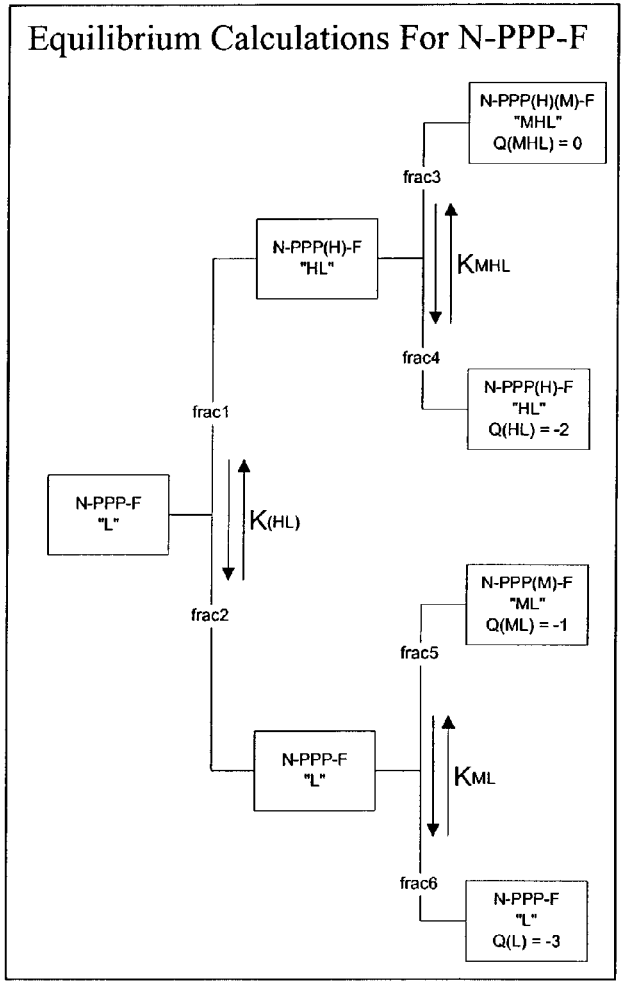
FIG. 5 illustrates a schematic of equilibrium calculations of the present invention (see, Example I)

The determination of charge on each moiety can be carried out using the equilibrium calculations in Example I below and as illustrated in FIG. 5. Using the equilibrium equations, Example I sets forth the charge determination of the compound in FIG. 4.

FIGS. 6(A–D) illustrates various charge-switch nucleotides of the present invention. These compounds are merely an illustration and should not limit the scope of the claims herein. One of ordinary skill in the art will recognize other variations, modifications, and alternatives.

In certain aspects, the present invention provides a charge-switch nucleotide phosphate (NP) probe. The NP probe has a terminal phosphate with a fluorophore moiety attached thereto, wherein the intact NP probe has a first molecular charge associated therewith, and upon cleavage of the fluorophore moiety having a phosphate or pyrophosphate group appended thereto, the P-F or PPi-F has a second charge. The first charge and second charge are different. Formula I provides charge-switch nucleotide phosphate probes of the present invention:

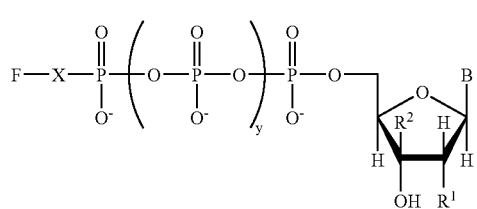

I

In Formula I, B is a nucleobase including, but not limited to, naturally occurring or synthetic purine or pyrimidine heterocyclic bases, including but not limited to adenine, guanine, cytosine, thymine, uracil, 5-methylcytosine, hypoxanthine or 2-aminoadenine. Other such heterocyclic bases include 2-methylpurine, 2,6-diaminopurine, 6-mercaptopurine, 2,6-dimercaptopurine, 2-amino-6-mercaptopurine, 5-methylcytosine, 4-amino-2-mercaptopyrimidine, 2,4-dimercaptopyrimidine and 5-fluorocytosine. Representative heterocyclic bases are disclosed in U.S. Pat. No. 3,687,808 (Merigan, et al.), which is incorporated herein by reference.

In certain preferred aspects, B comprises a charged moiety. These charged base-moieties can be positively or negatively charged. Using a charged base-moiety, it is possible to impart additional charge onto the base or the intact γ-dNTP-F. Suitable charged base linking groups can append carboxylic acid group, sulfonic acid group, and the like.

$R^1$ in Formula I is a hydrogen, a hydroxyl group or charged group e.g., $L\text{-}SO_3^-$, $L\text{-}NH_3^+$, $L\text{-}CO_2^-$ and the like; wherein L is a linker.

$R^2$ in Formula I is a hydrogen, or charged group e.g., $L-SO_3^-$, $L-NH_3^+$, $L-CO_2^-$ and the like; wherein L is a linker.

In Formula I, X is a heteroatom such as nitrogen, oxygen, and sulfur. Preferably, X is nitrogen. As the NP probes of the present invention can be tetraphosphates, triphosphates or diphosphates, the index "y" in Formula I, can be 0, 1 or 3.

In Formula I, F is a fluorophore or dye. In certain preferred aspects, F comprises a charged label linker group. Using the charged label linking group, it possible to impart additional charge onto the fluorophore moiety (i.e., the cleaved PPi-F or P-F). Suitable charged label-linking groups can append quaternary nitrogens and the like. The compounds of Formula I can have counter ions associated therewith. These counter ions include mono and divalent metal ions including, but are not limited to, $Mg^{++}$, $Mn^{++}$, $K^+$ and $Na^+$. Those of skill in the art will know of additional counter ions suitable for use in the present invention. FIGS. 6(A–D) set forth preferred compounds of the present invention.

B. Labels

Many dyes or labels are suitable for charge-switch nucleotide phosphates of the present invention. In fact, there is a great deal of practical guidance available in the literature for providing an exhaustive list of fluorescent and chromogenic molecules and their relevant optical properties (see, for example, Berlman, *Handbook of Fluorescence Spectra of Aromatic Molecules*, 2nd Edition (Academic Press, New York, 1971); Griffiths, *Colour and Constitution of Organic Molecules* (Academic Press, New York, 1976); Bishop, Ed., Indicators (Pergamon Press, Oxford, 1972); Haugland, *Handbook of Fluorescent Probes* and *Research Chemicals* (Molecular Probes, Eugene, 1992) Pringsheim, *Fluorescence and Phosphorescence* (Interscience Publishers, New York, 1949); and the like. Further, there is extensive guidance in the literature for derivatizing fluorophore molecules for covalent attachment via common reactive groups that can be added to a nucleotide, as exemplified by the following references: U.S. Pat. No. 3,996,345; Khanna et al., and U.S. Pat. No. 4,351,760.

In certain preferred aspects, suitable dyes include, but are not limited to, coumarin dyes, xanthene dyes, resorufins, cyanine dyes, difluoroboradiazaindacene dyes (BODIPY), ALEXA dyes, indoles, bimanes, isoindoles, dansyl dyes, naphthalimides, phthalimides, xanthenes, lanthanide dyes, rhodamines and fluoresceins. In certain embodiments, certain visible and near IR dyes are known to be sufficiently fluorescent and photostable to be detected as single molecules. In this aspect the visible dye, BODIPY R6G (525/545), and a larger dye, LI-COR's near-infrared dye, IRD-38 (780/810) can be detected with single-molecule sensitivity and are used to practice the present invention.

In certain preferred aspects, suitable dyes include, but are not limited to, fluorescein, 5-carboxyfluorescein (FAM), rhodamine, 5-(2'-aminoethyl) aminonapthalene-1-sulfonic acid (EDANS), anthranilamide, coumarin, terbium chelate derivatives, Reactive Red 4, BODIPY dyes and cyanine dyes.

In certain aspects, the phosphate detectable moiety is a charged group. As explained below, Schemes 1–6 in FIG. 6E sets forth aliphatic linkers for γ-phosphate conjugation. In certain aspects, the linkers in Schemes 1–6 can be used without further attachment of a label such as a fluorophore. The linkers themselves can be used as the phosphate detectable moieties.

C. Linkers to the Label

There are many linking moieties and methodologies for attaching fluorophore moieties to nucleotides, as exemplified by the following references: Eckstein, editor, *Oligonucleotides and Analogues: A Practical Approach* (IRL Press, Oxford, 1991); Zuckerman et al., *Nucleic Acids Research*, 15: 5305–5321 (1987) (3' thiol group on oligonucleotide); Sharma et al., *Nucleic Acids Research*, 19: 3019 (1991) (3' sulfhydryl); Giusti et al., *PCR Methods and Applications*, 2: 223–227 (1993) and Fung et al., U.S. Pat. No. 4,757,141 (5' phosphoamino group via Aminolink™ II available from Applied Biosystems, Foster City, Calif.) Stabinsky, U.S. Pat. No. 4,739,044 (3' aminoalkylphosphoryl group); AP3 Labeling Technology (U.S. Pat. Nos. 5,047, 519 and 5,151,507, assigned to E.I. DuPont de Nemours & Co); Agrawal et al., *Tetrahedron Letters*, 31: 1543–1546 (1990) (attachment via phosphoramidate linkages); Sproat et al., *Nucleic Acids Research*, 15: 4837 (1987) (5' mercapto group); Nelson et al., *Nucleic Acids Research*, 17: 7187–7194 (1989) (3' amino group); and the like.

In certain aspects, the fluorophore moiety is a fluorescent organic dye derivatized for attachment to a γ-phosphate directly or via a linker. In general, nucleotide labeling can be accomplished using any of a large number of known nucleotide labeling techniques using known linkages, linking groups, and associated complementary functionalities. The linkage linking the fluorophore to the phosphate should be compatible with relevant polymerases.

In one embodiment, the linker is an alkylene group, such as a methylene or ethylene group. In this embodiment, the fluorophore linker is an alkylene group having between about 1 to about 50 carbon atoms, preferably about 10 to 30 carbon atoms and more preferably, about 15 to about 25 carbon atoms, optionally interrupted by heteroatom(s). In certain aspects, the linker has at least 1 positive or negative charge associated therewith.

In certain other embodiments, various charged linkers can also be used. Schemes 1–6 in FIG. 6E sets forth aliphatic linkers for γ-phosphate conjugation.

As shown therein, Scheme 1 sets forth a MQS(+) (monoquaternary salt) linker generated using a phthaliamide protecting group. The MQS is thereafter used as a reagent in Schemes 3 and 4. Scheme 2 sets forth a BQS(++) (bisquatemary salt) linker. Scheme 3 sets forth a TQS(+++) (triquaternary salt) linker, which is made by combining one MQS unit with one BQS unit using appropriate stoichiometry. The phthaliamide protecting group is removed when necessary in 1M NaOH for 2 h. In addition, Scheme 4 sets forth a TetQS(++++) (tetraquaternary salt) linker made by combining two MQS units with one BQS unit as shown. Scheme 5 sets forth protection of the aminoally amino group of AA-dUTP, and Scheme 6 sets forth the chemistry to couple the BQS linker to dTTP. The product is purified by HPLC and reacted with the succinimide ester of BodipyTR.

Figure 6B:
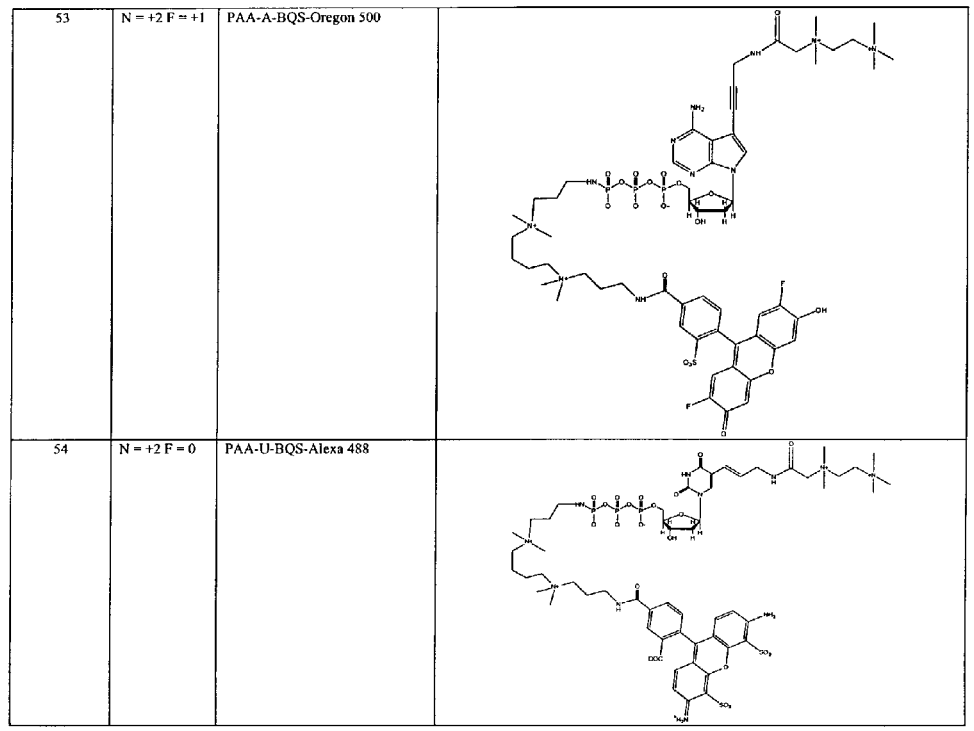
FIG. 6 (A–F) PANEL A compounds of the present invention; PANEL B compounds of the present invention; PANEL C compounds of the present invention; PANEL D compounds of the present invention; PANEL E various linker embodiments used in compounds of the present invention; and PANEL F various linker (SEQ ID NOS:1–3) embodiments used in compounds of the present invention.
Figure 6C:
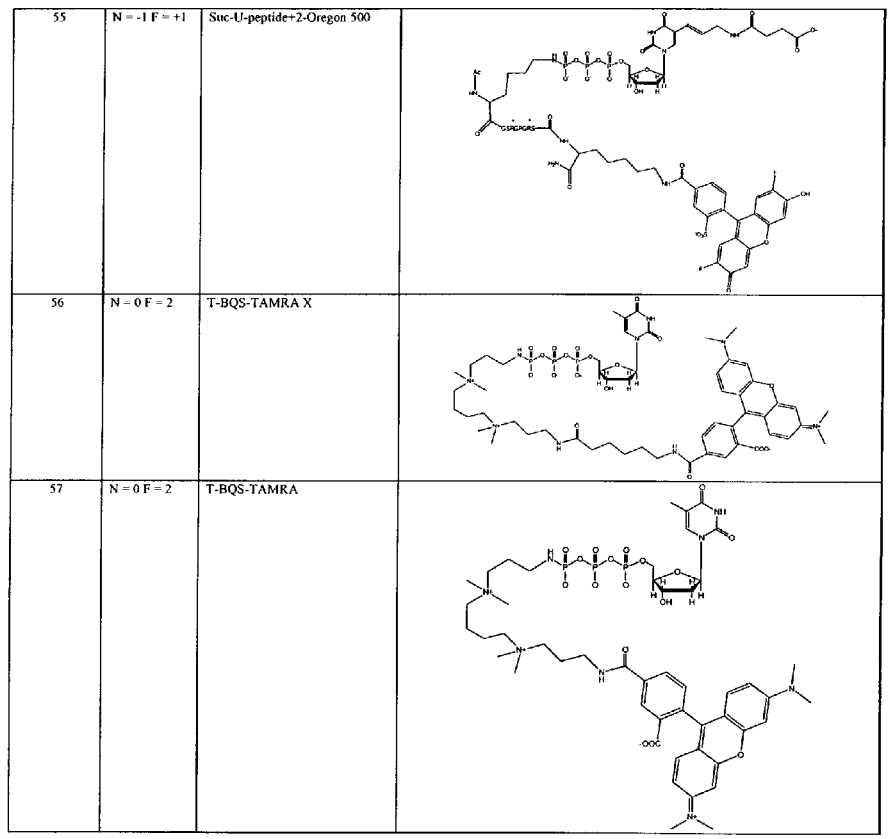
Figure 6D:
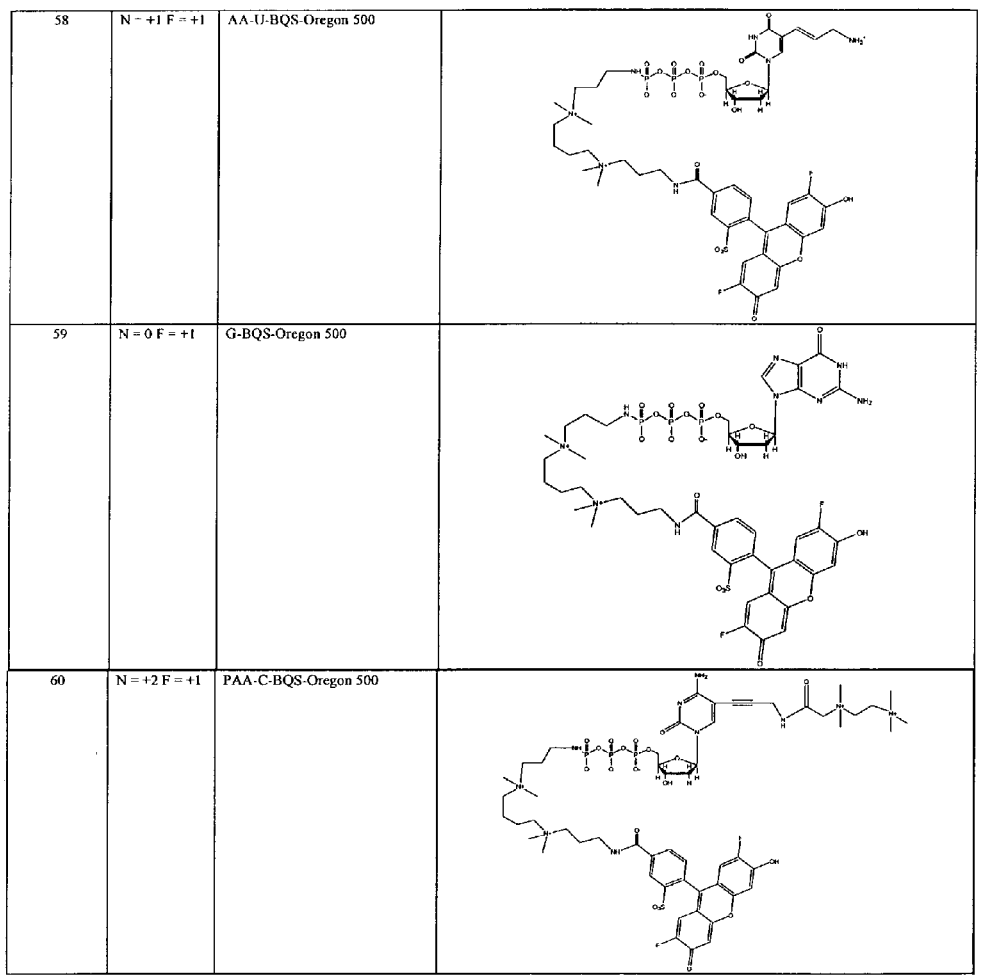
Figure 6E:
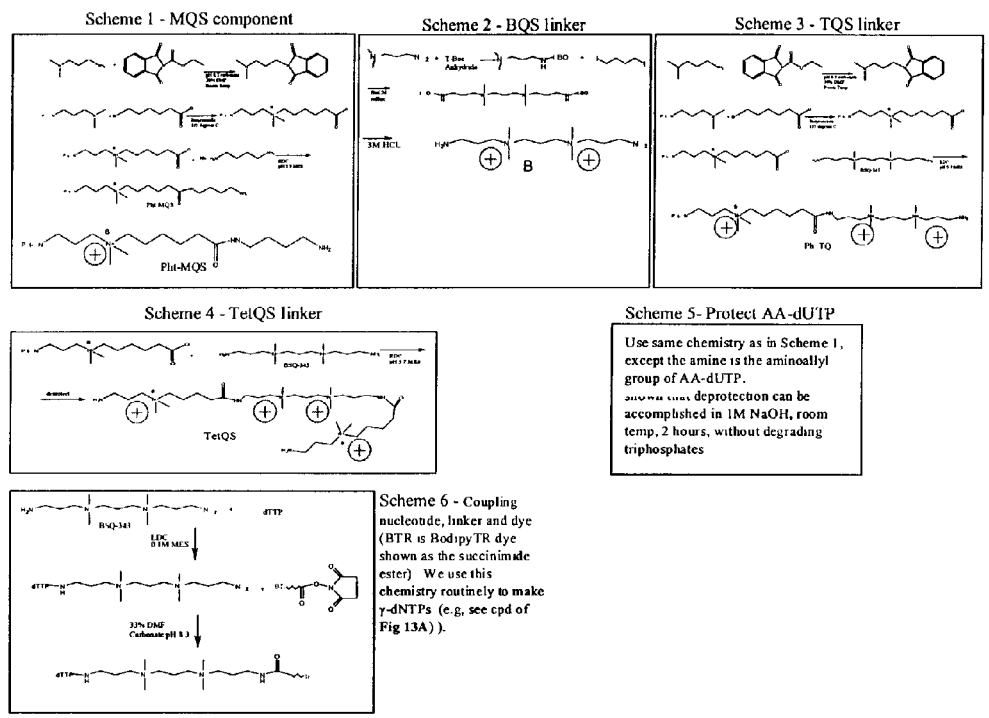

In still other embodiments, FIG. 6F sets forth peptide moieties for linking the fluorophore to the terminal phosphate. Preferably, the peptide is between 2 and 15 amino acids in length. Scheme 7 shows the coupling of 3 lysines (KKK) through their ε-amines so that each residue provides 7 atoms to the linker. The three lysines together form a largely-aliphatic linker 21 atoms long, about the same size as the BQS linker. Both the C and N-termini of the peptide are blocked by amidation or acylation. A reversible protecting group is required to achieve directional coupling. Using a protecting group having the sequence RPTL (SEQ ID NO:3) (C-N direction), it is possible to cleave the peptide linker very specifically by thrombin on the C-terminal side of the arginine (Harris et al., *Proc Nat Acad Sci USA*, 97:7754–7759 (2000)). In addition, Scheme 8 shows the peptides of Scheme 7 being coupled directionally to the γ-P of dNTPs. Additional linkers suitable for use in the present invention will be apparent to those of skill in the art.

D. Charged Moieties on the Base

In certain aspects, the base has a charged moiety appended thereto to increase or decrease molecular charge. In general, attaching one or more nucleotide charged moieties can be accomplished using any of a large number of known nucleotide labeling techniques using known linkages, linking groups, and associated complementary functionalities. Preferably, the linkage attaching the charged moiety and nucleotide should be compatible with relevant polymerases.

Preferably, the charged moieties are covalently linked to the 5-carbon of pyrimidine bases and to the 7-carbon of 7-deazapurine bases. Several suitable base labeling procedures have been reported that can be used with the present invention, e.g. Gibson et al., *Nucleic Acids Research*, 15: 6455–6467 (1987); Gebeyehu et al., *Nucleic Acids Research*, 15: 4513–4535 (1987); Haralambidis et al., *Nucleic Acids Research*, 15: 4856–4876 (1987); Nelson et al., *Nucleosides and Nucleotides*, 5(3) 233–241 (1986); Bergstrom, et al., *JACS*, 111, 374–375 (1989); U.S. Pat. Nos. 4,855,225, 5,231,191, and 5,449,767, each of which is incorporated herein by reference. Preferably, the linkages are acetylenic amido or alkenic amido linkages, the linkage between the charged moiety and the nucleotide base being formed by reacting an activated N-hydroxysuccinimide (NHS) ester of the charged moiety with an alkynylamino- or alkenylamino-derivatized base of a nucleotide.

The synthesis of alkynylamino-derivatized nucleosides is taught by Hobbs et al. in European Patent Application No. 87305844.0; U.S. Pat. Nos. 5,047,519 and 5,151,507, assigned to E.I. DuPont de Nemours & Co; and Hobbs et al., *J. Org. Chem.*, 54: 3420 (1989), which are incorporated herein by reference. As taught therein, the alkynylamino-derivatized nucleotides are formed by placing the appropriate halodeoxynucleoside (usually 5-iodopyrimidine and 7-iodo-7-deazapurine deoxynucleosides and Cu(I) in a flask, flushing with argon to remove air, adding dry DMF, followed by addition of an alkynylamine, triethyl-amine and Pd(0). The reaction mixture can be stirred for several hours, or until thin layer chromatography indicates consumption of the halodeoxynucleoside.

As taught in U.S. Pat. No. 5,047,519, which issued to Hobbs et al. on Sep. 10, 1991, the alkynylamino linkers have the structure:

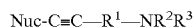

wherein $R^1$ is a substituted or unsubstituted diradical moiety of 1–20 atoms. Nuc is a purine or pyrimidine base. $R^1$ can be straight-chained alkylene, $C_1$–$C_{20}$, optionally containing within the chain double bonds, triple bonds, aryl groups or heteroatoms such as N, O or S. The heteroatoms can be part of such functional groups as ethers, thioethers, esters, amines or amides. Preferably, $R^1$ is straight-chained alkylene, $C_1$–$C_{20}$; most preferably $R^1$ is $CH_2$. Substituents on $R^1$ can include $C_1$–C6 alkyl, aryl, ester, ether, amine, amide or chloro groups. $R^2$ and $R^3$ are independently H, alkyl, $C_1$–$C_4$, or a protecting group such as acyl, alkoxycarbonyl, a charged moiety or sulfonyl. Preferably $R^2$ is H, and $R^3$ is a charged moiety. The alkynylamino linker is preferably attached to the 5-position of the pyrimidine nucleotides and the 7 position of the purine nucleotides.

In still other embodiments, FIG. 6F sets forth methods for carboxylating the aminoally group of AA-dUTP using succinic anhydride (−1) or 1,2,4-benzenetricarboxylic anhydride (−2). This provides negatively charged bases to test the high-magnitude charge-switch configurations. In addition, Scheme 10 shows peptide linkers are used to synthesize the carboxylated γ-dUTPs mentioned in Scheme 9.

In yet another aspect, the charge group is attached to the sugar. Suitable charged groups and their syntheses are disclosed in U.S. Pat. No. 6,191,266 (incorporated herein by reference). The charged groups can be at C-2 or C-3 or combinations thereof.

E. Assay to Assess Charge

Those of skill in the art will readily recognize that various assays are easily implemented to assess the charge of the intact nucleotide phosphate and the cleaved pyrophosphate carrying a label. The following assay is just one of many available assays to calculate and assess the net charge on the γ-NP-Dye and the released PPi-F or P-F moiety.

In certain instances, the assay set forth in Example VII is used to test for a change in the electric charge associated with a dye attached to the terminal phosphate of a nucleotide. In one embodiment, the charge switch is caused by cleavage of a phosphodiester bond that links the dye to the nucleotide. In one example, cleavage is catalyzed by snake venom phosphodiesterase. It will be appreciated by those of skill in the art that other enzymes, such as a DNA polymerase listed herein, can also be used to demonstrate charge switching.

As such, in another embodiment, the present invetnion provides a method for identifying an intact charge-switch nucleotide phosphate (NP) probe, comprising: a) contacting a sample comprising the intact charge-switch NP probe with an enzyme to produce a phosphate detectable moiety; and b) applying an electric field to the sample, wherein the phosphate detectable moiety migrates to an electrode differently than the intact charge-switch NP probe.

III. Methods

The charge-switch nucleotide phosphate probes of the present invention can be used in a variety of methods and systems such as methods and systems for sequencing nucleic acid. As described above, in certain aspects, the γ-label is cleaved from γ-dNTPs by various polymerases. In this reaction, the phosphate ester bond between the α and β phosphates of the incorporated nucleotide is cleaved by the DNA polymerase, and the β-γ-diphosphate (pyrophosphate) is released in solution. As used herein, the term pyrophosphate also includes substitution of any of the oxygen atoms of the pyrophosphate group with a nitrogen or a sulfur atom or combinations thereof to generate thiopyrophosphate, dithiopyrophosphate, and the like. Separating the unincorporated γ-NP-Dyes from the PPi-Dye is facilitated when the unincorporated γ-NP-Dyes has a net charge that is different than the released PPi-Dye. For example, a cationic PPi-Dye and a negative intact γ-NP-Dyes (e.g., triphosphate) exhibit charge switching. This characteristic is useful for single-molecule DNA sequencing in a microchannel sorting system for example, where a polymerase-DNA complex is immobilized just upstream from a channel intersection.

A. Separating, Sorting and Sequencing

Figure 7:
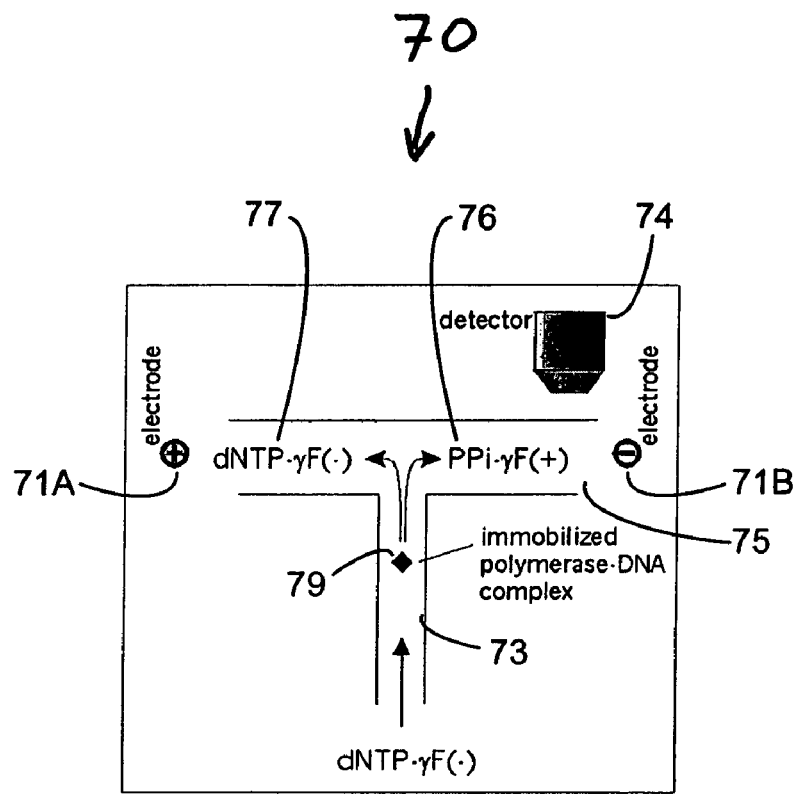
FIG. 7 illustrates a schematic of an embodiment of microfabricated flowcell of the present invention.

FIG. 7 is a schematic of a fabricated flowcell system 70 of the present invention. This diagram is merely an illustration and should not limit the scope of the claims herein. One of ordinary skill in the art will recognize other variations, modifications, and alternatives.

An electric field, created by electrodes 71A and 71B, at the microchannel intersection drives intact γ-dNTP-Dyes into a first microchannel toward the anode 71A, while PPi-Dye molecules are driven toward the cathode 71B into a second channel where they are detected with a detector 74. In operation, each of the 4 dNTPs is labeled with a different dye, enabling real-time sequencing as successive PPi-γ-Dye molecules flow through the detection channel or region 75. By electrically sorting differently-charged molecules in this manner, the cleaved PPi-Dye molecules 76 are detected in isolation without interference from unincorporated γ-dNTP-Dyes 77 and without illuminating the polymerase-DNA complex 79.

In certain aspects, a change in charge sign (e.g., from −1 on the γ-dNTP-Dye to +1 on the PPi-Dye) is utilized to separate the γ-dNTP-Dye from the PPi-Dye. In certain aspects, the γ-dNTP-Dye flows across a polymerase located in channel 73 just upstream from a transverse channel. The γ-dNTP-Dye is hydrolyzed by a polymerase and the liberated PPi-Dye diffuses into the medium and moves towards the transverse channel. A transverse electric field directs the PPi-Dye toward the negative electrode 71B, while the intact γ-dNTP-Dye molecules move toward the positive electrode 71A. Thereafter, the PPi-Dye molecules are detected in the transverse channel. Advantageously, this embodiment reduces or eliminates background from intact γ-dNTP-Dye molecules, thus allowing the use of high γ-dNTP-Dye concentrations to drive the polymerase reaction.

As such, the present invention provides a method for separating a labeled nucleotide phosphate having a detectable moiety from a released charged detectable moiety in a sample stream, comprising: a) immobilizing a nucleic acid complex onto a solid support in a single molecule configuration; b) contacting the complex with a polymerase and a plurality of nucleotide phosphates, wherein at least one of the plurality of nucleotide phosphate has a detectable moiety, wherein the detectable moiety is released as a charged detectable moiety when the NP is incorporated into the primer nucleic acid; and c) applying an electric field to the sample stream, thereby separating the labeled NP from the charged detectable moiety.

In another embodiment, the present invention provides a method for sequencing a target nucleic acid comprising: a) immobilizing a nucleic acid polymerase onto a solid support in a single molecule configuration, wherein the solid support is disposed in a flowcell having an inlet port and an outlet port; b) contacting the solid support with a sample stream comprising a target nucleic acid, a primer nucleic acid and a detectable nucleotide phosphate wherein the sample stream flows through the flowcell; c) applying an energy field to the sample stream; and d) detecting the detectable nucleotide phosphate thereby sequencing the target nucleic acid. Optionally, the primer nucleic acid is attached to the target nucleic acid.

Suitable nucleobases include, but are not limited to, adenine, guanine, cytosine, uracil, thymine, deazaadenine and deazaguanosine. In a preferred embodiment, the NP probes are dNTP probes having charge switch characteristics. In other aspects, the nucleobase is immobilized on a solid support and the sample stream contains a polymerase.

In certain preferred embodiments, the intact NP probe has a first molecular charge associated therewith; and whereupon cleavage of the terminal phosphate as a terminal phosphate fluorophore moiety, the phosphate fluorophore moiety carries a second molecular charge, wherein the difference between the first molecular charge and the second molecular charge is preferably between 1 and 4. The charge-switch characteristics are implemented upon enzymatic cleavage of the terminal phosphate or pyrophosphate group.

In certain aspects, at least two energy fields are used. By using at least two energy fields, the signal/noise discrimination can be enhanced when designed in conjunction with the expected charge on the signal molecule versus the noise molecule. That is, the signal molecule (fluorescent phosphates) responds more strongly to a particular field if its charge magnitude exceeds that of the noise molecule (e.g. unincorporated fluorescently labeled nucleotides), or less strongly if its charge magnitude is less than that of the noise molecule.

Upon incorporation by a polymerase, the dNTP is hydrolyzed as usual and the liberated pyrophosphate-dye moiety diffuses into the surrounding medium. The free dye molecule is fluorescent and its appearance is imaged at video-rate under a microscope. A flowing stream sweeps the dye away from the parent DNA molecule. As the polymerase continues to move along the DNA, the nucleotide sequence is read from the order of released dyes. Sequencing proceeds quickly, as fast as the polymerase progresses along the DNA template.

In another embodiment, the present invention provides a method for separating an intact NP probe from a phosphate detectable moiety, comprising: a) providing a sample comprising an intact NP probe with a detectable moiety attached thereto, whereupon an enzymatic cleavage of the intact NP probe, which produces a phosphate detectable moiety, the phosphate detectable moiety carries a molecular charge which is different than the molecular charge of the intact NP probe; and b) applying an energy field to the sample, thereby separating the phosphate detectable moiety from the intact NP probe.

In still yet another embodiment, the present invention provides a method for sequencing a nucleic acid, comprising: providing a target nucleic acid, a primer strand, a polymerase, and a plurality of NP probes; mixing the target nucleic acid, the primer strand, the polymerase, the plurality of NP probes in a flowcell under conditions permitting target dependent polymerization of the plurality of NP probes, thereby providing a polymerization product; and separating the polymerization product by an energy field in the flowcell to provide a sequence of the target nucleic acid.

In yet another embodiment, the present invention provides a method for sequencing a nucleic acid comprising: providing a target nucleic acid, a polymerase priming moiety, a polymerase, and labeled NPs; mixing the target nucleic acid, the polymerase priming moiety, the polymerase and the labeled NPs under conditions permitting target dependent polymerization of the NPs, such conditions which are capable of providing a time sequence of labeled pyrophosphate products; separating by charge the phosphate detectable moieties products from unpolymerized labeled NPs; and, detecting over time the phosphate detectable moieties to provide a sequence of the target nucleic acid. In certain aspects, the method relates to multi-molecule DNA sequencing, as well as single color (multi-molecule or single-molecule) sequencing where four different NP's (all labeled with the same color) are sequentially introduced to the reaction site. In other aspects, two, three, or four-color sequencing can be used.

B. Detection of Pyrophosphate

In certain other embodiments, the present invention provides a heterogeneous assay for the detection of pyrophosphate. The detection of pyrophosphate is advantageous in a number of biological reactions. For example, in a DNA polymerase reaction, wherein the polymerase selects a single DNA molecule from solution and thereafter incorporates the nucleotide at the 3'-end of a primer strand, the natural consequence of such incorporation is the release of pyrophosphate. If the assay solution comprises the four deoxynucleotide triphosphates, each dNTP labeled with a different color of fluorescent dye attached to the γ-phosphate, it is then possible to sequentially record the activity of the polymerase operating on a target DNA. The nucleotide sequence of the target DNA can thereafter be read directly from the order of released dyes attached to the pyrophosphate.

In other embodiments, the present invention provides methods for detecting and identifying individual fluorogenic NP molecules such as dNTP molecules, as a polymerase incorporates them into a single nucleic acid molecule. In certain aspects, a fluorescent dye is attached to the γ-phosphate. As describe above, charged moieties are attached to the nucleobase to modulate a change in the electric charge associated with the dye upon hydrolysis by a polymerase.

As such, the present invention provides a method for detecting pyrophosphate cleavage, the components of the assay comprising a charge-switch NTP, a target nucleic acid, a primer nucleic acid and a polymerase, the method comprising: (a) flowing the labeled charge-switch nucleotide phosphate (NP) having a γ-phosphate with a fluorophore moiety attached thereto, past an immobilized component selected from the group consisting of the polymerase and the target nucleic acid; (b) incorporating the NP on a primer strand hybridized to the target nucleic acid using an enzyme and releasing the γ-phosphate with the fluorophore moiety attached thereto; and (c) detecting the fluorescent moiety thereby detecting pyrophosphate cleavage. In the methods of the present invention, either the polymerase or the target nucleic acid is attached to a solid phase, such as a solid support. Preferably, in the methods of the present invention, the nucleic acid is immobilized on a solid support.

In many of the embodiments herein, the methods of the present invention employ a DNA polymerase such as DNA polymerase I, II or III. In other aspects, suitable polymerases include, but are not limited to, a DNA dependent RNA polymerase and reverse transcriptase such as an HIV reverse transcriptase. Specific examples include, but are not limited to, T7 DNA polymerase, φ29 DNA polymerase, T5 DNA polymerase, *E. Coli* DNA polymerase I, T4 DNA polymerase, T7 RNA polymerase and Taq DNA polymerase. Those of skill in the art will know of other enzymes or polymerases suitable for use in the present invention. In certain aspects, the target nucleic acid is bathed in a flowing solution comprising: polymerase unlabeled, single-stranded DNA fragments hybridized to an oligonucleotide primer and a mixture of NTPs. Optionally, the primer can be attached to the immobilized target nucleic acid.

In certain aspects, detection of the phosphate detectable moiety (e.g., PPi-Dye) is accomplished using an enzyme coupled assay. PPi can be determined by many different methods and a number of enzymatic methods have been described in the literature (Reeves et al., (1969), *Anal. Biochem.*, 28, 282–287; Guillory et al., (1971), *Anal. Biochem.*, 39, 170–180; Johnson et al., (1968), *Anal. Biochem.*, 15, 273; Cook et al., (1978), *Anal. Biochem.* 91, 557–565; and Drake et al., (1979), *Anal. Biochem.* 94, 117–120). Those of skill in the art will know of other enzyme coupled assays suitable for use in the present invention.

In one embodiment, the use of a phosphatase enhances the charge-switch magnitude by dephosphorylating the PPi-F. In certain other aspects, it is preferred to use luciferase and luciferin in combination to identify the release of pyrophosphate since the amount of light generated is substantially proportional to the amount of pyrophosphate released which, in turn, is directly proportional to the amount of base incorporated. The amount of light can readily be estimated by a suitable light sensitive device such as a luminometer.

Luciferin-luciferase reactions to detect the release of PPi are well known in the art. In particular, a method for continuous monitoring of PPi release based on the enzymes ATP sulphurylase and luciferase has been developed by Nyren and Lundin (*Anal. Biochem.*, 151, 504–509, 1985) and termed ELIDA (Enzymatic Luminometric Inorganic Pyrophosphate Detection Assay). The foregoing method may be modified, for example, by the use of a more thermostable luciferase (Kaliyama et al., 1994, *Biosci. Biotech. Biochem.*, 58, 1170–1171). The preferred detection enzymes involved in the PPi detection reaction are thus ATP sulphurylase and luciferase.

Figure 8:
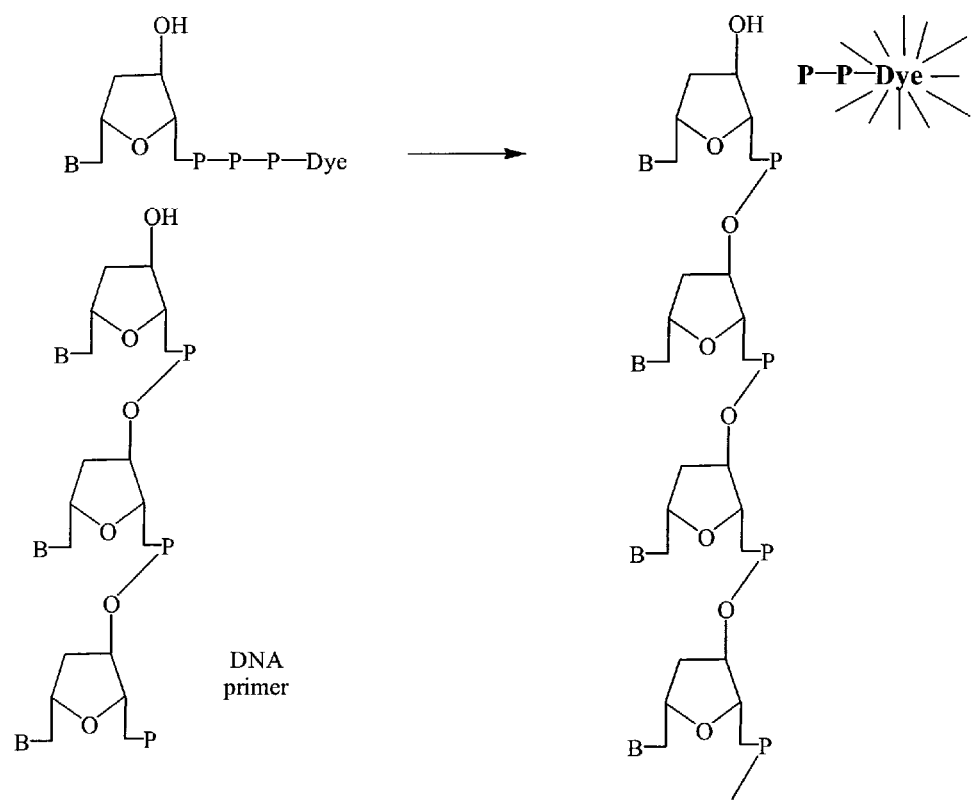
FIG. 8 illustrates a schematic of a method embodiment of the present invention.

As shown in FIG. 8, in preferred compounds of the present invention, wherein a fluorophore is attached to the γ-phosphate, the fluorophore is released from the nucleotide along with the pyrophosphate group. Using single molecule detection for example, fluorescent signals appear at the locations of the individual molecules being observed. In certain aspects, each type of nucleotide is labeled with a different fluorophore so that the incorporated nucleobases can be sequentially identified by the released fluorophores. Preferably, the nucleotide triphosphate (NTP) of the present methods include, but are not limited to, deoxyadenosine triphosphate, deoxycytosine triphosphate, deoxyguanosine triphosphate, deoxythymidine triphosphate, deoxyuridine triphosphate or mixtures thereof, each with a unique fluorophore attached to the γ-phosphate.

In certain embodiments, an unlabeled, single-stranded target nucleic acid with a primer hybridized thereto is tethered to the surface of a solid support such as a glass slide. In another aspect, a double stranded nucleic acid with a nick is tethered. An aqueous solution comprising an enzyme, such as a DNA polymerase, and fluorogenic dNTPs flows across the surface. Alternatively, in another embodiment, an individual polymerase molecule is immobilized on a glass slide and the polymerase is bathed in a flowing solution comprising: 1) unlabeled, single-stranded DNA fragments hybridized to an oligonucleotide primer (or a covalently attached hairpin) and 2) a mixture of deoxynucleotide triphosphates, each uniquely labeled with a different color of fluorescent dye attached to the γ-phosphate.

In certain embodiments, an evanescent light field is set up by total internal refection (TIR) of a laser beam at the glass-aqueous solution interface. In certain aspects, the TIR illumination field is continuously imaged at video-rate with an intensified charge couple device (ICCD) camera.

C. Solid Phase

In certain embodiments herein, the present invention relates to methods wherein a material in the solid-phase interacts with reagents in the liquid phase. In certain aspects, the nucleic acid is attached to the solid phase. The nucleic acid can be in the solid phase such as immobilized on a solid support, through any one of a variety of well-known covalent linkages or non-covalent interactions. In certain aspects, the support is comprised of insoluble materials, such as controlled pore glass, a glass plate or slide, polystyrene, acrylamide gel and activated dextran. In other aspects, the support has a rigid or semi-rigid character, and can be any shape, e.g. spherical, as in beads, rectangular, irregular particles, gels, microspheres, or substantially flat support. In some embodiments, it can be desirable to create an array of physically separate sequencing regions on the support with, for example, wells, raised regions, dimples, pins, trenches, rods, pins, inner or outer walls of cylinders, and the like. Other suitable support materials include, but are not limited to, agarose, polyacrylamide, polystyrene, polyacrylate, hydroxethylmethacrylate, polyamide, polyethylene, polyethyleneoxy, or copolymers and grafts of such. Other embodiments of solid-supports include small particles, non-porous surfaces, addressable arrays, vectors, plasmids, or polynucleotide-immobilizing media.

As used in the methods of the present invention, nucleic acid can be attached to the solid support by covalent bonds, or other affinity interactions, to chemically reactive functionality on the solid-supports. The nucleic acid can be attached to solid-supports at their 3', 5', sugar, or nucleobase sites. In certain embodiments, the 3' site for attachment via a linker to the support is preferred due to the many options available for stable or selectively cleavable linkers. Immobilization is preferably accomplished by a covalent linkage between the support and the nucleic acid. The linkage unit, or linker, is designed to be stable and facilitate accessibility of the immobilized nucleic acid to its sequence complement. Alternatively, non-covalent linkages such as between biotin and avidin or streptavidin are useful. Examples of other functional group linkers include ester, amide, carbamate, urea, sulfonate, ether, and thioester. A 5' or 3' biotinylated nucleotide can be immobilized on avidin or streptavidin bound to a support such as glass.

In other aspects of the methods of the present invention, the polymerase is immobilized on a solid support. Suitable solid supports include, but are not limited to, controlled pore glass, a glass plate or slide, polystyrene, and activated dextran. In other aspects, synthetic organic polymers such as polyacrylamide, polymethacrylate, and polystyrene are also illustrative support surfaces. In addition, polysaccharides such as cellulose and dextran, are further illustrative examples of support surfaces. Other support surfaces such as fibers are also operable.

In other aspects, polymerase immobilization is accomplished using solid chromatography resins that have been modified or activated to include functional groups that permit the covalent coupling of resin to enzyme. Typically, aliphatic linker arms are employed. The enzymes of the present invention can also be noncovalently attached to a solid support surface, through, for example, ionic or hydrophobic mechanisms.

In a preferred embodiment, covalent attachment of a protein or nucleic acid to a glass or metal oxide surface can be accomplished by first activating the surface with an amino silane. DNA or protein derivatized with amine-reactive functional groups can then attach to the surface (see, K. Narasimhan et al., *Enzyme Microb. Technol.* 7, 283 (1985); M. J. Heller et al., U.S. Pat. No. 5,605,662; and A. N. Asanov et al., *Anal. Chem.* 70, 1156 (1998)).

The ordinarily skilled artisan will know numerous other schemes for linking nucleic acid and proteins to support surfaces. Moreover, the choice of support surface and the method of immobilizing the enzyme is largely a matter of convenience and depends on the practitioner's familiarity with, and preference for, various supports surfaces, as well as preference for various immobilizing schemes, and knowledge of the substrate.

In operation, when the enzyme is immobilized, such as a DNA polymerase, the enzyme selects a single DNA molecule from solution. The polymerase incorporates a first nucleotide at the 3'-end of the primer strand. The polymerase then translocates to the next position on the target DNA, incorporates a complementary nucleotide, and releases the respective PPi-Dye. The released dyes move away from the immobilized enzyme in the flowing sample solution. These events can then be recorded sequentially by video-rate imaging using for example, a CCD camera, capable of detecting single fluorophore molecules. The resulting movie shows the activity of a single polymerase molecule operating on a single molecule of DNA. The nucleotide sequence of the DNA target is read directly from the order of released dyes. When the first nucleic acid molecule has been sequenced, the polymerase releases it and selects another template from solution. Many DNA molecules are thereby sequenced by a single polymerase. The process continues for the life of the enzyme.

D. Preparation of Target Nucleic Acid

The target nucleic acid can be prepared by various conventional methods. For example, target nucleic acid can be prepared as inserts of any of the conventional cloning vectors, including those used in conventional DNA sequencing. Extensive guidance for selecting and using appropriate cloning vectors is found in Sambrook et al., *Molecular Cloning: A Laboratory Manual*, Second Edition (Cold Spring Harbor Laboratory, New York, 1989), and like references. Sambrook et al. and Innis et al., editors, PCR Protocols (Academic Press, New York, 1990) also provide guidance for using polymerase chain reactions to prepare target polynucleotides. Cloned or PCR-amplified target nucleic acid is prepared which permit attachment to solid supports.

In a preferred embodiment, sheared DNA fragments from a subject organism, preferably human, are treated to provide blunt ends, then ligated to two oligodeoxynucleotides (ODNs). The first ODN is derivatized with biotin and the second is complementary to a sequencing primer. The ligated DNA is denatured, it is brought into contact with a streptavidin-activated slide, and it attaches through the biotin to the slide. A primer is hybridized to the tethered fragments prior to sequencing. Only DNA fragments having each type of ODN can both attach and be sequenced; fragments having two primer ODNs will not attach, and those having two attachment ODNs will not prime. DNA attachment could also be accomplished by direct covalent coupling as practiced on DNA chips (see, U.S. Pat. No. 5,605,662). Unlike DNA chips that require a dense lawn of probes, preferably, a few DNA molecules are bound per unit surface area. Binding density is easily controlled by adding a carrier to the DNA sample (e.g., free biotin to a biotinylated DNA sample).

The primers (DNA polymerase) or promoters (RNA polymerase) are synthetically made using conventional nucleic acid synthesis technology. The complementary strands of the probes are conveniently synthesized on an automated DNA synthesizer, e.g. an Applied Biosystems, Inc. (Foster City, Calif.) model 392 or 394 DNA/RNA Synthesizer, using standard chemistries, such as phosphoramidite chemistry, e.g. disclosed in the following references: Beaucage and Iyer, *Tetrahedron,* 48: 2223–2311 (1992); Molko et al, U.S. Pat. No. 4,980,460; Koster et al, U.S. Pat. No. 4,725,677; Caruthers et al, U.S. Pat. Nos. 4,415,732; 4,458,066; and 4,973,679; and the like. Alternative chemistries, e.g. resulting in non-natural backbone groups, such as phosphorothioate, phosphoramidate, and the like, may also be employed provided that the resulting oligonucleotides are compatible with the polymerase. They can be ordered commercially from a variety of companies, which specialize in custom oligonucleotides.

Purification of oligonucleotides, where necessary, is typically performed by either native acrylamide gel electrophoresis or by anion-exchange HPLC as described in Pearson and Regnier (1983) *J. Chrom.* 255:137–149. The sequence of the synthetic oligonucleotides can be verified using the chemical degradation method of Maxam and Gilbert (1980) in Grossman and Moldave (eds.) Academic Press, New York, *Methods in Enzymology* 65:499–560.

While primers can hybridize to any of a number of sequences, selecting optimal primers is typically done using computer assisted consideration of available sequences and excluding potential primers which do not have desired hybridization characteristics, and/or including potential primers which meet selected hybridization characteristics. This is done by determining all possible nucleic acid primers, or a subset of all possible primers with selected hybridization properties (e.g., those with a selected length, G:C ratio, uniqueness in the given sequence, and the like.) based upon the known sequence. The selection of the hybridization properties of the primer is dependent on the desired hybridization and discrimination properties of the primer.

One of skill is thoroughly familiar with the theory and practice of nucleic acid hybridization and primer selection. Gait, ed. *Oligonucleotide Synthesis: A Practical Approach*, IRL Press, Oxford (1984); W. H. A. Kuijpers *Nucleic Acids Research* 18(17), 5197 (1994); K. L. Dueholm *J. Org. Chem.* 59, 5767–5773 (1994); S. Agrawal (ed.) Methods in Molecular Biology, volume 20; and Tijssen (1993) Laboratory Techniques in biochemistry and molecular biology-hybridization with nucleic acid probes, e.g., part I chapter 2 "Overview of principles of hybridization and the strategy of nucleic acid probe assays", Elsevier, N.Y. provide a basic guide to nucleic acid hybridization. Innis supra provides an overview of primer selection.

Primers in combination with polymerases are used to sequence target DNA. Primer length is selected to provide for hybridization to complementary template DNA The primers will generally be at least 10 bp in length, usually at least between 15 and 30 bp in length. Primers are designed to hybridize to known internal sites on the subject target DNA. Alternatively, the primers can bind to synthetic oligonucleotide adaptors joined to the ends of target DNA by a ligase. Similarly where promoters are used, they can be internal to the target DNA or ligated as adaptors to the ends.

The reaction mixture for the sequencing comprises an aqueous buffer medium, which is optimized for the particular polymerase. In general, the buffer includes a source of monovalent ions, a source of divalent cations and a buffering agent. Any convenient source of monovalent ions, such as KCl, K-acetate, $NH_4$-acetate, K-glutamate, $NH_4Cl$, ammonium sulfate, and the like may be employed, where the amount of monovalent ion source present in the buffer will typically be present in an amount sufficient to provide for a conductivity in a range from about 500 to 20,000, usually from about 1000 to 10,000, and more usually from about 3,000 to 6,000. A skilled artisan will appreciate that units for conductivity are generally expressed in "Siemens/cm (mhos/cm)" alternatively they can be expressed in microhms and conductance are expressed in "Siemens (mhos)"

The divalent cation may be magnesium, manganese, zinc and the like, where the cation will typically be magnesium. Any convenient source of magnesium cation may be employed, including $MgCl_2$, Mg-acetate, and the like. The amount of Mg ion present in the buffer may range from 0.5 to 20 mM, but will preferably range from about 1 to 12 mM, more preferably from 2 to 10 mM and will ideally be about 5 mM.

Representative buffering agents or salts that may be present in the buffer include Tris, Tricine, HEPES, MOPS and the like, where the amount of buffering agent will typically range from about 5 to 150 mM, usually from about 10 to 100 mM, and more usually from about 20 to 50 mM, where in certain preferred embodiments the buffering agent will be present in an amount sufficient to provide a pH ranging from about 6.0 to 9.5, where most preferred is pH 7.6 at 25° C. Other agents which may be present in the buffer medium include chelating agents, such as EDTA, EGTA and the like.

E. Detection

In certain embodiments, the enzymatic reaction is monitored using single molecule detection. The single-molecule fluorescence detection of the present invention can be practiced using optical setups including near-field microscopy, far-field confocal microscopy, wide-field epi-illumination, and total internal reflection fluorescence (TIRF) microscopy. Suitable photon detectors include, but are not limited to, photodiodes and intensified CCD cameras. In other embodiments, video chips such as CMOS chips can be used. In a preferred embodiment, an intensified charge couple device (ICCD) camera is used. The use of a ICCD camera to image individual fluorescent dye molecules in a fluid near the surface of the glass slide is advantageous for several reasons. With an ICCD optical setup, it is possible to acquire a sequence of images in time (movies) of fluorophores. In certain aspects, each of the NTPs of the present invention has a unique fluorophore associated with it, as such, a four-color instrument can be used having four cameras and up to four excitation lasers or any combination thereof. Thus, it is possible to use this optical setup to sequence DNA. In addition, many different DNA molecules can be imaged and sequenced simultaneously. Moreover, with the use of image analysis algorithms, it is possible to track the path of single dyes and distinguish them from fixed background fluorescence.

In certain aspects, the preferred geometry for ICCD detection of single-molecules is total internal reflectance fluorescence (TIRF) microscopy. In TIRF, a laser beam totally reflects at a glass-water interface. The field does not end abruptly at the reflective interface, but its intensity falls off exponentially with distance as determined by the exponential decay constant of the resulting "evanescent" field. The thin "evanescent" optical field at the interface provides low background and enables the detection of single molecules with signal-to-noise ratios of about 6:1, preferably about 8:1 and more preferably about 12:1 at visible wavelengths (see, M. Tokunaga et al., *Biochem. and Biophys. Res. Comm.* 235, 47 (1997) and P. Ambrose, *Cytometry*, 36, 244 (1999)). In certain aspects, the TIR illumination field is continuously imaged at video-rate with an intensified charge couple device (ICCD) camera. It is thus possible to image the pyrophosphate as it is hydrolyzed by the enzyme, such as after it moves away from the enzyme downstream.

The penetration of the field beyond the glass depends on the wavelength and the laser beam angle of incidence. Deeper penetrance is obtained for longer wavelengths and for smaller angles to the surface normal within the limit of a critical angle. In typical assays, fluorophores are detected within about 200 nm from the surface, which corresponds to the contour length of about 600 base pairs of DNA. Either Prism-type or objective type TIRF geometry is used for single-molecule imaging. (see, X-H. N. Xu et al., *Science*, 281, 1650 (1998) and Tokunaga et al., *Biochem Biophys. Research Comm.*, 235, 47 (1999)).

DNA, proteins and lipids have all been detected in complex samples with single-molecule sensitivity using labeled probes (see, L. Edman et al., *Proc. Natl. Acad. Sci. USA*, 93, 6710 (1996); M. Kinjo et al., *Nucleic Acids Res.* 23, 1795 (1995); A. Castro and J. G. K. Williams, *Anal. Chem.* 69, 3915 (1997); S. Nie, et al., *Science* 266, 1018 (1994); S. Nie, et al., *Anal. Chem.* 67, 2849 (1995); and T. Schmidt et al., *Proc. Natl. Acad. Sci. USA* 9, 2926 (1996)). In addition to simple detection, single fluorophores are also characterized with respect to fluorescence lifetime, spectral shifts and rotational orientation. In a preferred aspect of the present invention, an aqueous solution comprising an enzyme, such as a DNA polymerase, and distinguishable fluorogenic dNTPs, i.e., a characteristic dye for each nucleobase, flows across the surface. An evanescent light field is set up by total internal refection (TIR) of a laser beam at the glass-aqueous solution interface. In certain aspects, the TIR illumination field is continuously imaged at video-rate with an intensified charge couple device (ICCD) camera. It is thus possible to image the pyrophosphate as it is hydrolyzed by the enzyme. The depth of the channel within the detection region detector is preferably between about 0.1 µm and about 1.0 µm. When TIRF detection is used, the depth of the detection region is preferably less than about four times the decay constant of the evanescent excitation field produced in the detection region to ensure that efficient excitation of the fluorophores, liberated phosphate moiety or other detectable product flowing through the detection region.

Upon incorporation by polymerase, the dNTP is hydrolyzed as usual and the liberated terminal phosphate (e.g., pyrophosphate-dye) moiety diffuses into the surrounding medium. The free dye molecule, is imaged at video-rate under a microscope. A flowing stream sweeps the dye away from the parent DNA molecule. As the polymerase continues to move along the DNA, the nucleotide sequence is read from the order of released dyes. Sequencing proceeds quickly, as fast as the polymerase progresses along the DNA template.

In another embodiment, the present invention includes sensors as disclosed in U.S. Pat. No. 5,814,524, which issued to Walt et al., on Sep. 29, 1998. An optical detection and identification system is disclosed therein that includes an optic sensor, an optic sensing apparatus and methodology for detecting and evaluating one or more analytes or ligands of interest, either alone or in mixtures. The system is comprised of a supporting member and an array formed of heterogeneous, semi-selective polymer films which function as sensing receptor units and are able to detect a variety of different analytes and ligands using spectral recognition patterns. Using this system, it is possible to combine viewing and chemical sensing with imaging fiber chemical sensors.

In yet another embodiment, the detection is accomplished using blockade current, as described in U.S. Pat. No. 5,795,782 issued to Church et al., and which is incorporated herein by reference in its entirety for all purposes. As disclosed therein, two pools of medium used may be any fluid that permits adequate analyte mobility for interface interaction. Typically, the pools will be liquids, usually aqueous solutions or other liquids or solutions in which the analyte can be distributed. The interface between the pools is designed to interact sequentially with the analyte molecule one at a time. The useful portion of the interface may be a passage in or through an otherwise impermeable barrier, or it may be an interface between immiscible liquids. It is preferable that only one passage is present or functional in the impermeable barrier. The interface-dependent measurements can be any measurement, e.g., physical or electrical, that varies with analyte-interface interaction. For example, physical changes the analyte cause as they interact sequentially with the interface may be measured. Current changes resulting from the analyte's interference with ion flow at the interface may be measured. The measurements may reflect the sequential interaction of the analyte with the interface, so as to permit evaluation of sequence-dependent characteristics.

In one embodiment, the pools include electrically conductive medium, which can be of the same or different compositions. The pools with conducting media are separated by an impermeable barrier containing an ion-permeable passage, and measurements of the interface characteristics include establishing an electrical potential between the two pools such that ionic current can flow across the ion permeable passage. When the analyte interacts sequentially with the interface at the ion permeable passage, the ionic conductance of the passage will change (e.g., decrease or increase) as each analyte interacts.

The conducting medium used can be any medium, preferably a solution, more preferably an aqueous solution, which is able to carry electrical current. Such solutions generally contain ions as the current conducting agents, e.g., sodium, potassium, chloride, calcium, cesium, barium, sulfate, and phosphate. Conductance (g) across the pore or channel is determined by measuring the flow of current across the pore or channel via the conducting medium. A voltage difference can be imposed across the barrier between the pools by conventional means, e.g., via a voltage source, which injects or administers current to at least one of the pools to establish a potential difference. Alternatively, an electrochemical gradient may be established by a difference in the ionic composition of the two pools, either with different ions in each pool, or different concentrations of at least one of the ions in the solutions or media of the pools. In this embodiment of the invention, conductance changes are measured and are indicative of analyte-dependent characteristics.

F. High Throughput Screening

The present invention also provides integrated systems for high-throughput screening of DNA sequencing and pyrophosphate detection. The systems typically include robotic armature, which transfers fluid from a source to a destination, a controller that controls the robotic armature, an ICCD camera, a data storage unit which records the detection, and an assay component such as a microtiter dish or a substrate comprising a fixed reactant. A number of robotic fluid transfer systems are available, or can easily be made from existing components. For example, a Zymate XP (Zymark Corporation; Hopkinton, Mass.) automated robot using a Microlab 2200 (Hamilton; Reno, Nev.) pipetting station can be used to transfer parallel samples to set up several parallel simultaneous polymerase reactions.

Optical images viewed (and, optionally, recorded) by a camera or other recording device (e.g., a photodiode and data storage device) are optionally further processed in any of the embodiments herein, e.g., by digitizing the image and storing and analyzing the image on a computer. A variety of commercially available peripheral equipment and software is available for digitizing, storing and analyzing a digitized video or digitized optical image. In certain aspects, the integrated system of the present invention carries light from the specimen field to the charge-coupled device (CCD)

camera, which includes an array of picture elements (pixels). The light from the specimen is imaged on the CCD camera. Particular pixels corresponding to regions of the specimen (e.g., individual polymerase sites on a glass surface) are sampled to obtain light intensity readings for each position. Multiple pixels are processed in parallel to increase speed. The apparatus and methods of the invention are easily used for viewing any sample, e.g., by fluorescent or dark field microscopic techniques.

IV. Systems

Figure 9:
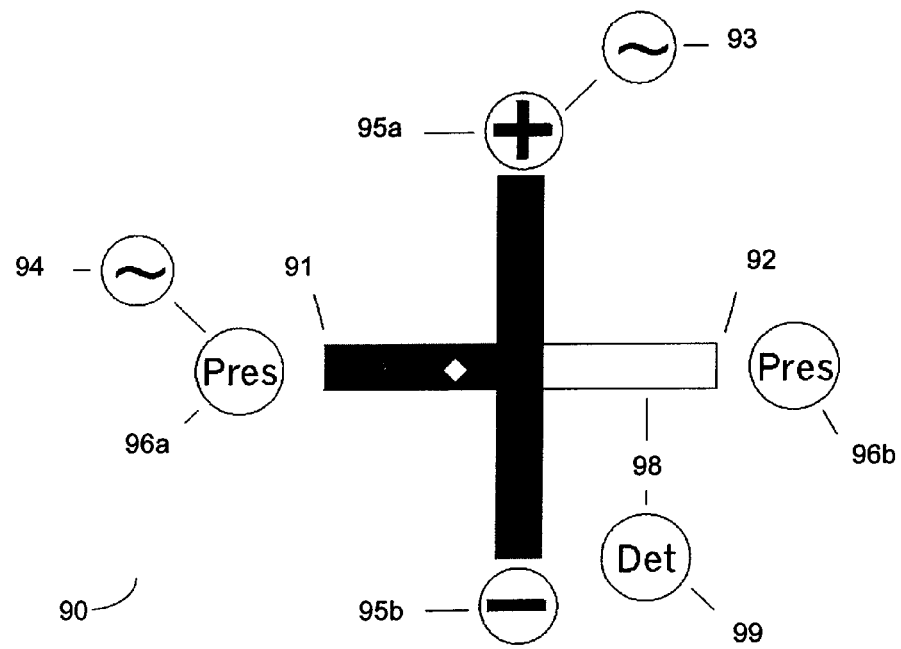
FIG. 9 illustrates a schematic of an embodiment of microfabricated flowcell of the present invention.

FIG. 9 is a schematic of a microfabricated flowcell system 90 of the present invention. This diagram is merely an illustration and should not limit the scope of the claims herein. One of ordinary skill in the art will recognize other variations, modifications, and alternatives.

As shown therein, the present invention provides a microfabricated flowcell 90 having an inlet port 91 and an outlet port 92 wherein a sample stream having a detectable analyte flows therethrough. In certain aspects, the system includes at least a first energy field source 93 that induces an energy field transverse to the sample stream. In some embodiments, the system comprises a second energy field source 94 that induces a second energy field axial to the sample stream. In one embodiment, the first energy field source includes a pair of electrodes 95a, 95b and optionally, the second energy field source includes a hydrostatic pressure generating mechanism 96a, 96b. The system also includes a detector 99 for detecting the analyte in a microchannel zone 98. Suitable energy fields include, but are not limited to, an electric field, a thermal field, a magnetic field, an electromagnetic field, a photoelectric field, a light field, a mechanical field, a pressure field or combinations thereof. Preferably electric and pressure fields are employed.

In certain embodiments, the flowcell is fabricated by microfabrication methods known to those of skill in the art. For example, precision injection molded plastics or molded elastomers can also be used for fabrication. The flowchamber can be made of plastic or glass and should either be open or transparent in the plane viewed by the detector, microscope or optical reader.

In one embodiment, the flowcell is about 0.1 mm to about 100 cm in length, preferably about 1 mm to about 10 cm in length. In certain aspects, the flowcell has channels for the sample stream that can be of different dimensions and are typically between about 0.5 cm and about 10 cm in length and have a depth of between about 0.1 to about 100 μm. Channel dimensions can vary from place to place within the same flowcell. The shape (e.g., cross-sectional geometry) of the channels can vary and can be rectangular, oval, circular, triangular, trapezoidal or otherwise. In certain aspects, various channel shapes are present. The width of each channel is typically about 1 μm to about 100 μm.

In certain embodiments, the system may also include an analyte stream introduced into the inlet port 91 comprising a liquid carrier containing substrate particles, nucleotides, enzymes, and the like. In certain embodiments, the analyte is immobilized on a solid support such as a bead, and the bead may be trapped on a feature in the microchannel. For example, the microchannel may narrow at a point such that a bead or other structure is trapped, or a magnetic field generating element such as magnet may be used to trap a magnetic or magnetizable bead. In the later case, a permanent magnet or set of one or more electric coils may be positioned proximal the trap region. The liquid carrier can be any fluid capable of accepting particles from a feed stream and containing an indicator substance. Preferred sample streams comprise water and solutions such as salt water with buffered solution well known to those of skill in the art. Alternatively, various organic solvents are suitable such as acetone, isopropyl alcohol, ethanol, or any other liquid convenient that does not interfere with detection.

As disclosed in PCT publication No. WO 00/36152 and incorporated herein by reference, in a preferred embodiment, each nucleotide has a unique fluorophore associated with it, as such, a four-color instrument can be used having four cameras and four excitation lasers, or one camera with an image splitter device, or less than four excitation lasers as sufficient to excite the four different dyes. Thus, it is possible to use this optical setup to sequence DNA. In addition, many different DNA molecules immobilized in microchannels can be imaged and sequenced simultaneously. Moreover, with the use of image analysis algorithms, it is possible to track the path of single dyes and distinguish them from fixed background fluorescence.

In an alternative embodiment, the nucleotides disclosed in U.S. Pat. No. 6,232,075, issued Mar. 15, 2001 to Williams, and which is incorporated herein by reference in its entirety for all purposes, can be used. As disclosed therein, nucleotide probes having fluorescent labels attached thereto are disclosed.

In certain other embodiments, detection and analysis is done by various methods known to the art, including optical means, such as optical spectroscopy, and other means such as absorption spectroscopy, Raman spectroscopy or fluorescence, by chemical indicators which change color or other properties when exposed to the analyte, by immunological means, electrical means, e.g., electrodes inserted into the device, capacitance detection means, electrochemical means, blockade current means, radioactive means, or virtually any microanalytical technique known to the art to detect the presence of an analyte such as an ion, molecule, polymer, virus, nucleic acid sequence, antigen, microorganism, and the like. Preferably optical or fluorescent means are used, and antibodies, nucleotides and the like are attached to fluorescent markers.

In certain other embodiments, the flowcell system of the present invention further optionally comprises voltage probes, conductivity electrodes, pH cells, conductivity meters, pH meters, ammeters, voltmeters, flowrate monitors, a data acquisition system and a microcomputer. Those of skill in the art will recognize useful additional sensors and probes.

Figure 10:
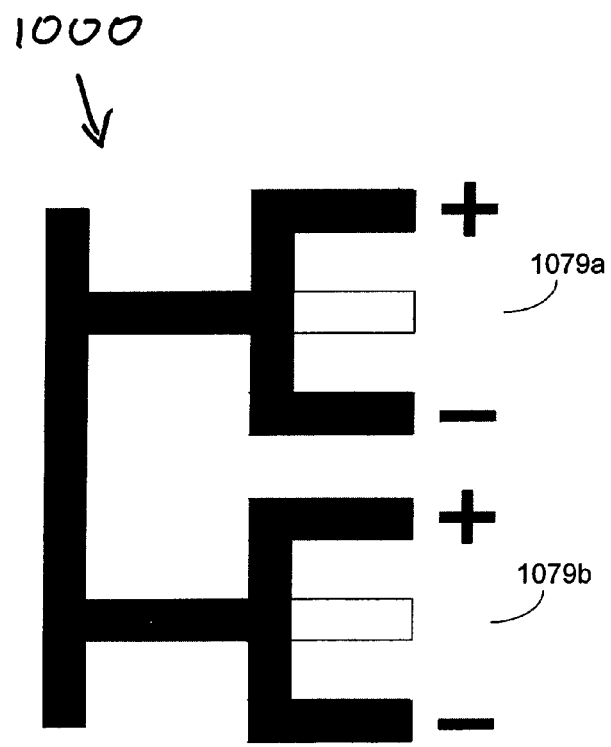
FIG. 10 illustrates a schematic of an embodiment of microfabricated flowcell of the present invention.

FIG. 10 is a schematic of a microfabricated flowcell system of the present invention having a plurality of flowcells (an array of flowcells). This diagram is merely an illustration and should not limit the scope of the claims herein. One of ordinary skill in the art will recognize other variations, modifications, and alternatives.

In this embodiment, the flowcell system 1000 of the present invention is extended into an array of flowcells 1079a, 1079b with a plurality of components. As used herein array is at least two flowcells. For instance, it is possible to have multiple immobilization sites, inlet and outlet ports, detectors and the like.

Figure 13:
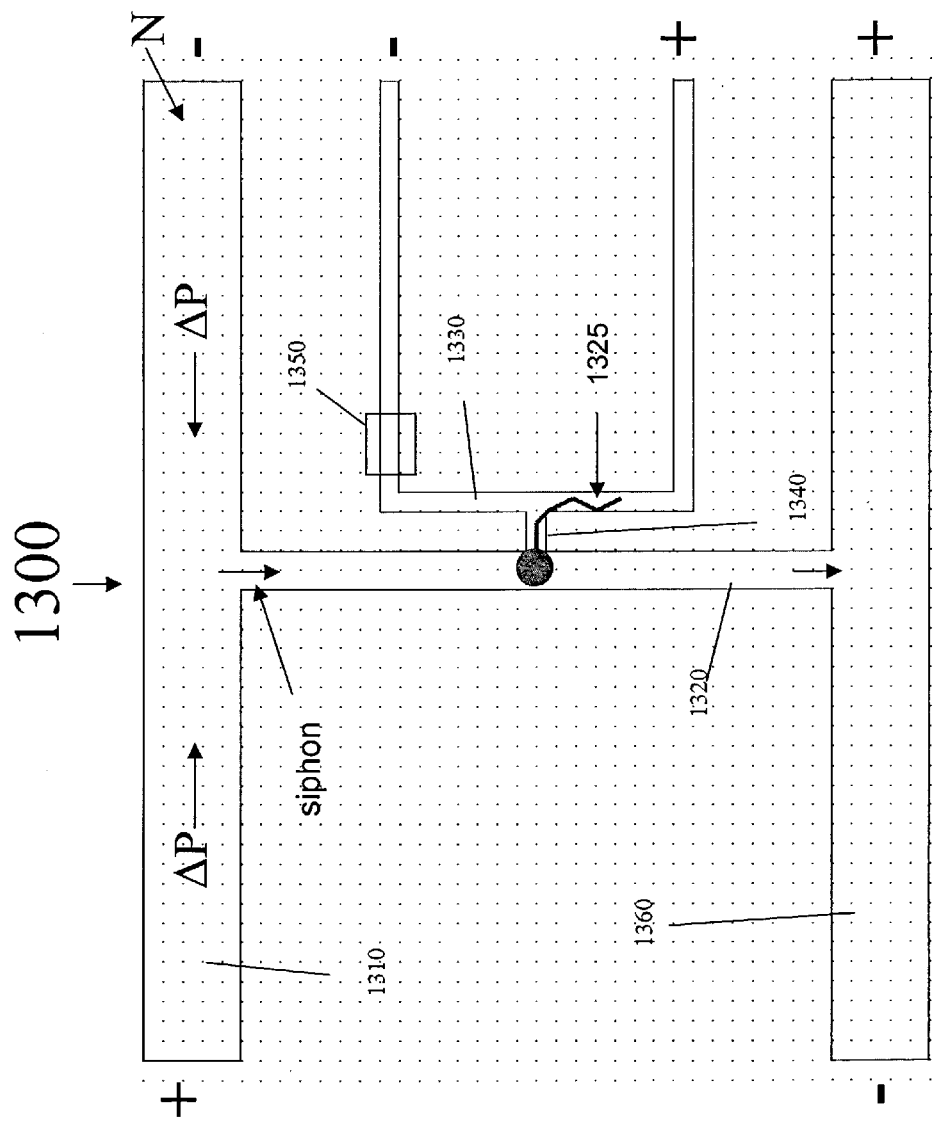
FIG. 13 illustrates a schematic of an embodiment of microfabricated flowcell of the present invention.

FIG. 13 illustrates a flowcell 1300 as viewed from above according to another embodiment of the present invention. Flowcell 1300 is optimally configured as will be described below to provide purification enhancement in the reaction zone and feedback features. As shown in FIG. 13, flowcell 1300 includes a purification microchannel 1310 fluidly coupled to a sample feed microchannel 1320, which in turn is fluidly coupled to a recycle channel 1360. A combination of balanced electric fields and pressure fields are set up to control the flow of analytes (e.g., beads, nucleotides, enzymes, reactants, etc.) introduced into purification channel 1310 to move into feed channel 1320. As shown, electrodes are provided at opposite ends of purification microcharinel 1310 to induce an electric field therebetween. The electrodes are represented as "+" and "−" on FIG. 13 to represent different polarities, although it is understood that one electrode could be at a positive or negative potential and the other held at ground potential. By virtue of the induced electric field in channel 1310, charged material within the channel moves substantially axially along the channel. For example, charge switched nucleotides having a net negative charge will move toward the "+" electrode (anode).

In a preferred embodiment, a pressure field convergent upon the inlet to feed channel 1320 is induced using a pressure generating mechanism(s) (not shown) at the ends of purification channel 1310. Such pressure generating mechanisms include controllable micropumps, regulated compressed nitrogen, compressed air, and the like, as are well known. The arrows entering microchannel 1320 from microchannel 1310 and leaving microchannel 1320 into microchannel 1360 represent such a pressure gradient according to this embodiment. The pressure field is designed to feed analytes, including solid phase particles such as microbeads with single strand DNA immobilized thereon and/or other polymerization reactants, into feed microchannel 1320. The pressure gradient at the inlet acts as a siphon and induces particles and analytes to enter feed channel 1320. For charged switched nucleotides, the combination of the electric field and pressure gradients in purification channel 1310 helps reduce diffusion of unwanted or undesired materials, especially broken nucleotides, into feed channel 1320. For example, spontaneous hydrolysis may result in released (and detectable) labeled pyrophosphate (PPi-F) or other detectable material that could potentially interfere with detection in detection zone 1350. However, because the hydrolysis results in a PPi-F having a net positive charge and NP having a net negative charge, the PPi-F is drawn toward the negative electrode (cathode), and the NP is drawn toward the anode. Further, the rate of spontaneous hydrolysis in the purification channel is on the order of $10^{-9}$, and may be modified slightly by modifying the concentration of material fed into the channel. Thus, the probability of any broken nucleotide entering feed channel 1320 is greatly reduced. For different charge magnitudes and polarities, the effect will be essentially the same, and the fields can be optimized for the specific reactions. Additionally, the dimensions (width and/or depth) of purification channel 1310 is preferably greater than or even much greater than the dimensions of feed channel 1320, so as to further reduce the probability of broken nucleotides or other unwanted material diffusing into feed channel 1320. In certain aspects, the relative dimensions of the channels are for example, 10×4 microns for the purification channel, and 4×4 microns for the feed channel. These dimensions are merely one example and are not intended to be limiting. The pressure differential within feed channel 1320 creates a continuous flow from channel 1310 to recycle channel 1360, and prevents material returning from recycle channel 1360.

Figure 14:
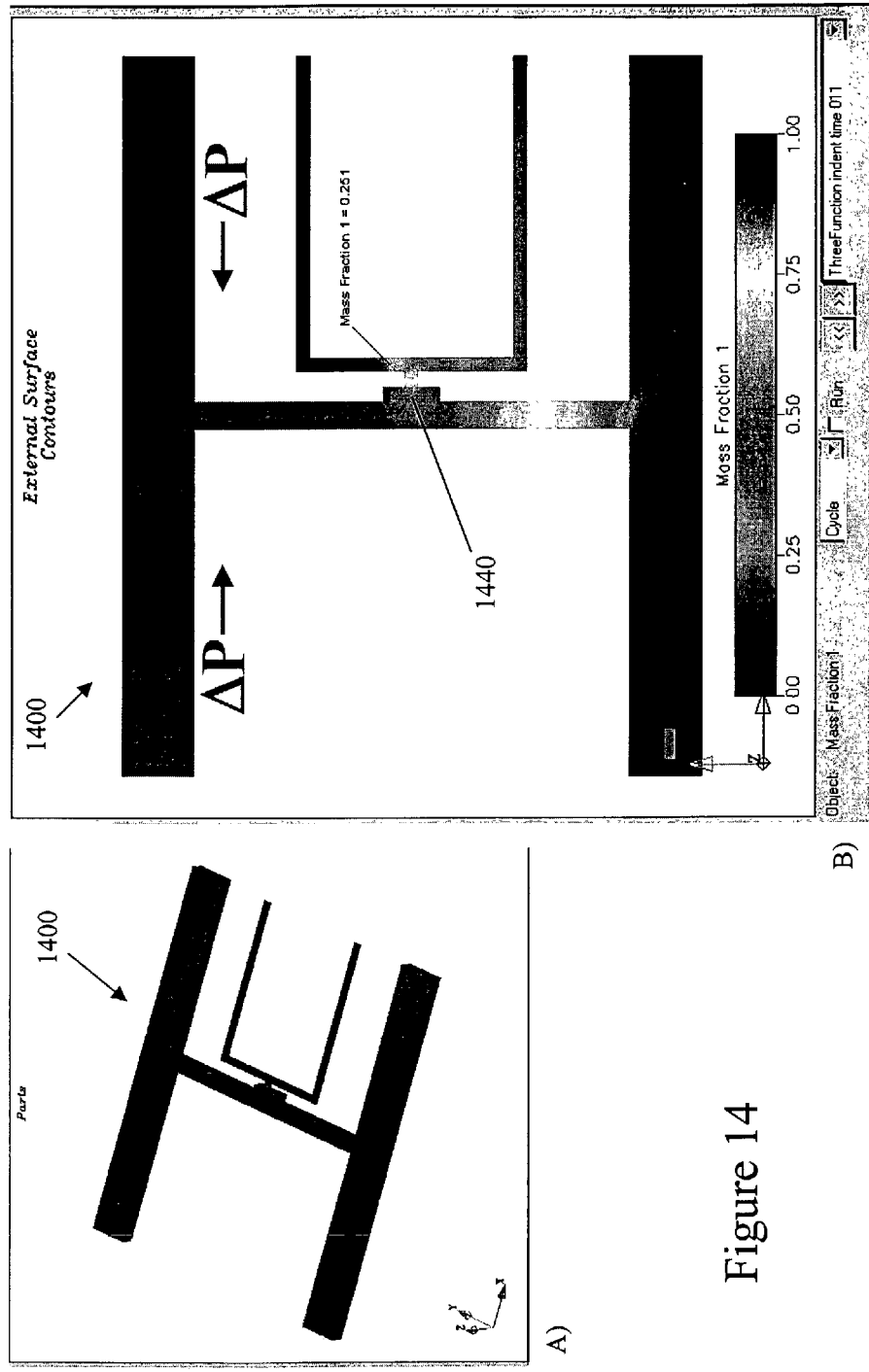
FIG. 14 illustrates another embodiment of a flowcell according to the present invention.

Beads, or other solid phase particles, and analytes entering feed channel 1320 move toward recycle channel 1360 due to for example, a pressure gradient, electric field loading and the like, within channel 1320. In certain aspects, a solid phase is trapped at an inlet to an extension channel 1340, which fluidly couples feed channel 1320 with a separation channel 1330. The pressure differential at the inlet acts as a siphon which traps a bead or other solid phase. In general, the inlet to extension channel 1340 should be smaller in size than the bead or particle to facilitate trapping the solid phase proximal the inlet. Preferably, the trapped bead or particle does not completely block fluid flow into extension channel 1340. FIG. 14 illustrates another embodiment of a flowcell according to the present invention. As shown flowcell 1400 is similar in design to flowcell 1300 and includes a bead cove fabricated into the substrate. Bead cove 1440 is provided in some embodiments to facilitate trapping a solid phase particle or bead proximal the inlet to the extension channel. Bead cove 1440 may be substantially the same size as a bead or other solid phase, or it may be larger, or it may be smaller with a feature adapted to mate or attach to a solid phase. Further, bead cove 1440 is shown as rectangular, but it may take on any shape. Preferably, bead cove 1440 is of sufficient size to hold only one bead.

In one embodiment, nucleic acid is retained in the sequencing channel after it has been induced into the channel by an electric field, and the electric field has been turned off or reduced in magnitude. For example, when DNA is inserted into a confining channel, entropic recoil forces cause the molecules to move from a tight space into a more open one. This phenomenon is utilized to retain DNA in the channel. By directing DNA (e.g., attached on one end to a trapped bead) in an electric field through a constricting channel (e.g., 50 nm deep×1 μm wide) and then onward into a less-constricting channel (e.g., 500 nm deep×2 μm wide), the DNA present in the less-constricting channel holds itself in the less-constricting channel and does not recoil back to the bead. For example, in one embodiment, the channel geometry is such that the channel transitions gradually from a relatively large channel where the bead is located, to a relatively constricted channel, with an abrupt transition to the less-constricted channel. The abrupt transition provides for example, a wall against which the DNA thermal motion exerts a force to prevent the DNA from recoiling back towards the bead.

In certain aspects, the extension channel is provided at a different level than the feed channel 1320. For example, extension channel 1310 may be fabricated on one substrate and feed channel 1320 fabricated on a second substrate, such that when the two substrates are pressed together, the extension channel and feed channel intersect in one plane, with each channel being at a different relative level or height. The two channels are fluidly connected at the planar intersection. U.S. Provisional Application No. 60/214,714, filed Aug. 24, 2001, discloses fabrication techniques for forming such a planar channel intersection using two substrates, and is hereby incorporated by reference in its entirety. It should be appreciated that an array of channel intersections may be formed using these techniques.

In certain aspects, a magnetic field generating element such as magnet may be used to facilitate trapping a magnetic or magnetizable (e.g., superparamagnetic) bead or particle. For example, a permanent magnet or set of one or more electric coils may be positioned proximal the inlet to the extension channel 1310 or proximal bead cove 1440. U.S. Provisional Application No. 60/314,709, filed Aug. 24, 2001, describes techniques for immobilizing a DNA molecule or molecules on a magnetic micro-bead in a single molecule configuration, and is hereby incorporated by reference in its entirety.

Figure 15:
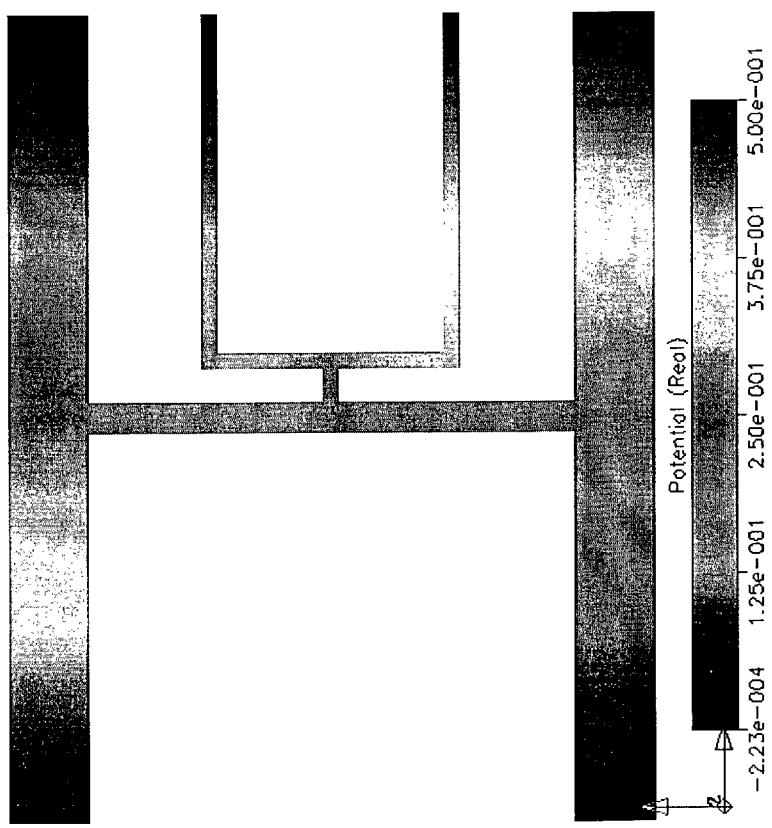
FIG. 15 illustrates the electric potential in the various microchannels of the flowcell of FIG. 13 in one specific configuration according to an embodiment of the present invention.

Returning to FIG. 13, as shown, electrodes are positioned at opposite ends of recycle channel 1360 to induce movement of charged material toward the electrodes. Additionally, the electrodes are preferably positioned, and the polarities and magnitudes controlled, so that there is substantially no electric field, or a negligible field, within feed channel 1320. This is desirable to prevent moving or jostling of a trapped bead in feed channel 1320. In general, therefore, it is preferred that the electric potential at the inlet to feed channel 1320 is substantially equal to the electric potential at the outlet to channel 1360. For example, in one aspect as shown, the potential gradient in purification channel 1310 is configured so that it is substantially equal and opposite to the potential gradient in recycle channel 1360, and so that the potential at either end of feed channel 1320 is substantially the same, thereby resulting in substantially no electric field, or negligible electric field, within feed channel 1320. FIG. 15 illustrates the electric potential across the flowcell 1300 in such a configuration. As can be seen, the electric field (gradient of the potential) is substantially zero across feed channel 1320. It should be appreciated that other electrode configurations and parameters may be implemented.

In preferred aspects, the flowcell energy field (pressure, electric potential, etc.) parameters are configured such that a reaction takes place within or proximal extension channel 1340. For example, for a DNA sequencing assay, beads, NP probes and polymerization enzymes are provided to flowcell 1300 via an input port in purification channel 1310. A bead having an attached DNA molecule is coerced (e.g., siphoned) into feed channel 1320 and trapped proximal extension channel 1340. The bead is too large to enter extension channel 1340, and the energy field (e.g., pressure and/or electric field) and/or magnetic field generating mechanism traps the bead proximal extension channel 1340. Preferably the micro-bead has only one molecule attached thereto for single molecule analysis, although multiple molecules may be attached thereto. The DNA on the trapped bead is also influenced by the energy field which biases the DNA into the extension channel (providing that the extension channel is sufficiently large, e.g., at least about 1.5 nm across and more preferably 0.1 micron or greater, and most preferably at least 0.5 to 1.0 microns or greater), and if the molecule is long enough, into separation channel 1330. Thus, a reaction may take place within extension channel 1340 and/or within separation channel 1330, depending on the length of the molecule and the dimensions of extension channel 1340.

In preferred aspects, electrodes are positioned at the ends of separation channel 1330 to induce an electric field therein. The DNA molecule, having a net charge is biased toward the appropriate electrode; as shown, a DNA molecule 1325 extending into the separation channel and having a net negative charge is biased toward the positive electrode (anode). NP probes and polymerase are supplied into feed channel 1320, due to the pressure differential at the inlet, and into extension channel 1340 around the trapped bead. In one aspect, the NP probes and polymerase are both negatively-charged, so both reagents follow the pressure field around the trapped bead and into the separation channel going toward the anode. The strained DNA is bathed in the solution of NP probes and polymerase. Upon each incorporation event, a labeled pyrophosphate moiety PPi-F is cleaved from the incorporated NP probe and its electric charge changes to net positive. This charge switch causes the PPi-F to move towards the negative electrode (cathode) in the separation channel and into detection region 1350. If the DNA extends into the separation channel toward the anode, the cationic PPi-F moves against the flow of anionic NP probes and polymerases and continues toward the cathode. Once past the intersection, the PPi-F is free from the labeled NP probes and it is detected with single-molecule sensitivity in detection region 1350.

A bulk flow may be generated within separation channel 1330 in some embodiments, for example, using one or pressure generating mechanisms at the ends of the separation channel. Such a bulk flow may be used to help bias material into or away from detection region 1350 in conjunction with, or in place of, an electric field within separation channel 1330. A bulk flow may be useful to control the speed at which detectable product enters detection region 1350. For example, where the reactant and product both have the same charge polarity, but different magnitudes, a bulk flow is useful to separate the product and reactants based on their different mobilities in the bulk flow due to the differences in charge. For example, product having a greater net positive charge than positively charged reactant will diffuse toward the cathode more readily than the reactant due to the stronger interaction with the electric field. The energy fields may be tuned or balanced to enhance diffusion of desired material into the detection region.

Preferably flowcell 1300 is configured so that there is substantially no electric field within extension channel 1340, primarily to reduce the effect that an electric field may have on the trapped bead. It should be understood that an electric field may be present in extension channel 1340, and may indeed facilitate biasing of reactants and/or product into separation channel 1330. As shown in FIG. 15, there is substantially no electric field within extension channel 1340 as configured.

Figure 16:
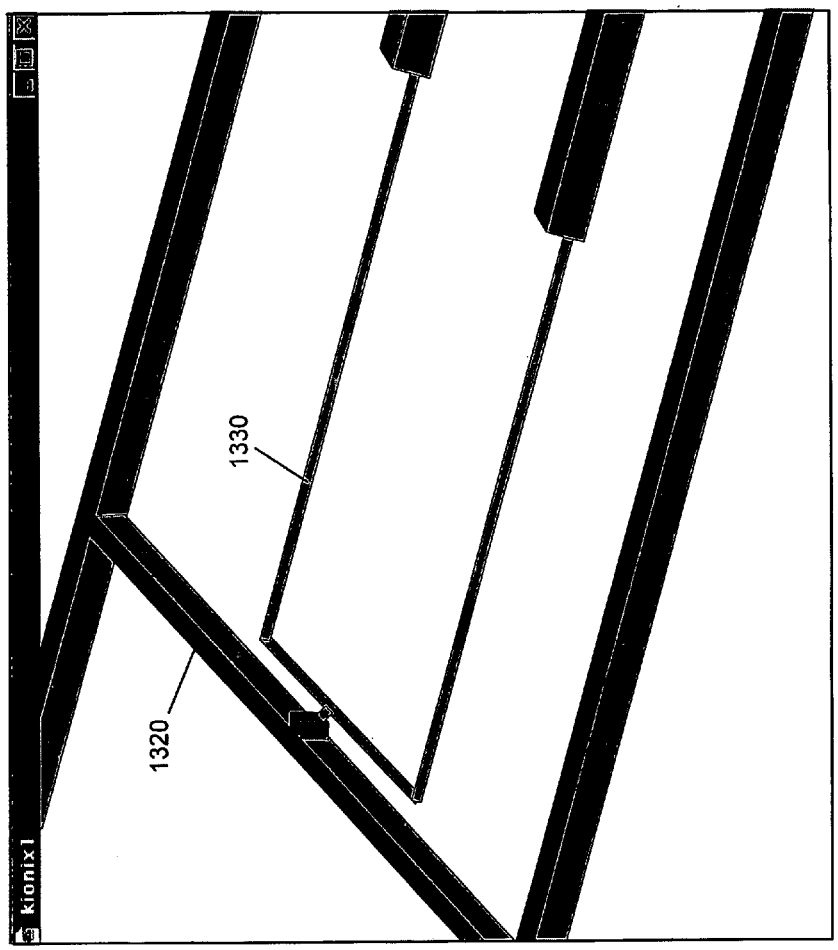
FIG. 16 illustrates a flowcell similar to the flowcell of FIG. 13, but with a portion of the separation channel in a 3D view with extensions.

In some aspects, the dimensions of the separation channel 1330, or a portion of the separation channel, is smaller relative to other channels. As shown in FIG. 16, for example, a portion of separation channel 1330 is much smaller than the dimensions of the feed channel 1320 and other channels. In general, it is preferred that the dimensions of at least the portion of separation channel 1330 within detection region 1350 be minimized to facilitate detection analysis. It is preferred that the depth of the detection region be between about 0.1 micron and 1.0 micron and more preferably, smaller than 0.5 micron to enhance excitation and detection by ensuring that detectable fluorescent moieties flow within the detection field of the detection system and prevent detectable fluorescent moiety from passing outside, or below, the detection field and/or the excitation field. For example, where TIRF is used as the detection methodology, the exponentially decaying evanescent field generated upon total internal reflection of a light at a high index to low index boundary or interface (e.g., between a glass and water or liquid boundary) is used to excite fluorophores within the liquid proximal the interface. For angles of incidence measured relative to the interface normal ($\theta$) above the critical angle, the evanescent field intensity (I) drops off exponentially with distance z into the low index, e.g., liquid, medium as follows:

$$I(z)=I(0)\exp(-z/d),$$

where I(0) is the intensity at the interface, and the exponential decay constant (distance) is:

$$d = \frac{\lambda_0}{2\pi}(n_2^2\sin^2\theta - n_1^2)^{-1/2},$$

where is $\lambda_0$ is the wavelength of excitation light in vacuum, and $n_2$ and $n_1$ are the indices of refraction of the glass and the liquid, respectively. The angle-dependent decay constant is typically on the order of 100 nm to 200 nm. It is therefore preferred that the depth of the detection region be less than approximately four times the evanescent decay constant of the evanescent excitation field, more preferably less than approximately three times the evanescent decay constant, and even more preferably less than approximately two times the evanescent decay constant, to ensure optimal excitation of a fluorescent moiety as well as optimal detection. One useful microscope for through-the-objective TIR measurements is provided by Olympus and has 60× magnification and a N/A of 1.45 (lens and flowcell), wherein $n_2 \approx 1.52$. Other microscopes and optical detection systems may be used.

FIG. 16 illustrates a flowcell similar to flowcell 1300, but with a portion of the separation channel reduced in dimension relative to other channels of the flowcell. Such a structure may be fabricated, for example, using the two-substrate intersection techniques of U.S. Provisional Application No. 60/214,714, which was previously incorporated by reference, wherein the separation microchannel and extension channel are etched on one substrate and the remaining channels etched on a second substrate.

In preferred aspects, a feedback system monitors and controls the flow of materials throughout flowcell 1300. For example, in one embodiment, the detector is coupled to a controller, such as a microprocessor or other microcontroller, that analyzes the detection signals. The controller is preferably communicably coupled to the various energy field generating mechanisms, e.g., pressure generating mechanisms, electrodes, etc., as well as the material input port to purification channel 1310. If it is determined that detection is occurring to fast or to slow, for example, the controller modifies the energy fields and or the rate material is fed into purification channel 1310 to adjust the amount of material flowing and/or the flow rate of material into the extension and separation channels. For example, the pressure fields in purification channel 1310 may be modified, and/or the electric fields may be modified, so as to adjust the amount of material diffusing into feed channel 1320, and therefore into separation channel 1330. The separation channel energy fields may be adjusted separately from the energy fields of other channels. Alternatively, an operator can manually control the feedback system to adjust the feed rate and/or energy fields to adjust the flow of material as desired. In some aspects, the viscosity of the medium in the flowcell can be adjusted in response to detection signals, e.g., by introducing buffer having a higher or lower viscosity, to enhance or decrease the diffusion of molecules into the feed channel.

In preferred aspects, for nucleotide incorporation assays, the order in which nucleotides incorporate is preserved and detected; the order of the product, e.g., cleaved PPi-F, is detected in the detection region. For example, as a polymerase works its way along the DNA molecule, each incorporated nucleotide results in a released pyrophosphate moiety. The energy fields within the flowcells of the present invention are configured so that the order of released pyrophosphate moiety is preserved through the detection region. Preferably, the system detects on a first-incorporated-first-detected basis. The energy fields may be modified, by automatic or operated controlled feedback, to optimize conditions such as flow and charge mobility of the detected product. For example, a bulk flow away from the detection region within a separation channel may be increased or decreased, or the electric field therein may be increased or decreased, to control the rate at which product is detected and/or the spatial separation between individually detectable product elements (e.g., each released pyrophosphate moiety).

As shown in FIG. 14, the mass fraction, or concentration of material, within various regions of flowcell 1300 may be controlled with appropriate configuration of the energy fields. For the DNA assay as described above, the fields are configured such that the concentration is reduced, e.g., orders of magnitude lower, in the detection region portion of separation channel relative to the other portion of separation channel and the extension channel which itself has a reduced concentration relative to the feed channel and purification channel.

In certain aspects, it is preferred that assays using multiple trapped beads be performed, for example, to facilitate high throughput screening and rapid sequencing. FIG. 10 illustrates such an array including 2 separation channels coupled to a feed channel by two extension channels. It should be appreciated that any number of channels may be coupled to the feed channel, limited only by manufacturing techniques and materials used.

Figure 17:
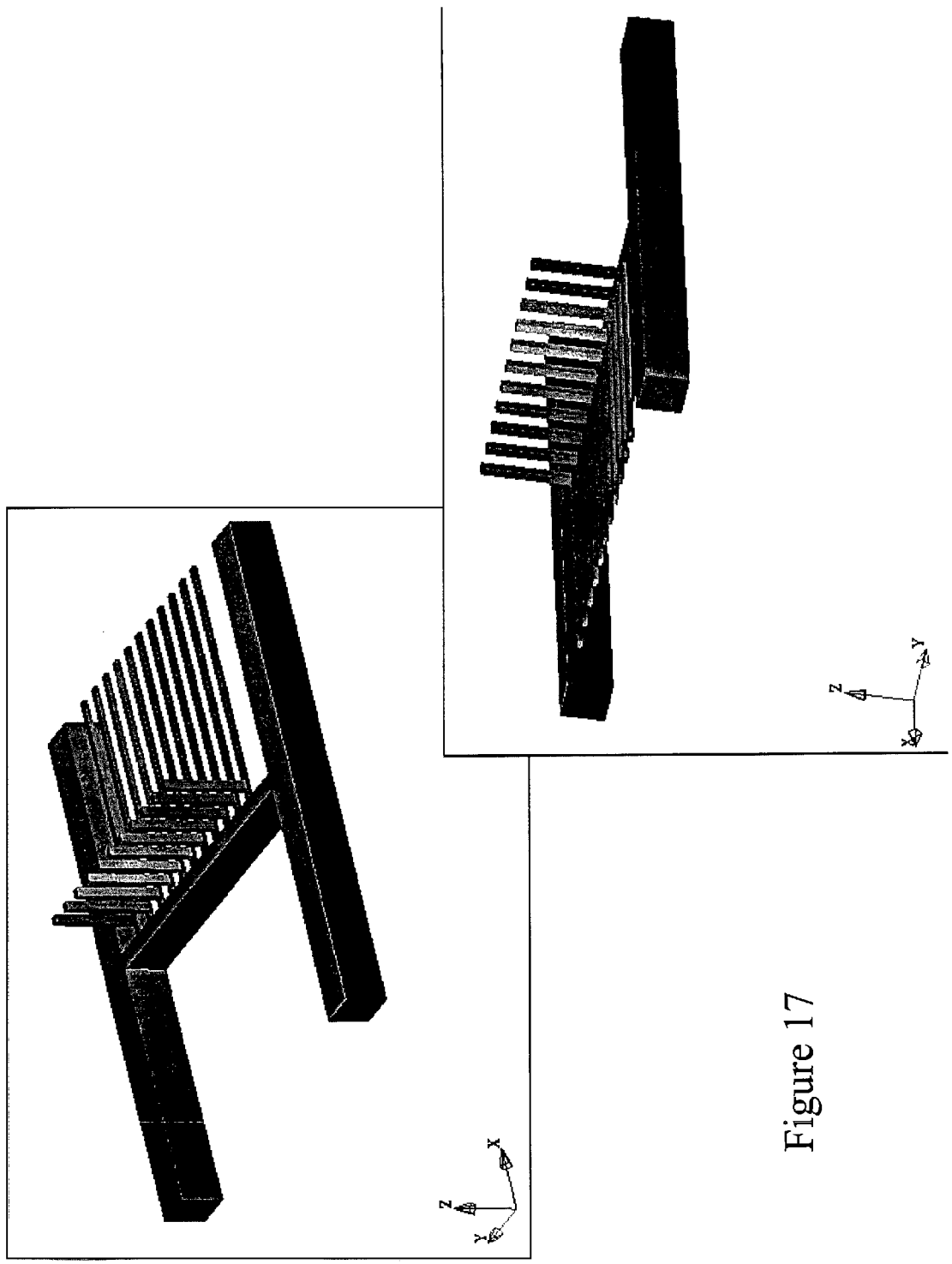
FIG. 17 illustrates a three dimensional flowcell array according to one embodiment.

In one embodiment, a three dimensional array of microchannels is provided. FIG. 17 illustrates a three dimensional flowcell array according to one embodiment. As shown, multiple separation channels are provided, each being coupled to a feed channel via separate extension channels. Such an array can be used to facilitate detection in detection regions along the separation channel portions in the X-Y plane, or along a plane perpendicular thereto, e.g., in the separation channel portion along the Y-Z plane. It should be appreciated that other three-dimensional array configurations may be implemented.

Figure 18:
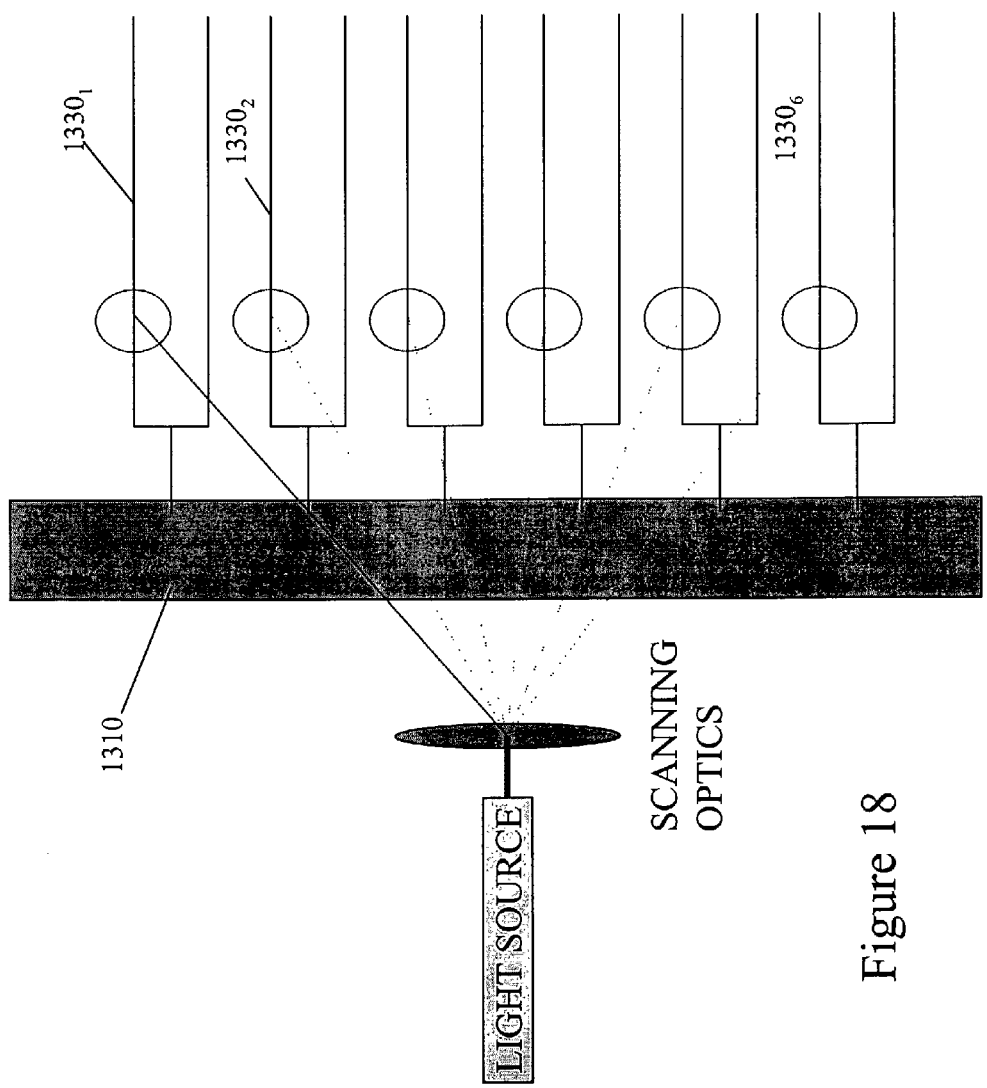
FIG. 18 illustrates another array embodiment, including an optical system useful for illuminating specific areas in the array of separation channels, e.g., detection regions.

FIG. 18 illustrates another array embodiment, including an optical system useful for illuminating specific areas in the array of separation channels, e.g., detection regions. In this embodiment, multiple specific regions may be illuminated simultaneously or in an order, e.g., by scanning. Advantageously, only the detection regions are illuminated without illuminating other regions such as the feed channel 1310, extension channels 1320 or other portions of the separation channels where detectable analytes may become excited and overwhelm the detector. In alternative embodiments, a wider illumination beam may be used to illuminate a larger area of the device, in which case it would be desirable to mask areas on the microfluidic device to prevent unwanted excitation of, and emission from, fluorescent moieties that may be present in the microchannels. Suitable illumination sources, such as pulsed or continuous wave conventional gas and solid-states lasers, semiconductor lasers, tunable dye lasers, arc-lamps and the like may be used. Additionally, various filters, diffraction gratings, mirrors, lenses and other optical elements may be used to manipulate and interact with the illuminating and emitted radiation as desired.

Figure 19:
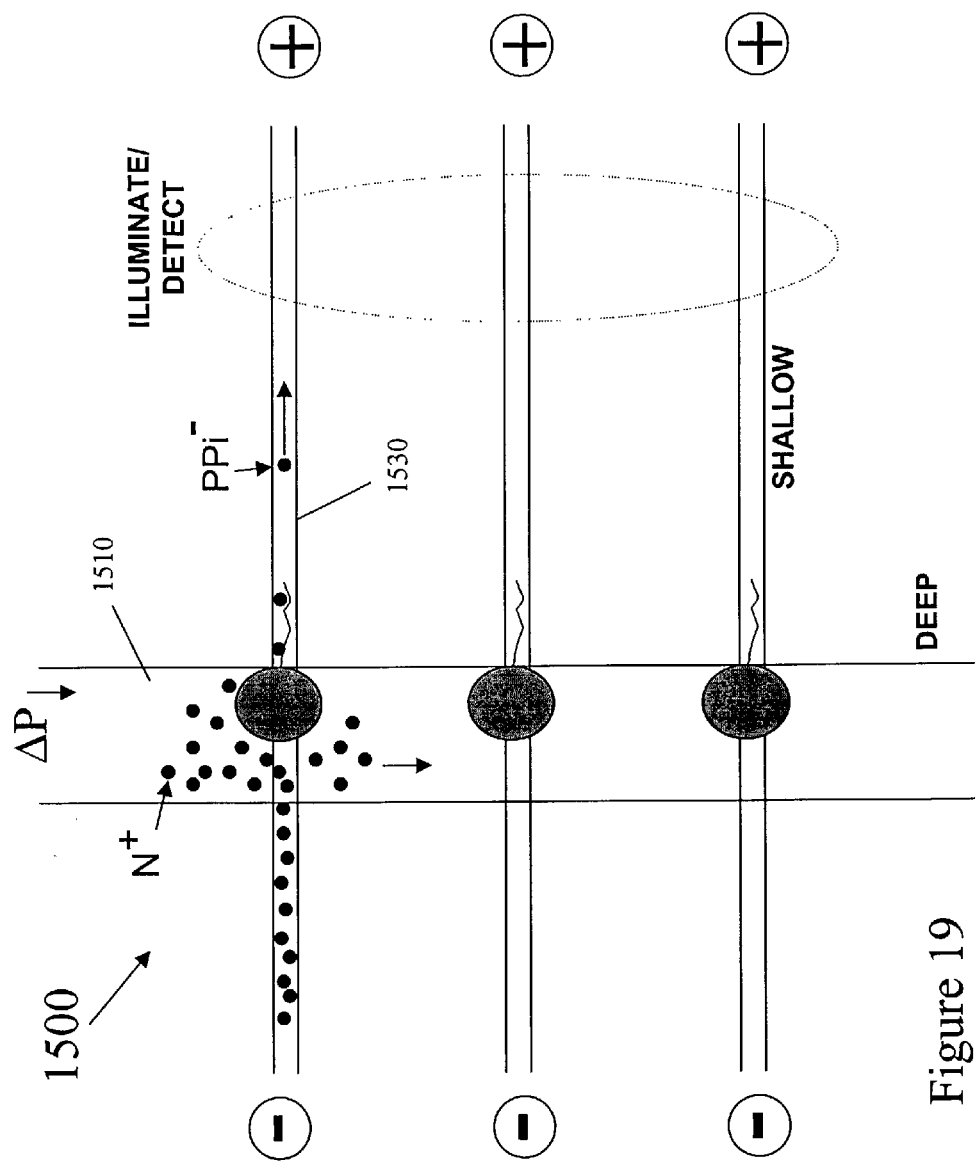
FIG. 19 illustrates a portion of a flowcell according to an embodiment of the present invention.

FIG. 19 illustrates a portion of a flowcell 1500 according to another embodiment. Flowcell 1500 includes a feed microchannel 1510 and a plurality of separation channels 1530 as shown. Feed channel 1510 is of sufficient size to permit beads to flow therethrough. In preferred aspects, beads are trapped proximal the inlet to the separation channels 1530 as shown due to a biasing pressure gradient and/or magnetic attraction as discussed above. Preferably, the separation channels are formed on a first substrate that is coupled to a second substrate with the feed channel formed thereon so the channels intersect along one plane as described in U.S. Provisional application No. 60/214,714, although the microchannels may be disposed in the same substrate. Individual electrodes may be coupled to the ends of each separation microchannel 1530, although the system shown may be advantageously configured with a single positive electrode coupling to the ends of multiple separation channels, and a single negative electrode coupling to the other ends of the separation channels. In this embodiment, the reaction, e.g., enzymatic cleavage reaction, takes place proximal the intersection of each separation channel and the feed channel. Most of the nucleotides coming down the feed channel 1510, e.g., due to pressure, that enter the separation channel will tend to enter toward the cathode due to their positive charge, however, some will randomly walk, or diffuse, into the reaction zone, or DNA extension zone. If a nucleotide incorporates, the resulting negatively charged PPi-F separates and moves toward the anode due to the electric field within the separation channel.

Figure 20:
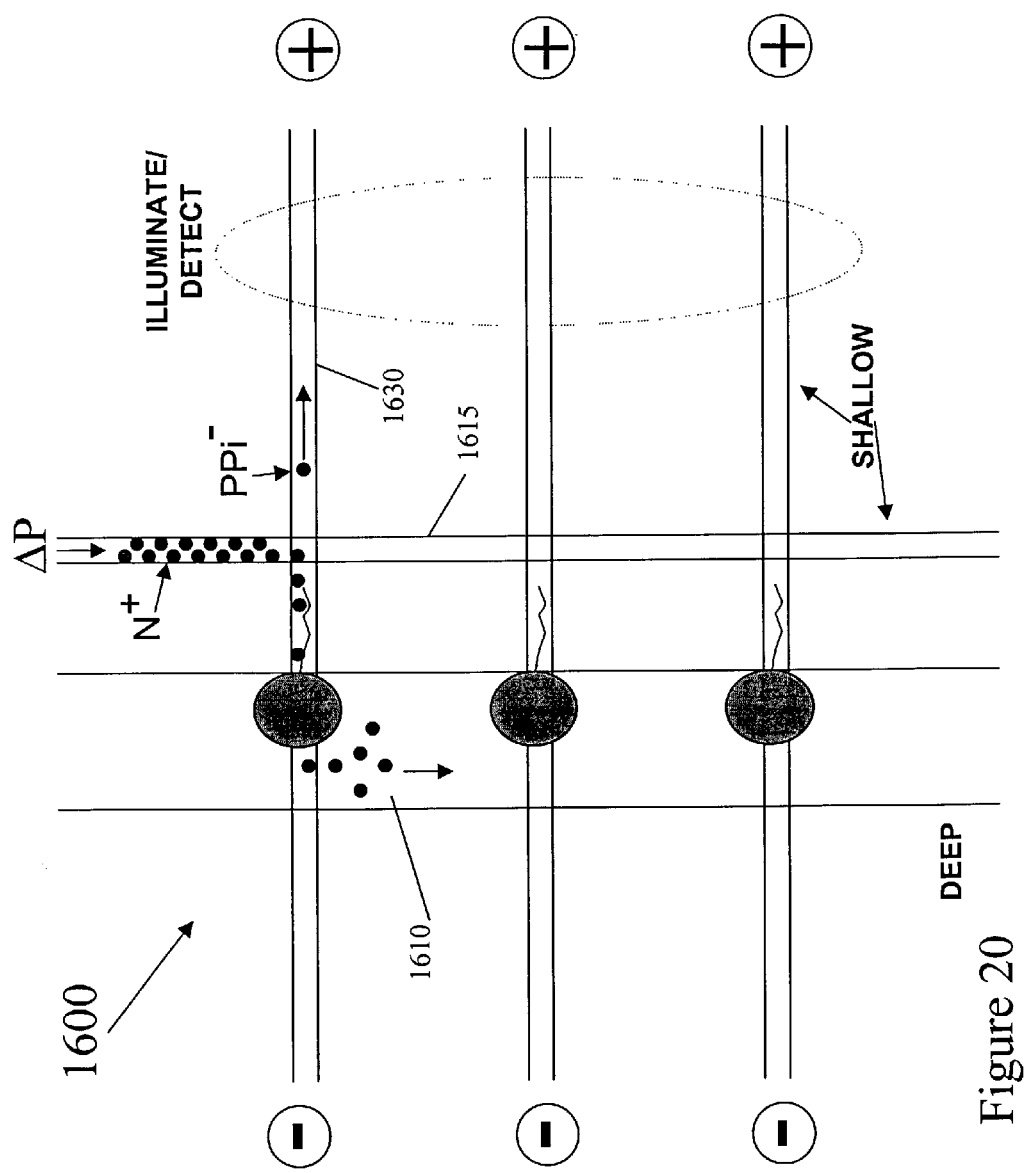
FIG. 20 illustrates a portion of a flowcell according to an embodiment of the present invention.

FIG. 20 illustrates a portion of a flowcell 1600 according to an embodiment of the present invention. Flowcell 1600 is similar to flowcell 1500 of FIG. 19, but includes an additional feed channel 1615. In one embodiment, beads (with attached DNA molecules) are provided in feed channel 1610 as above, but the separate feed channel 1615 supplies the nucleotides independently of the beads. The nucleotides (e.g., NP probes) that enter the separation channel 1630 move toward the extended DNA molecule due to their positive net charge, and the reaction takes place in the region between the two feed channels. If a nucleotide incorporates, the resulting PPi-F separates back toward the positive electrode into the detection region and will not re-enter the second feed channel 1615 due to the tight electric field in the separation channel proximal the intersection. Unincorporated nucleotides and other material flow toward the negative electrode, with some diffusing into feed channel 1610. Preferably second feed channel 1615 intersects each separation channel 1630 beyond the length of the extended DNA molecule on the bead to ensure a complete reaction. One or multiple electrodes may be coupled to one or multiple ends of separation channels 1630 as above.

As shown in FIGS. 19 and 20, a single illumination beam may be used to illuminate each separation channel proximal or within the corresponding detection region. Preferably, each separation channel has reduced dimensions (e.g., 1 micron wide by 0.5 micron deep) relative to the main feed channel (e.g., 4 micron by 4 micron) as discussed above. In embodiments using a secondary feed channel, the dimensions of the separation channels are preferably similar or smaller than those of the secondary feed channel.

Figure 21:
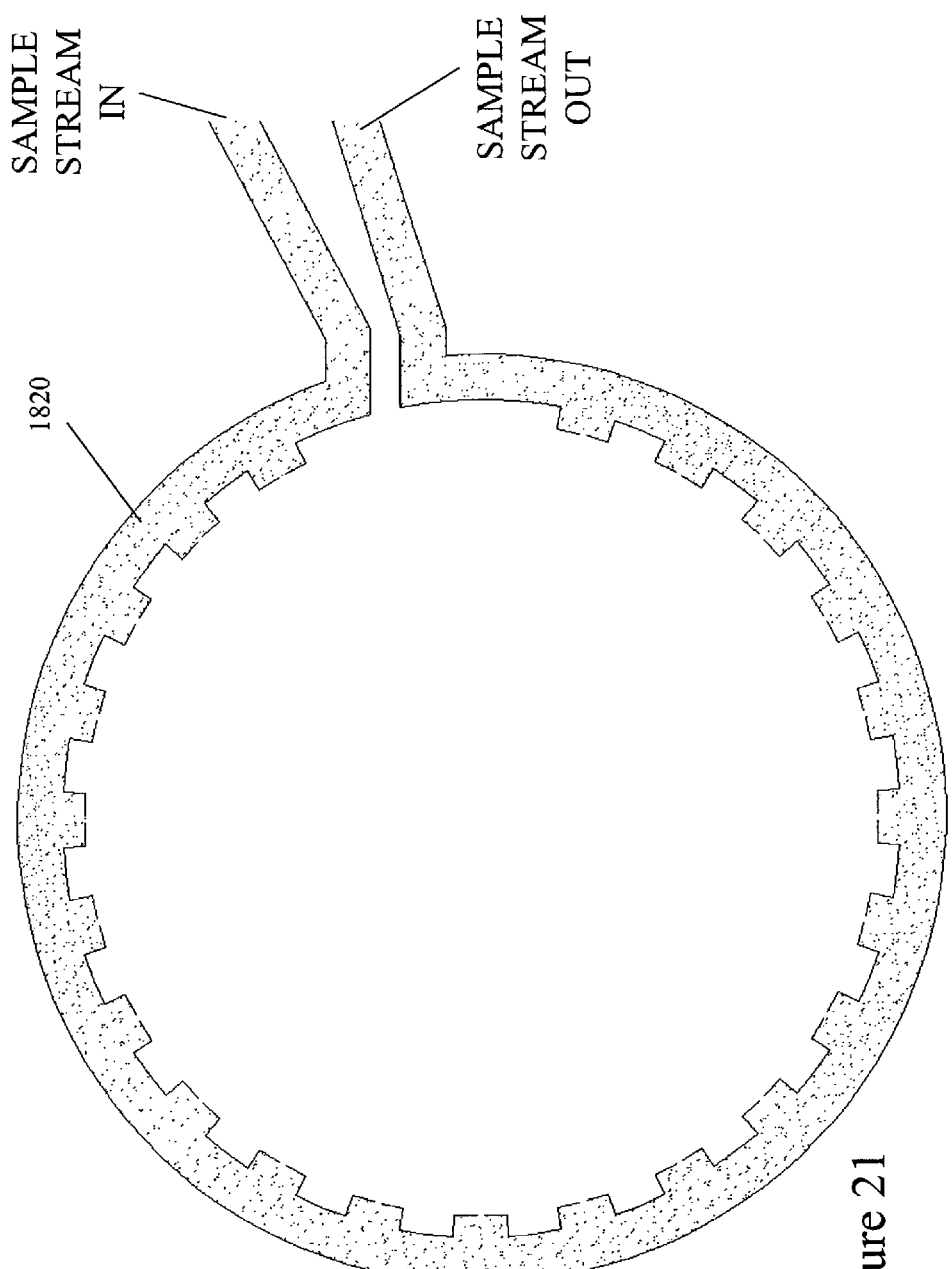
Figure 22:
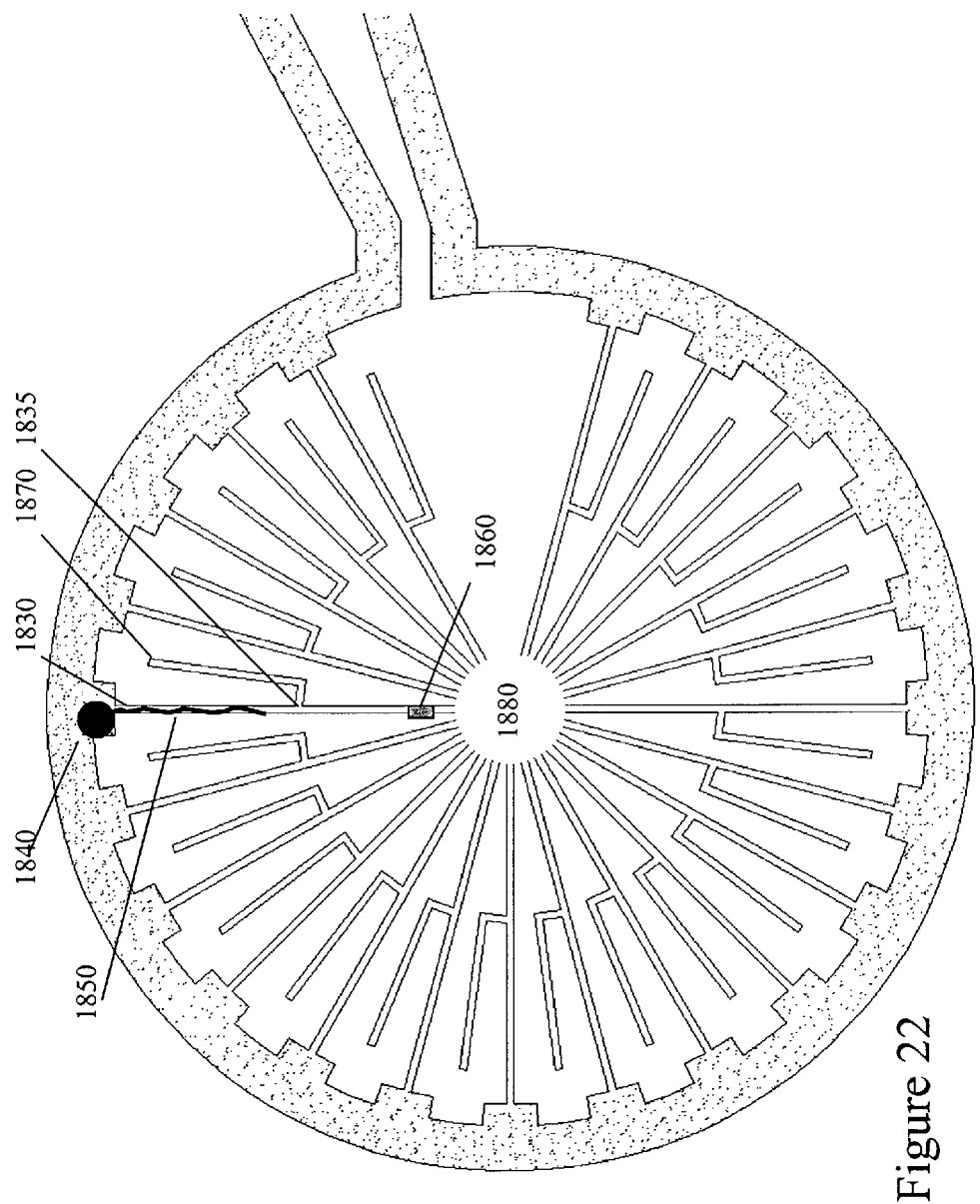

FIGS. 21–24 illustrate a radial flowcell design according to the present invention. As shown in FIG. 21, a feed channel 1820 supplies reagents, such as beads, NP probes, enzymes, etc., and is sufficiently large to permit passage of beads. For example, for beads of approximately 2.8 micron diameter, the width and depth of feed channel should be approximately 4 microns or greater. Bead coves are preferably provided as shown, but are not necessary. A pressure flow is generated in feed channel 1820 with flow proceeding counterclockwise as shown. As shown in FIG. 22, a plurality of channels 1830 are fluidly coupled to feed channel 1820 and are preferably smaller in dimension, e.g., 0.5 micron deep and 1.0 micron wide, relative to feed channel 1820, e.g., 4 micron by 4 micron. Electrodes 1870 and 1880, positioned at the ends of a separation channel, create an electric field therebetween. There is negligible electric field between intersection 1835 and the bead cove. Thus, if a bead 1840 trapped in a bead cove proximal channel 1830 has a DNA molecule 1850 attached thereto, the DNA will extend toward electrode 1880 due to pressure flow. NP probes entering channel 1830 flow past the DNA, and PPi-F is generated by polymerase activity on the DNA. The electric field drives intact NP probes toward electrode 1870 and drives the PPi-F toward electrode 1880 and past a detection region 1860.

Figure 23:
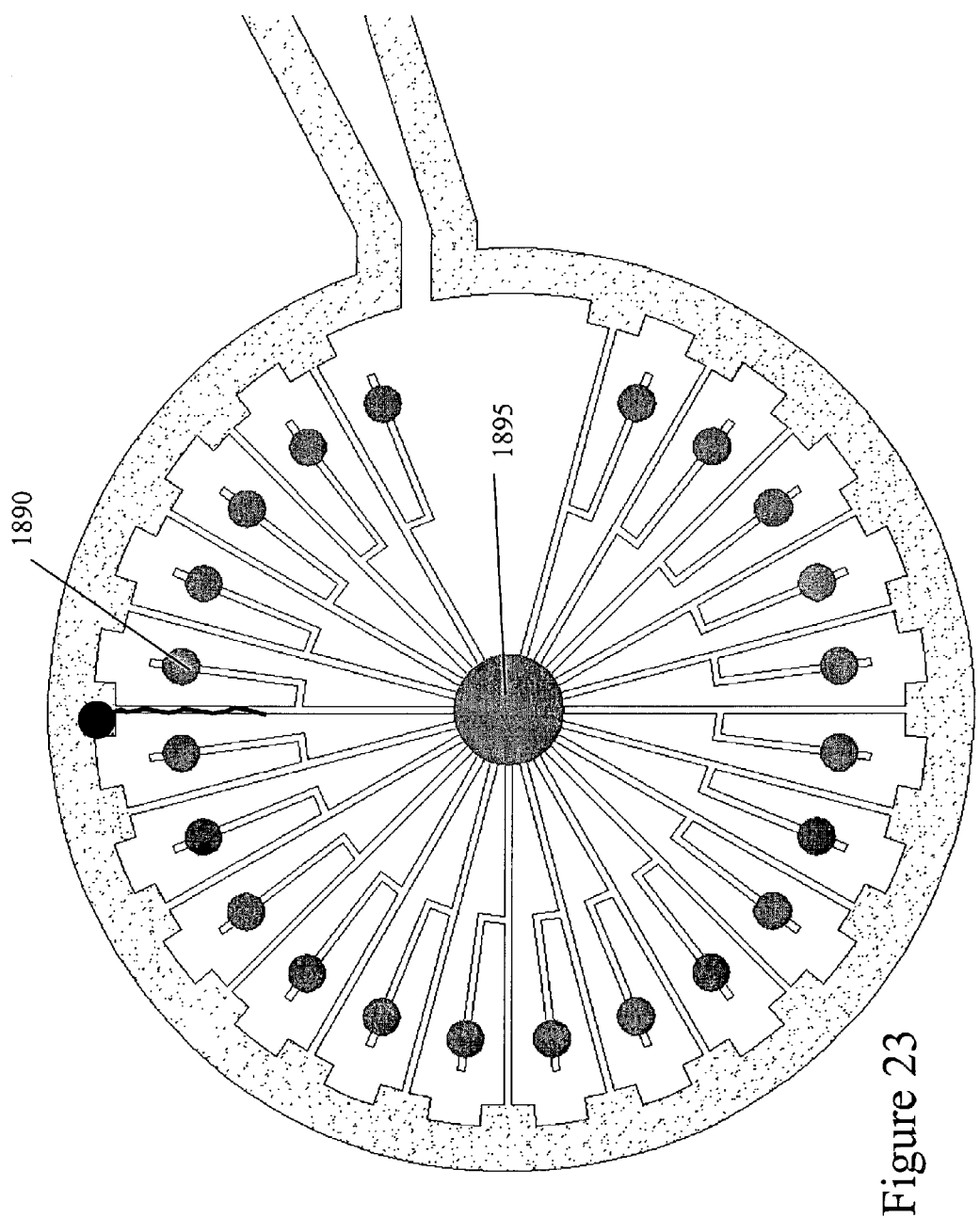

Preferably feed channel 1820 is fabricated on the same substrate as channels 1830, although the feed channel and channels 1830 may be fabricated on different substrates and attached together. In one embodiment as shown in FIGS. 23 and 24, via channels 1890 and 1895 couple channels 1830 to reagent removal channels 1910 and 1940. In this embodiment, feed channel 1820 and channels 1830 are fabricated on the same substrate and reagent removal channels 1910 and 1940 are fabricated on a different substrate and pressed together, although a layered structure may be fabricated on a single substrate. Via channels 1890 and 1895 fluidly couple channels 1830 with the reagent removal channel 1910 and 1940, respectively. In one embodiment, the via channels perforate the flowcell substrate and extend upward (out of the page). Buffer flowing from an inlet to channel 1910 sweeps away reagents that have entered channel 1910 from the via channel 1890 to an outlet port, and buffer flowing from via channel 1895 into reagent removal channel 1940 exits at another outlet port.

A flowcell according to this embodiment advantageously requires only one illumination source for illuminating all detection regions 1860 simultaneously. The focal plane of an illumination beam can be readily adjusted to cover all regions 1860 simultaneously. In one embodiment, the specific illumination and detection system is for example, TIR illumination, with a 100 micron spot size. To avoid unwanted excitation and noise, photobleaching of reagent (e.g., fluorophores), and/or photodetector "blooming", regions other than detection regions 1860 are preferably masked. For example, a layer of opaque material (e.g., optically opaque at desired wavelengths) may be deposited over portions of the flowcell, or an optical mask or passivation layer may be provided. Such masking is useful in some aspects to mask away, i.e., prevent illumination or excitation of, detectable reactant(s) from reaction product.

V. EXAMPLES

The following examples are offered to illustrate, but not to limit the claimed invention.

Example I

This example shows an algorithm for calculating charge on the intact nucleotide probe and cleavage product, taking into account contributions from hydrogen ions and divalent metal cations. It will be appreciated by those of skill in the art that particular equilibrium constants are affected by the instant chemical environment, and that the equilibrium constants affect the outcome of the calculation. The algorithm explained in the example was implemented in a computer program to execute the calculations, some results of which are illustrated in FIG. 3.

For steps 1–3 below, refer to FIG. 5 for the definition of the indicated equilibrium constants K (in boxes). Values for the equilibrium constants are taken from analogous compounds in Frey and Stuhr (1972) *Journal of the American Chemical Society*, 94:8898. In the calculation steps, these definitions apply: N-PPP-F="L" (ligand); $H^+$="H" (hydrogen ion) and $Mg^{++}$="M" (counter ion metal).

I. STEP 1 

Compute H binding to L at a given pH:
the equilibrium $L + H \in LH$
$K_{HL} = [LH] / [L]*[H]$
VALUE OF $K_{HL}$
LOG $K_{HL} \cong 2$
the primary ionization of all nucleotide mono, di and triphosphates
f1, the fraction of L in protonated form LH $f1 = [H] / ([H] + K_{HL})$
$f1 \cong 0$
f2, the fraction of L in unprotonated form L $f2 = 1 - f1$
$f2 \cong 1$ at neutral pH II. STEP 2 - 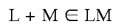

COMPUTE M BINDING TO L AT A GIVEN [M] AT THE OF STEP 1 the equilibrium $L + M \in LM$
$K_{ML} = [LM] / [L]*[M]$
value of $K_{ML}$ $\log K_{ML} = 2.18$
the analog of N-PPP-F is protonated-NTP (NTP-H), where H $\cong$ F
    ATP-H + Mg $\in$ ATP(Mg)-H, log K = 2.18
    CTP-H + Mg $\in$ CTP(Mg)-H, log K = 2.18
f5, the fraction of L in complexed form ML $f5 = [M] / ([M] + K_{ML})$
f6, the fraction of L in uncomplexed form L $f6 = 1 - f5$ III. STEP 3 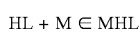

COMPUTE M BINDING TO HL AT A GIVEN [M] AT THE PH OF STEP 1 the equilibrium $HL + M \in MHL$
$K_{MHL} = [MHL] / [HL]*[M]$
value of KMHL

[HL] is negligible
[HL] is negligible because at neutral pH values, L is in the unprotonated form ($K_{HL} \cong 2$; above)
IV. STEP 4
Compute the fraction of each complexed form of L (refer to FIG. 5)
fracL = f2*f6
fracML = f2*f5
fracHL = f1*f4 $\cong$ 0*f4 $\cong$ 0
fracMHL = f1*f3 $\cong$ 0*f3 $\cong$ 0
V. STEP 5
Compute phosphate charge $Q_{phos}$ averaged over all forms of L
$Q_{phos} = Q(L)*fracL + Q(ML)*fracML + Q(HL)*fracHL + Q(MHL)*fracMHL$
where each Q is defined in the FIG. 5
VI. STEP 6
Compute nucleobase charge $Q_B$ due to nucleobase adducts B
the equilibrium $B + H \in BH$
$K_{BH} = [BH] / [B]*[H]$
value of $K_{BH}$ depends on whether the adduct B is for example a carboxylate(−) or arginine(+) or quaternary amine(+)
    $\log K_{BH} = 4.5$ for carboxylate
    $\log K_{BH} = 12$ for arginine or quaternary ammonium salt
    note: at pH values 6.5–8.5, these groups are effectively fixed negative or positive charges -continued fraction of protonated and unprotonated forms fracBH = [H] / ([H] + $K_{BH}$)
fracB = 1 – fracBH
charge $Q_B$ = charge of B
$Q_{BH}$ = charge of BH
$Q_B$ = fracBH*$Q_{BH}$ + fracB*$Q_B$
VII.  STEP 7
Compute γ-label charge $Q_G$ from γ-label adducts G
same logic as step 6
$Q_G$ = fracGH*$Q_{GH}$ + fracG*$Q_G$
VIII.  STEP 8
Compute overall charge $Q_{N-PPP-F}$ on N-PPP-F
$Q_{N-PPP-F}$ = $Q_{phos}$ + $Q_B$ + $Q_G$ Similar to the above, equilibrium calculations can be done for PP-F. The same logic applies as for N-PPP-F, except that different equilibrium constants are used which are appropriate for PP-F (values given in boxes below). For steps 1–3 below, refer to FIG. 5 for the definition of the indicated equilibrium constants K (in boxes). Values for the equilibrium constants are taken from analogous compounds in Frey and Stuhr (1972) JACS 94:8898. The following definitions apply PP-F="L" (ligand); $H^+$="H" (hydrogen ion) and $Mg^{++}$="M" counter ion or (metal).

I.  STEP 1 - 

Compute H binding to L at a given pH:
the equilibrium

L + H ⊂ LH
$K_{HL}$ = [LH] / [L]*[H]
                                       VALUE OF $K_{HL}$ log $K_{HL}$ ≅ 2
the primary ionization of all nucleotide mono, di and triphosphates
f1, the fraction of L in protonated form LH f1 = [H] / ([H] + $K_{HL}$)
f1 ≅ 0 at neutral pH
f2, the fraction of L in unprotonated form L f2 = 1 – f1
f2 ≅ 1 at neutral pH II.  STEP 2 - 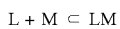

COMPUTE M BINDING TO L AT A GIVEN [M] AT THE PH OF STEP 1 the equilibrium

L + M ⊂ LM
$K_{ML}$ = [LM] / [L]*[M]
value of $K_{ML}$ log $K_{ML}$ = 3.20
the analog of PP-F is unprotonated nucleotide diphosphate or protonated pyrophosphate
ADP + Mg ⊂ ADP(Mg), log K = 3.22 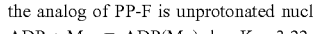
DP + Mg ⊂ CDP(Mg), log K = 3.21 
PP-H + Mg ⊂ (Mg)PP-H, log K = 3.18 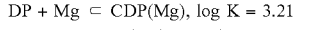
f5, the fraction of L in complexed form ML f5 = [M] / ([M] + $K_{ML}$)
f6, the fraction of L in uncomplexed form L f6 = 1 – f5

-continued

III. STEP 3 - 

COMPUTE M BINDING TO HL AT A GIVEN [M] AT THE PH OF STEP 1 the equilibrium

HL + M ⊂ MHL
$K_{MHL}$ = [MHL] / [HL]*[M]
value of $K_{MHL}$ log $K_{MHL}$ = 1.60
the analog of H-PP-F is protonated nucleotide diphosphate N-PP-H
    ADP(H) + Mg ⊂ ADP(H)-Mg, log K = 1.55
    CDP(H) + Mg ⊂ ADP(H)-Mg, log K = 1.60
f3, the fraction of HL in complexed form MHL f3 = [M] / ([M] + $K_{MHL}$)
f4, the fraction of HL in uncomplexed form HL f4 = 1 − f3
IV. STEP 4
Compute the fraction of each complexed form of L (refer to figure)
fracL = f2*f6
fracML = f2*f5
fracHL = f1*f4
fracMHL = f1*f3
V. STEP 5
Compute phosphate charge $Q_{phos}$ averaged over all forms of L
$Q_{phos}$ = Q(L)*fracL + Q(ML)*fracML + Q(HL)*fracHL + Q(MHL)*fracMHL
where each Q is defined in the figure
VI. STEP 6
Compute nucleobase charge $Q_B$ due to nucleobase adducts B
the equilibrium B + H ⊂ BH
KBH = [BH] / [B]*[H]
value of $K_{BH}$ log $K_{BH}$ = 4.5 for carboxylate
log $K_{BH}$ = 12 for arginine or quaternary ammonium salt
note: at pH values 6.5–8.5, these groups are effectively fixed negative or positive charges
fraction of protonated and unprotonated forms fracBH = [H] / ([H] + $K_{BH}$)
fracB = 1 − fracBH
charge $Q_B$ = charge of B
$Q_{BH}$ = charge of BH
$Q_B$ = fracBH*$Q_{BH}$ + fracB*$Q_B$
VII. STEP 7
Compute γ-label charge $Q_G$ from γ-label adducts G
same logic as step 6
$Q_G$ = fracGH*$Q_{GH}$ + fracG*$Q_G$
VIII. STEP 8
Compute overall charge $Q_{N-PPP-F}$ on N-PPP-F
$Q_{N-PPP-F}$ = $Q_{phos}$ + $Q_B$ + $Q_G$ Example II Materials and Methods Modeling was performed of nucleotide sequencing using the system of the present invention. The simulations were performed with MATLAB (The MathWorks, Inc., Natick, Mass.) version R11.1, running on an Intel Pentium III-based machine. The operating system is Windows 98 (second edition). Nucleotide motion was calculated according to the following method. For each time step,
1. Determine the voltage at this time for both pairs of plates from a given waveform.
2. Calculate the electric field in the axial and transverse directions due to the voltage. Add in a vector-wise fashion for the total field.
3. Calculate the resultant velocity given the physical parameters of the molecule. Note that the charge and diffusion coefficient will be different for the quencher-nucleobase-dye moiety than for the released pyrophosphate-dye moiety.
4. Given the time step, calculate the resultant motion from the velocity.
5. Calculate a Gaussian-distributed movement due to diffusion.
6. Add the movement due to diffusion and the movement due to the electric field in a vector-wise fashion.
7. Move the molecule.

A. This example is similar to an electrophoretic case, wherein a DC field is applied axially.

In this example, no field is applied to the transverse plates, and a constant field is applied to the axial plates. The charge on the dye-nucleobase-quencher structure is −4, and the charge on the pyrophosphate-dye structure is −2. The axial field strength is $3 \times 10^5$ V/m, which would result from, for example, 3000 V across 1 cm.

In this example, the charge ratio between the unincorporated structures and the released dyes is 2, meaning that on average, the unincorporated structures travel twice as fast as the released dyes.

B. This example illustrates a DC field applied axially and an AC field applied transversely.

In this example, the transverse field is modulated in a sinusoidal fashion. The charge ratio is 2. The axial field strength is the same as in Example 1, and the transverse field has a peak-to-peak amplitude of 50 V. The frequency of oscillation is 200 Hz. The background molecules spread or "throw" their photons over a larger area, since their spatial modulation (peak-to-peak length of their paths) is greater due to stronger response to the E field. This has the effect of smoothing out the background, resulting in a higher signal-to-noise ratio (SNR). The preferred setup is to have the released phosphate have a small, but distinguishable path amplitude (if the amplitude were too great, it would also scatter its photons over too many CCD pixels).

Example III

This example illustrates an AC field applied axially and an AC field applied transversely.

Another case of interest is to have only AC components to the transverse and axial fields. If both field strengths are sinusoids comparable in amplitude and frequency, the resultant path coupled with diffusion paints a bright spot on the image when an incorporation event occurs. This method allows a continual "wash" over the enzymes to encourage incorporation, while limiting the total traversal breadth to keep photons concentrated in one place. Moreover, it is advantageous to use this method when the CCD camera is reading out and the shutter is closed, to avoid having signals travel far away during the "blackout" time (images are not being recorded). The peak axial field strength is the same as the previous two DC examples, while the peak transverse voltage is 50 V. Both waveforms are at 200 Hz.

Example IV

This example illustrates an AC and DC field applied axially and an AC applied transversely.

Applying both AC and DC fields to the axial plates results in shorter, fatter streaks since the molecules follow a spiral pattern down the flowcell. The DC component ensures eventual washing away of all molecules. The AC field in the transverse direction encourages unincorporated molecules to throw their photons over a larger area, which as before tends to smooth out the background.

Example V

This example illustrates that $Mg^{++}$ can change the electrophoretic mobility of dTTP and dTDP (unlabeled) from more negative to less negative. It also shows that the electrophoretic mobility of dTTP-(++)-BODIPYTR can be changed from negative to positive as the $Mg^{++}$ concentration increases.

5.1 Analysis of dTTP and dTDP by Capillary Electrophoresis

The effect of $Mg^{++}$ on the electrophoretic mobility of dTTP and dTDP was determined by capillary electrophoresis. Electrophoresis buffer contained 50 mM Tris-acetate pH 8.0, 60 mM KCl, and various concentrations of $MgCl_2$ (3, 4, 6, 10, 15, 25 and 40 mM). The sample contained 0.5 mM nucleotide (dTTP or dTDP; Sigma) and 0.8 mM mesityl oxide (electroneutral marker; Sigma). The samples were analyzed by capillary electrophoresis (Hewlett Packard) using an uncoated fused silica capillary (40 cm from injection end to detection zone). Voltage was 8.5 kV and peaks were monitored by optical absorbance at 260 nm. Electrokinetic velocity of each sample peak was calculated by dividing distance (40 cm) by elution time. Electroosmotic flow (EOF) of the bulk buffer is taken as the velocity of the mesityl oxide marker. Nucleotide electrophoretic velocity is the nucleotide electrokinetic velocity minus EOF. Nucleotide electrophoretic velocities are plotted as a function of $Mg^{++}$ concentration (FIG. 11A). The dTTP has a more negative electrophoretic mobility than the dTDP, as expected, because dTTP has an additional phosphate group ("negative mobility" means that the molecule moves like a negatively-charged molecule, towards the positive electrode). $Mg^{++}$ changed the electrophoretic mobility of both nucleotides from more negative to less negative.

5.2 Analysis of dTTP-BOS(++)-BODIPYTR by Gel Electrophoresis

The net charge on dTTP was adjusted in a positive direction by adding two quaternary amine groups on a linker attached to the γ-phosphate; an electroneutral dye marker was also attached to the linker, giving the compound dTTP-BQS(++)-BODIPYTR (FIG. 4). The effect of $Mg^{++}$ on the electrophoretic mobility of this nucleotide was determined by agarose gel electrophoresis. Electrophoresis buffer contained 50 mM Tris-acetate pH 8.0, 60 mM KCl, and various concentrations of $MgCl_2$ (0, 1, 1.5, 2, 3, 4, 6, 10, 15, 25 and 40 mM). Slab gels (4% agarose) were cast in each electrophoresis buffer and each gel was placed in a slab gel apparatus (Bio-Rad) containing the respective electrophoresis buffer. The sample wells were loaded with 5 μL of 20 μM dTTP-BQS(++)-BODIPYTR and electrophoresis was performed at 6 V per cm for 10 min. The gels were photographed on a UV transilluminator and the separate images were assembled into a single figure (FIG. 11B). As was seen with unlabeled dTTP (FIG. 11A), $Mg^{++}$ added positive charge to the nucleotide. However, because the two quaternary amines make the labeled nucleotide less negative as compared to the unlabeled nucleotide, the effect of $Mg^{++}$ is to change the nucleotide mobility from net negative to net positive.

Example VI

This example illustrates the synthesis of a charge-switch nucleotide of the present invention.

6.1 Preparation of Compound 1'

Figure 12:
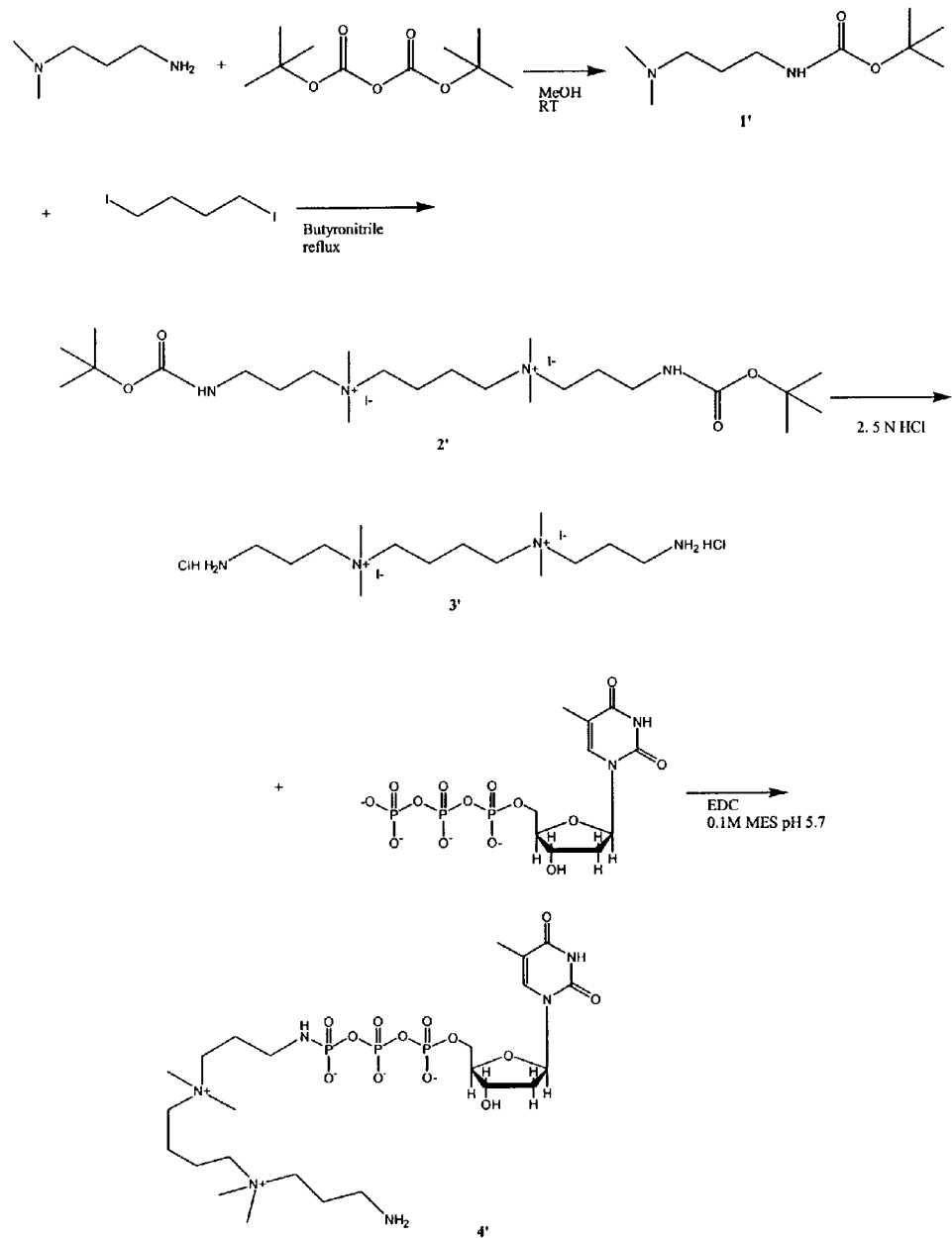
FIG. 12 illustrates a synthetic scheme of an embodiment of the present invention.
Figure 12:
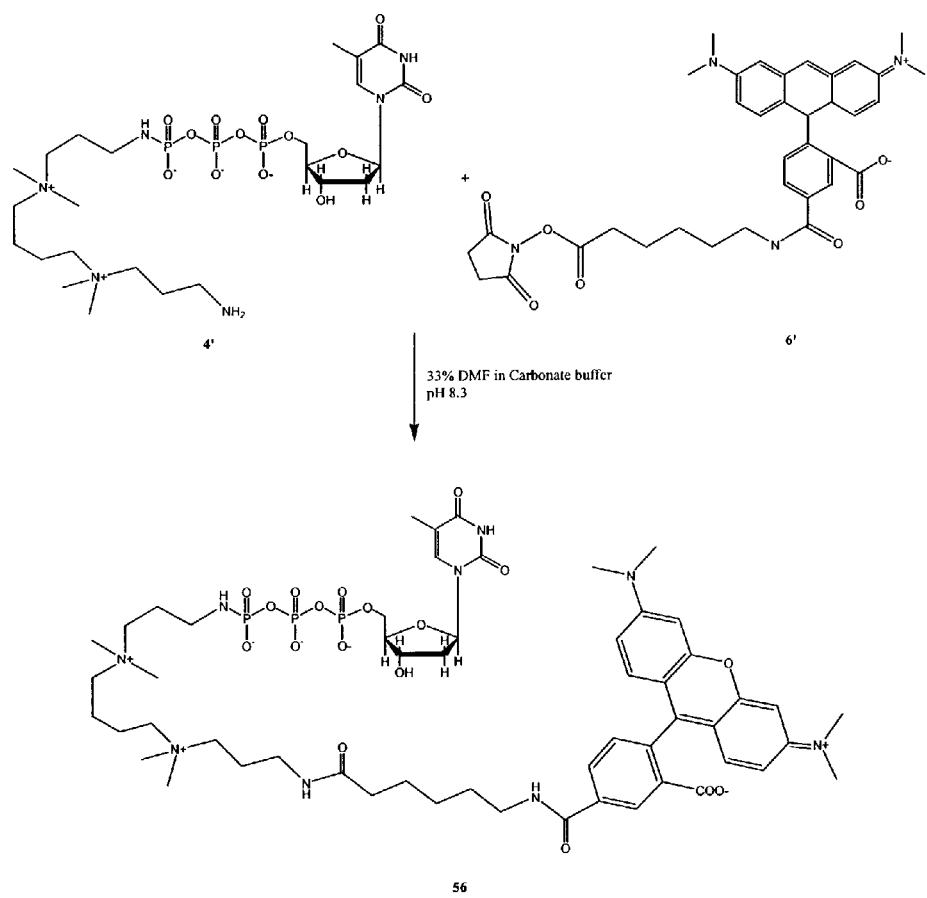

In FIGS. 12A and B, 11.2 g of t-BOC anhydride (Aldrich, 218 g/mol, 52.4 mmole) is dissolved in 100 mL of reagent grade methanol (Fisher). 10 mL of N,N dimethylpropyl amine (Aldrich, 102.1 g/mol, 48.9 mmole) is added slowly to the reaction mixture. The reaction mixture is allowed to stir at room temperature for 16 hours. The reaction is deemed complete by TLC (C18, 1:1 Acetonitrile/Methanol, $I_2$ visualization) Solvent is evaporated in vacuo. Compound 1' (FIG. 15) is then purified by column chromatography (1:1 methylene chloride and methanol). Fractions containing pure compound 1 were combined and evaporated in vacuo to yield 17.7 g of purified product.

6.2 Preparation of Compound 2'

2.16 g of compound 1 (202 g/mol, 10.7 mmole) is dissolved in 10 mL dry reagent grade butyronitrile (Fisher). 1.51 grams of 1,4-diiodobutane is added and the mixture is refluxed at 135° C. for 24 hours. The reaction is checked by TLC (C18, 40% aqueous methanol, $I_2$ visualization) and determined to be complete. The reaction mixture is precipitated with diethyl ether and collected. After dissolving in methanol, the product is again precipitated with diethyl ether. The resultant viscous yellow residue is dissolved in methanol and the solvent is removed in vacuo. This material is used without purification to form compound 3.

6.3 Preparation of Compound 3'

After drying, compound presents as fluffy yellow solid. This material is dissolved in 20 mL of 5N HCl (prepared from concentrated HCl, Fisher) and stirred at room temperature for 5 hrs. Reaction completion is checked by TLC (C18, 1:1 Acetonitrile/methanol, ninhydrin and UV visualization). The acid solution is concentrated and product of interest is precipitated with diethyl ether. This solid is redissolved in methanol and re-precipitated in diethyl ether. The solid is collected and dried under vacuum. This product is used without further purification or determination of yield.

6.4 Preparation of Compound 4'

1.1 mg of dTTP (Sigma, 492.7 g/mol, 2.2 μmole) is dissolved in 100 μL 0.1 M MES pH 5.7. In a separate vial, 19.7 mg of EDC (Aldrich, 191.7 g/mol, 100 μmole) is dissolved in 100 μL of 0.1 M MES pH 5.7. These two solutions are combined and allowed to incubate at room temperature for 10 minutes.

11.6 mg of compound 3 is dissolved in 400 μl of MES buffer. The pH of this solution is checked with pH strips and found to be 5.8. This solution is added to the activated nucleotide and the reaction is allowed to stand at room temperature for 110 minutes. The reaction is monitored by reverse phase HPLC. The product of interest is isolated by reverse phase HPLC (C18, 4–80% Acetonitrile in 0.1 M TEAA over 20 minutes). Solvent is removed from purified compound #4 in vacuo. Yield is 12.7% from dTTP.

6.5 Preparation of Compound 56

Compound 4' (0.15 μmole, 975 g/mol) is dissolved in 100 μl of 50 mM carbonate buffer at pH 8.3. pH is checked by colorphast pH strips and found to be 8.3. 9.4 μL of 22 mM TAMRA-X-SE 6' (Molecular Probes, 640.59 g/mol, 0.23 μmole) is added and the reaction mixture is allowed to stand at room temperature for 18 hours in the dark. Reaction is determined complete after hydrolysis of all active dye ester. Product of interest 56 is isolated by reverse phase HPLC (C18, 4–80% Acetonitrile in 0.1 M TEAA over 20 minutes). Solvent is removed from product in vacuo in the dark. Yield is 30% from compound 4.

Example VII

This example illustrates an assay system to demonstrate charge-switching activity of compounds of the present invention.

This assay is used to test for a change in the electric charge associated with a dye attached to the phosphate of a nucleotide. The charge switch on the dye is caused by cleavage of a phosphodiester bond that links the dye to the nucleotide. In this example, cleavage is catalyzed by snake venom phosphodiesterase.

Phosphodiesterase I (from Crotalus adamanteus venum; USB Corp.) was dissolved in 110 mM Tris-HCl (pH 8.9) containing 110 mM NaCl, 15 mM $MgCl_2$, to a final enzyme concentration of 40 units/mL. The reaction sample (50 μL) contained Phosphodiesterase I (3.6 units/mL), HEPES-NaOH buffer (40 mM) and dTTP-BQS-BTR (38 μM). A control sample was the same as the reaction sample except that the enzyme was omitted. The reaction and control samples were incubated at 37° C. for 1 hour and were analyzed by electrophoresis in a 5% agarose using a running buffer comprising 50 mM Tris-HCl pH 8.0, 60 mM KCl, 2 mM $MgCl_2$. The BTR dye in the reaction sample migrated toward the negative electrode (−), while the dye in the control sample migrated toward the positive electrode (+).

Example VIII

This example demonstrates charge-switching activity of compounds of the present invention.

Materials

Microchannels were created by replica molding polydimethylsiloxane (PDMS) against a silicon master. The channels are 10 microns wide by 10 microns deep. Two intersecting channels perpendicular to one another were formed in the shape of a cross. The distal ends of each channel empty into separate circular wells of diameter 4 mm and depth 5 mm.

With reference to FIG. 9, platinum electrodes were placed into the wells of the vertical channel 95a, 95b. (Although not explicitly shown in the FIG. 9, the distal ends of each channel empty into separate circular wells i.e., 95a, 95b; and 96a, 96b. For this embodiment, the designations 95a, 95b and 96a, 96b are used interchangeably to denote the wells of the channels and the electrodes and pressure forces respectively). Voltage was applied across these electrodes to introduce an electric field down the vertical channel. Simultaneously, pressure was applied to both wells 96a, 96b. Pressure applied to well 96a forces dye towards the cross intersection, while pressure applied to well 96b prevents dye from continuing towards well 96b (dye is forced into the vertical channel towards either well 95a, 95b.

The 530.9 line of a tunable argon-krypton laser was used to directly illuminate the flowcell channels. A cleanup filter (center wavelength 530 nm, bandwidth 10 nm) was inserted between the laser output and the flowcell. The emitted fluorescence was viewed with an inverted microscope using an air objective (10×, NA 0.25). After the objective a holographic notch filter (center wavelength 530.9 nm, bandwidth 3 nm) and a bandpass emission filter (center wavelength 575 nm, bandwidth 50 nm) removed Rayleigh and Raman scatter. The resulting signal was imaged onto a CCD camera and captured onto a PC with frame grabber hardware and software.

The buffer consisted of a mixture of 20 mM Tris-OAc pH 8, 3% (w/v) polyvinylpyrolidone (PVP), 2 mM $MgCl_2$, and 0.1% Tween 20. A buffer+dye solution was formed by adding either gly-TAMRA (−1 charge) or BQS-TAMRA (+1 charge) dye to the same buffer constituents, such that the dye concentration was 1 μM.

The PDMS molds and borosilicate cover slips were treated in an oxygen plasma chamber for 1 minute. After treatment, upon contact the PDMS and glass would irreversibly bond. The plasma also causes the flowcell and glass surfaces to become hydrophilic, permitting easy filling of the channels by capillary action.

I. The purpose of this experiment was to show that the negatively charged dye could be forced to turn a corner by the application of an electric field while suppressing electroosmotic flow (EOF).

Wells at the end of the vertical channels 95a, 95b, and at the end of the horizontal channel 96b were filled with 40 μL of buffer solution while watching the cross intersection on a monitor showing the magnified image. After the channels were wetted, well 96a was filled with 40 μL of buffer+dye solution. A pressure of 0.28 psi was applied to well 96a, while simultaneously applying 0.43 psi to well 96b. An electric field of 820 V/cm was applied from well 95a to well 95b (well 95a containing the positive electrode).

The electric field forces the negatively-charged dye towards well 95a (the positive electrode). EOF is known to be suppressed since the dye does not move away from the positive electrode (EOF arising from a negatively-charged wall causes a bulk flow away from the positive electrode).

The polarity was then switched; an electric field equal in magnitude but opposite in direction was applied across wells at the end of the vertical channels. The dye switched direction so that it was again moving towards the positive electrode.

II The purpose of this experiment was to show that positively charge dye also could be forced to turn a corner by the application of an electric field.

Wells 95b, 95a, and 96b were filled with 40 μL of buffer solution while watching the cross intersection on a monitor. After the channels were wetted, well 96a was filled with 40 μL of buffer+dye solution. A pressure of 0.88 psi was applied to well 96a, while simultaneously applying 1.09 psi to well 96b. An electric field of 455 V/cm was applied from well 95a to well 95b.

The electric field forces the positively-charged dye towards well 95b (the negative electrode). The polarity was then switched to confirm that the dye would change direction towards well 95a.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A microfluidic device useful for analyzing a reaction, the device comprising:
a substrate;
at least two microchannels disposed on the substrate, wherein said microchannels are in fluid communication with each other;
an immobilization zone within a first one of said microchannels, wherein at least a portion of a reactant is immobilized proximal the immobilization zone to allow for a reaction to occur so as to produce a reaction product; and
a detection zone within a second one of said microchannels,
wherein there is substantially no electric field within the first microchannel proximal the immobilization zone, and wherein a biasing force moves the reaction product into the detection zone within the second microchannel,
wherein the reactant includes a charge-switch nucleotide probe, and wherein the probe is a nucleotide triphosphate and the terminal phosphate includes a fluorophore attached thereto.

2. The device of claim 1, wherein the biasing force includes one of an electric field, a pressure field and a combination of an electric field and a pressure field.

3. The device of claim 1, wherein the biasing force includes a pressure field in the first microchannel and an electric field within the second microchannel.

4. The device of claim 1, wherein the reaction occurs in a reaction zone proximal the immobilization zone.

5. The device of claim 4, wherein at least a portion of the reaction zone is within the first microchannel.

6. The device of claim 4, wherein at least a portion of the reaction zone is within the second microchannel.

7. The device of claim 4, further including a third microchannel fluidly coupling the first and second microchannels, wherein at least a portion of the reaction zone is within the third microchannel.

8. The device of claim 7, wherein there is substantially no electric field within said third microchannel.

9. The device of claim 4, wherein at least a portion of the reaction zone is in a flow path between the immobilization zone and the detection zone.

10. The device of claim 1, wherein the reactant is provided on a solid phase.

11. The device of claim 10, wherein the reactant includes a nucleic acid complex immobilized on the solid phase in a single molecule configuration.

12. The device of claim 10, wherein the solid phase is magnetic or magnetizable, the device further including a magnetic field generating element positioned proximal the immobilization zone for holding the solid phase.

13. The device of claim 12, wherein the magnetic field generating element includes one of a permanent magnet and one or more electric coils.

14. The device of claim 1, wherein the reaction product has a net charge different from the net charge of the reactant.

15. The device of claim 14, wherein the net electric charge of the reaction product has an opposite polarity to the electric charge of the reactant.

16. The device of claim 14, wherein the net electric charge of the reaction product has the same polarity as the electric charge of the reactant, but has a charge magnitude different that the charge magnitude of the reactant.

17. The device of claim 16, wherein the reactant product is separated from the reactant due to different mobilities in a bulk fluid flow away from the detection zone in the second microchannel based on the difference in charge magnitude between the reactant and the reaction product.

18. The system device of claim 1, wherein the reaction is one of a molecular cleavage reaction and an enzymatic cleavage reaction.

19. The device of claim 1, wherein the second microchannel has a depth within at least the detection zone of between about 0.5 µm and about 1.0 µm.

20. The device of claim 1, further including means for generating an evanescent excitation field within the detection zone, and wherein the second microchannel has a depth within at least the detection zone that is less than approximately four times the exponential decay constant of the evanescent excitation field within the detection zone.

21. The device of claim 1, further comprising a third microchannel, coupled to the second microchannel between the immobilization zone and the detection zone, for supplying a second reactant material to the reaction zone.

22. The device of claim 1, wherein the reaction zone is sufficiently close to the detection zone so as to maintain the order of reaction product produced in the reaction as it enters the detection zone.

23. The device of claim 1, wherein the reaction zone is not proximal the detection zone, and wherein the biasing force is sufficiently strong so as to maintain the order of reaction product produced in the reaction as it enters the detection zone.

* * * * *